(12) United States Patent
Sun

(10) Patent No.: US 8,748,610 B2
(45) Date of Patent: Jun. 10, 2014

(54) COMPOUNDS AS TRPV1 ANTAGONISTS, PHARMACEUTICAL COMPOSITIONS AND MEDICAL USES THEREOF

(75) Inventor: Qun Sun, Princeton, NJ (US)

(73) Assignee: FL Therapeutics LLC, Princeton, NJ (US)

( * ) Notice: Subject to any disclaimer, the term of this patent is extended or adjusted under 35 U.S.C. 154(b) by 0 days.

(21) Appl. No.: 13/498,641

(22) PCT Filed: Sep. 27, 2010

(86) PCT No.: PCT/CN2010/077357
§ 371 (c)(1),
(2), (4) Date: Mar. 28, 2012

(87) PCT Pub. No.: WO2011/038662
PCT Pub. Date: Apr. 7, 2011

(65) Prior Publication Data
US 2012/0184509 A1     Jul. 19, 2012

(30) Foreign Application Priority Data
Sep. 30, 2009    (CN) .......................... 2009 1 0205210

(51) Int. Cl.
*A01N 55/00*    (2006.01)
*C07F 7/02*     (2006.01)
*C07F 7/08*     (2006.01)

(52) U.S. Cl.
CPC .................................. *C07F 7/0814* (2013.01); *A01N 55/00* (2013.01)
USPC .............................................. 546/14; 514/63

(58) Field of Classification Search
CPC ................................................... C07F 7/0814
See application file for complete search history.

(56) References Cited

U.S. PATENT DOCUMENTS 7,772,254 B2    8/2010   Sun

FOREIGN PATENT DOCUMENTS

| CN | 1863790 A | 11/2006 |
|----|-----------|---------|
| WO | WO03066595 A2 | 8/2003 |
| WO | WO2005030753 A2 | 4/2005 |
| WO | WO2008133973 A1 | 11/2008 |
| WO | WO2009023539 A2 | 2/2009 |
| WO | WO 2010092342 A1 * | 8/2010 |

OTHER PUBLICATIONS

Silverman, R. "The Organic Chemistry of Drug Design and Drug Action," 2004, Elsevier, pp. 29-32.*
Birder et al., "Altered urinary bladder function in mice lacking the vanilloid receptor TRPV1," Nat. Neurosci., 5(9):856-860, Sep. 2002.
Bley, "Recent developments in transient receptor potential vanilloid receptor 1 agonist-based therapies," Exp. Opin Investig Drugs., 13(11):1445-1456, Nov. 2004.
Caterina et al., "Impaired nociception and pain sensation in mice lacking the capsaicin receptor," Science, 288(5464):306-313, Apr. 2000.
Caterina et al., "The capsaicin receptor: a heat-activated ion channel in the pain pathway," Nature, 389(6653):816-824, Oct. 23, 1997.
Davis et al., "Vanilloid receptor-1 is essential for inflammatory thermal hyperalgesia," Nature, 405(6783): 183-187, May 11, 2000.
Di Marzo et al., "Endovanilloid signaling in pain," Curr. Opin. Neurobiol., 12(4):372-379, Aug. 2002.
Mezey et al., "Distribution of mRNA for vanilloid receptor subtype 1 (VR1), and VR1-like immunoreactivity, in the central nervous system of the rat and human," Proc Natl Acad Sci U S A., 97(7):3655-3660, Mar. 28, 2000.
Pomonis et al., "N-(4-Tertiarybutylphenyl)-4-(3-cholorphyridin-2-yl)tetrahydropyrazine-1(2H)-carbox-amide (BCTC), a novel, orally effective vanilloid receptor 1 antagonist with analgesic properties: II. in vivo characterization in rat models of inflammatory and neuropathic pain," J Pharmacol Exp Ther., 306(1):387-393, Epub. Apr. 29, 2003.
Walker et al., "The VR1 antagonist capsazepine reverses mechanical hyperalgesia in models of inflammatory and neuropathic pain," J. Pharm. Exp. Ther. 304(1): 56-62, Jan. 2003.
International Search Report for PCT/CN2010/077357, dated Jan. 13, 2011, 6 pages.
International Preliminary Report on Patentability for PCT/CN2010/077357, issued Apr. 3, 2012, 7 pages.
Written Opinion for PCT/CN2010/077357, mailed Jan. 13, 2011, 6 pages.

* cited by examiner

*Primary Examiner* — Heidi Reese
(74) *Attorney, Agent, or Firm* — Fish & Richardson P.C.

(57) ABSTRACT

A kind of new compounds, and their pharmaceutically acceptable salts, and hydrates are disclosed. The pharmaceutical composition thereof is also provided. And also are the medical uses of the compounds, pharmaceutically acceptable salts, hydrates and the pharmaceutical composition for treating the TRPV1-mediate diseases.

31 Claims, No Drawings

COMPOUNDS AS TRPV1 ANTAGONISTS, PHARMACEUTICAL COMPOSITIONS AND MEDICAL USES THEREOF

FIELD OF THE INVENTION

The present invention relates to compounds as TRPV1 antagonists and their pharmaceutically acceptable salts and hydrates, compositions comprising such compounds and their pharmaceutically acceptable salts and hydrates, and therapeutic uses of such compounds and their pharmaceutically acceptable salts and hydrates. This application claims the benefit of china patent application no. 200910205210.3, filed Sep. 30, 2009, the entire disclosure of which is incorporated by reference herein in its entirety.

BACKGROUND OF THE INVENTION

The vanilloid receptor (VR1 or TRPV1), a non-selective ligand-gated cation channel belonging to the Transient Receptor Channel family (TRP family) of cation channels, is highly expressed on the peripheral termini of small diameter sensory neurones innervating many tissues including skin, bladder, airway and gastrointestinal tract. More specifically TRPV1 receptors are located on a subset Aδ and C fibres, the afferents commonly associated with nociception (Mezey et al., Proc. Natl. Acad. Sci. 97, 3655-3660, 2000). Characterisation of this channel at the molecular level identified it as the target of the vanilloid capsaicin, the main pungent constituent of hot chilli peppers (Caterina et al., Nature 389, 816-824, 1997). Indeed, sensitivity to capsaicin has been used for many years as a marker of nociceptor activity. These, polymodal nociceptors are activated by multiple noxious stimuli including chemical, mechanical and thermal. Study of the functional properties of TRPV1 demonstrated that this receptor shares many properties common to nociceptors including activation by thermal stimuli (>43° C.) and chemicals (including capsaicin and endovanilloids such as N-arachidonoyl-dopamine (NADA) and lipoxygenase metabolites), as well as sensitisation and activation by acidification. Furthermore, inflammatory mediators (including ATP and bradykinin) have been shown to functionally sensitise TRPV1 in vitro. This evidence suggests that TRPV1 has an integral role in the polymodal detection of noxious stimuli and contributes to the transduction of inflammatory pain responses and potentially also peripheral tissue injury (reviewed in Di Marzo et al., Curr. Opin. Neurobiol. 12, 372-379, 2002).

A role for TRPV1 in the detection of painful stimuli is also inferred from data in gene knockout mice. Mice null for TRPV1 show attenuated development of behavioural thermal hyperalgesia after an inflammatory insult (Caterina et al., Science 288, 306-313, 2000, Davis et al., Nature 405, 183-187, 2000). Small diameter sensory neurones from these animals also show altered responses to thermal and acid stimuli.

In humans, intradermal exposure to capsaicin leads at first to the sensation of burning pain due to neuronal excitation, followed by a long lasting period of analgesia which is believed to be a consequence of functional desensitisation (reviewed in Bley, Exp. Opin Investig Drugs. 13, 1445-1456, 2004). This led to the development of TRPV1 agonists as potential analgesic compounds. However, these compounds suffer from a number of issues including pain and a burning sensation on initial application. More recently, TRPV1 antagonists including capsazepine (Walker et al., J. Pharm. Exp. Ther. 304, 56-62, 2003) and BCTC (Pomonis et al., J. Phar. Exp. Ther. 306, 387-393, 2004) have been shown to be active in a variety of preclinical animal models of inflammatory and neuropathic pain.

In addition to a role in pain transduction there is also growing evidence for a role for TRPV1 in regulating afferent and efferent function of sensory nerves and the function of non-neuronal cells. Indeed, altered bladder function, with a higher frequency of low amplitude, non-voiding bladder contractions and an increase in bladder capacity has been observed by in TRPV1 KO mice (Birder et al., Nat. Neurosci. 5, 856-860, 2002). This may involve neuronal TRPV1 and TRPV1 expressed on uroepithelial cells. Thus, there is clear evidence to suggest that agents modulating TRPV1 activity will have utility not only in pain states and other diseases involving inflammation but also in conditions involving hyperactivity of primary sensory fibres (e.g. bladder overactivity and urge incontinence).

The International Patent Application WO 2008133973 discloses the compounds with the general structure (i) below that are useful for treating or preventing pain and other diseases.

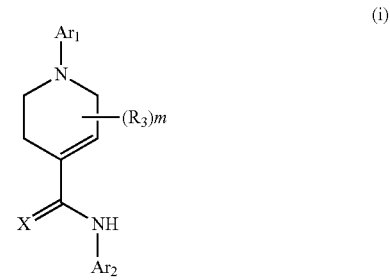

(i)

The International Patent Application WO 2009023539 discloses the amino compounds with the general structure (ii) below as TRPV1 antagonists that are useful for treating or preventing TRPV1 mediated disorders, such as pain, UI, ulcer, IBD, and IBS diseases.

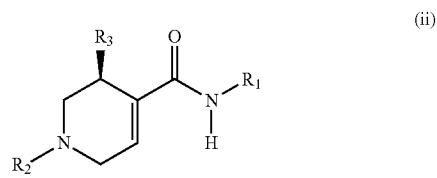

(ii)

However, there remains a need for additional compounds that are useful in the treatment of TRPV1 mediated disorders.

The application referenced above, any reference can not be understood as recognition is described in reference to this application of existing technologies

DESCRIPTION OF THE INVENTION

One of the purposes of this invention is to provide a new class of compounds with medicinal value, used to treat diseases such as TRPV1-mediated diseases and other illnesses, such as inflammatory or neuropathic pain and diseases involved with sensory nerve function such as asthma, rheumatoid arthritis, osteoarthritis, inflammatory bowel disease, irritable bowel disease, incontinence, ulcers, migraine and psoriasis. More specifically, the present invention include compounds for the treatment of acute, inflammatory and neuropathic pain, pain, general headache, migraine, cluster headache, mixed vascular and non-vascular syndromes, tension headache, general inflammation, arthritis, rheumatic diseases, osteoarthritis, inflammatory bowel disease, anxiety, depression, inflammatory eye disorders, inflammatory or unstable bladder disorders, psoriasis, inflammatory factors, skin diseases, chronic inflammation, inflammatory pain and associated hyperalgesia and allodynia, neuropathic pain and associated hyperalgesia and allodynia, diabetic neuropathy, pain, burning, persistent sympathetic pain, differentiation syndromes, asthma, epithelial tissue damage or dysfunction, herpes simplex, respiratory, urogenital, gastrointestinal or vascular regions visceral movement disorders, wounds, burns, allergic skin reactions, pruritus, vitiligo, general gastrointestinal disorders, stomach ulcers, duodenal ulcers, diarrhea, the stomach necrosis factor-induced damage, hair growth, vasomotor or allergic rhinitis, bronchial disorders or bladder disorders.

Another objective of the present invention is to provide the pharmaceutical composition containing the class of new compounds and its pharmaceutically acceptable salt or hydrate.

The invention further aims to provide such a new compound and its pharmaceutically acceptable salt or hydrate, pharmaceutical compositions containing such new compounds and their pharmaceutically acceptable salt or hydrate which can inhibit the function of TRPV1 in the cell expressing TRPV1, and can be used to prepare for the treatment of pain, urinary incontinence, ulcers, inflammatory bowel disease or allergic bowel disease and other diseases.

The present invention also aims to provide methods using the above compounds and a combination containing above compounds to treat the TRPV1-mediated disease, and to treat pain, urinary incontinence, ulcers, inflammatory bowel disease or allergic bowel disease and other diseases.

One aspect of the present invention encompasses compounds of Formula (I) or any pharmaceutically-acceptable salt or hydrate thereof:

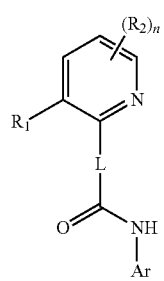

Wherein:
L is:

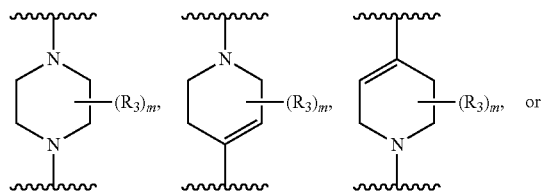

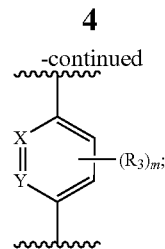

Ar is:

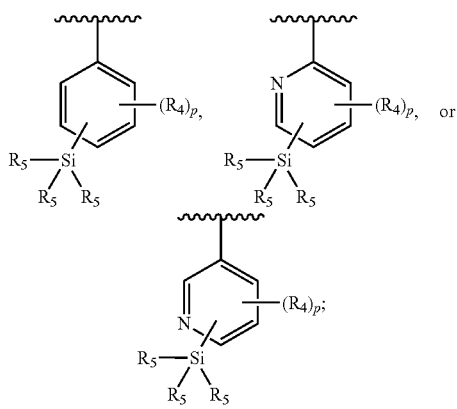

Each X is independently N or C;
Each Y is independently N or C;
m is 0, 1, 2, 3 or 4;
n is 0, 1, 2 or 3;
p is 0, 1, 2 or 3;
$R_1$: —H, -halo, —($C_1$-$C_4$)alkyl, —$NO_2$, —CN, —$NH_2$, —C(halo)$_3$, —CH(halo)$_2$, —$CH_2$ (halo), —OC(halo)$_3$, —OCH(halo)$_2$ or —$OCH_2$ (halo);
each $R_2$ is independently
(a) —H, -halo, —OH, —O($C_1$-$C_4$)alkyl, —CN, —$NO_2$, or —$NH_2$;
(b) —($C_1$-$C_{10}$)alkyl, —($C_2$-$C_{10}$)alkenyl, or —($C_2$-$C_{10}$)alkynyl;
(c) -phenyl, each of which is unsubstituted or substituted with 1, 2 or 3 independently selected $R_7$ groups; or
(d) a group of Formula Q; wherein Q is:

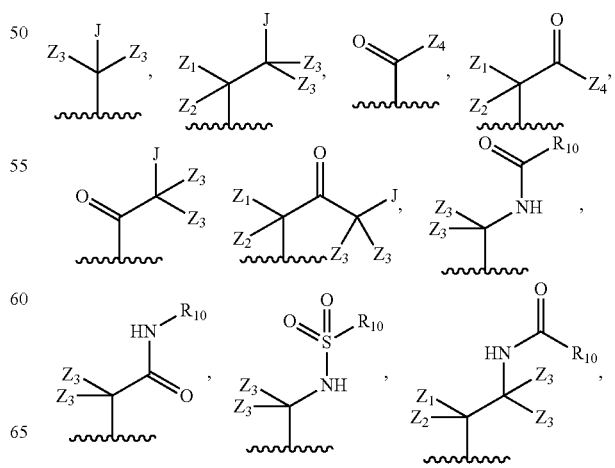

-continued

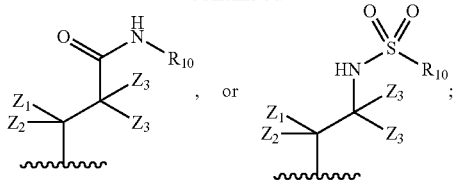

Of which:
$Z_1$ is H, $OR_7$, $SR_7$, $CH_2$—$OR_7$, $CH_2$—$SR_7$, $CH_2$—$N(R)_2$, or halo;
$Z_2$ is H, $(C_1-C_6)$alkyl, $(C_2-C_6)$alkenyl, $(C_2-C_6)$alkynyl, $CH_2$—$OR_7$, phenyl, or halo;
Each $Z_3$ is independently H, $(C_1-C_6)$alkyl, $(C_2-C_6)$alkenyl, $(C_2-C_6)$alkynyl, or phenyl;
$Z_4$ is H, OH, $OR_{10}$, $(C_1-C_6)$alkyl, or $N(R_{10})_2$;
J is $OR_{10}$, $SR_{10}$, $N(R_{10})_2$ or CN;
Each $R_3$ is independently
(a) —H, $CH_2$—$OR_7$, $(C_1-C_6)$alkyl, halo, CN, OH, $NO_2$, or $NH_2$;
(b) two $R_3$ groups together form a $(C_2-C_6)$bridge, which is unsubstituted or substituted with 1, 2 or 3 independently selected $R_4$ groups, and which bridge optionally contains —HC=CH— within the $(C_2-C_6)$bridge; or
(c) two $R_3$ groups together form a —$CH_2$—N(Ra)—$CH_2$— bridge, a

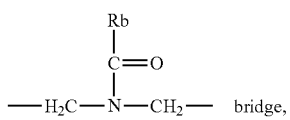

or a

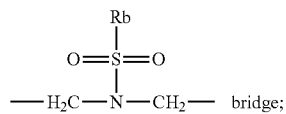

$R_a$ is —H, $(C_1-C_6)$alkyl, $(C_3-C_8)$cycloalkyl, —$CH_2$—C(O)—$R_c$, —$CH_2$—C(O)—$OR_c$, —$CH_2$—C(O)—$N(R_c)_2$, —$(CH_2)_2$—O—$R_c$, —$(CH_2)_2S(O)_2$—$N(R_c)_2$, or —$(CH_2)_2$—$N(R_c(O)_2$—$R_c$;
Each $R_b$ is independently:
(a) —H, $(C_1-C_6)$alkyl, $(C_3-C_8)$cycloalkyl, —$N(R_c)_2$, or $N(R_c)$—$(C_3-C_8)$cycloalkyl;
(b) phenyl, pyridyl, or naphthyl, each of which is unsubstituted or substituted with 1, 2 or 3 independently selected $R_7$ groups;
each $R_c$ is independently —H or $(C_1-C_4)$alkyl;
each $R_4$ is independently:
(a) $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is optionally substituted with 1 or 2 hydroxy groups;
(b) $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is substituted with 1 or 2 $R_d$; or
(c) —H, $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, CH=$NR_7$, $N(R_7)_2$, $NR_7OH$, $OR_7$, $C(O)R_7$, $C(O)OR_7$, $OC(O)OR_7$, $SR_7$, $S(O)R_7$, $S(O)_2R_7$, or —$R_7$;

each $R_1$ is independently:
(a) $N(R_7)_2$, $NR_7OH$, $OR_7$, $C(O)R_7$, $C(O)OR_7$, $OC(O)OR_7$, $SR_7$, $S(O)R_7$, $S(O)_2R_7$; or
(b)

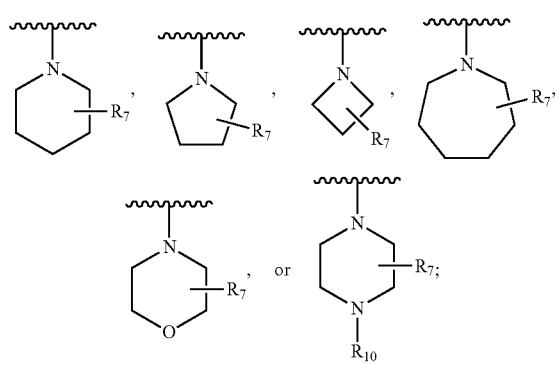

each $R_5$ is independently:
(a) —H, halo, $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is optionally substituted with 1 or 2 hydroxy groups; or
(b) $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is substituted by 1 or 2 substituents independently selected from:
(i) $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, CH=$NR_7$, $N(R_7)_2$, $NR_7OH$, $OR_7$, $C(O)R_7$, $C(O)OR_7$, $OC(O)OR_7$, $SR_7$, $S(O)R_7$, or $S(O)_2R_7$; or
(ii)

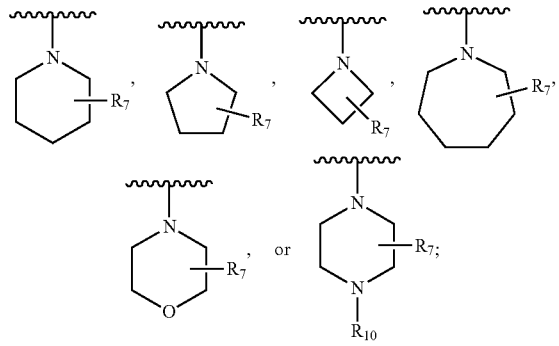

$R_7$ is —H, $(C_1-C_6)$alkyl, $(C_2-C_6)$alkenyl, $(C_2-C_6)$alkynyl, $(C_3-C_8)$cycloalkyl, $(C_5-C_8)$cycloalkenyl, phenyl, $(C_1-C_6)$haloalkyl, $(C_1-C_6)$hydroxyalkyl, $(C_1-C_6)$alkoxy$(C_1-C_6)$alkyl, $(C_1-C_6)$alkyl-$N(R_{10})_2$, or $CON(R_{10})_2$;
$R_{10}$ is —H, $(C_1-C_4)$alkyl, $(C_1-C_4)$haloalkyl, $(C_1-C_4)$hydroxyalkyl, or $(C_1-C_4)$alkoxy$(C_1-C_4)$alkyl.

One aspect of the present invention also encompasses compounds of Formula (II) or any pharmaceutically-acceptable salt or hydrate thereof:

(II)

[Structure of Formula (II): Ar—NH—C(O)—N(piperazine with $(R_3)_m$)—N—pyridine with $R_1$ and $(R_2)_n$]

wherein Ar, $R_1$, $R_2$, $R_3$, m, and n are as defined as above.

In one embodiment, together with any one of the above and following embodiments, Ar is:

[Structure: phenyl with $(R_4)_p$ and $R_5$—Si($R_5$)($R_5$)]

in one embodiment, together with any one of the above and following embodiments, Ar is:

[Structure: pyridine (N at position 2) with $(R_4)_p$ and $R_5$—Si($R_5$)($R_5$)]

In one embodiment, together with any one of the above and following embodiments, Ar is:

[Structure: pyridine (N at position 3) with $(R_4)_p$ and $R_5$—Si($R_5$)($R_5$)]

In one embodiment, together with any one of the above and following embodiments, m is 0.

In one embodiment, together with any one of the above and following embodiments, m is 1.

In one embodiment, together with any one of the above and following embodiments, m is 2.

In one embodiment, together with any one of the above and following embodiments, m is 3.

In one embodiment, together with any one of the above and following embodiments, m is 4.

In one embodiment, together with any one of the above and following embodiments, n is 0.

In one embodiment, together with any one of the above and following embodiments, n is 1.

In one embodiment, together with any one of the above and following embodiments, n is 2.

In one embodiment, together with any one of the above and following embodiments, n is 3.

In one embodiment, together with any one of the above and following embodiments, p is 0.

In one embodiment, together with any one of the above and following embodiments, p is 1.

In one embodiment, together with any one of the above and following embodiments, p is 2.

In one embodiment, together with any one of the above and following embodiments, p is 3.

In one embodiment, together with any one of the above and following embodiments, $R_1$ is: —H, -halo, —($C_1$-$C_4$)alkyl, —$NO_2$, —CN, —$NH_2$, —C(halo)$_3$, —CH(halo)$_2$, —$CH_2$(halo), —OC(halo)$_3$, —OCH(halo)$_2$ or —$OCH_2$(halo).

In one embodiment, together with any one of the above and following embodiments, $R_1$ is: -halo.

In one embodiment, together with any one of the above and following embodiments, $R_1$ is: Cl.

In one embodiment, together with any one of the above and following embodiments, $R_1$ is: F.

In one embodiment, together with any one of the above and following embodiments, $R_1$ is: —($C_1$-$C_4$)alkyl.

In one embodiment, together with any one of the above and following embodiments, In one embodiment, together with any one of the above and following embodiments, $R_1$ is: —$CF_3$.

In one embodiment, together with any one of the above and following embodiments, each $R_2$ is independently: —H, -halo, —OH, —O($C_1$-$C_4$)alkyl, —CN, —$NO_2$, or —$NH_2$.

In one embodiment, together with any one of the above and following embodiments, each $R_2$ is independently: —($C_1$-$C_{10}$)alkyl, —($C_2$-$C_{10}$)alkenyl, or —($C_2$-$C_{10}$)alkynyl.

In one embodiment, together with any one of the above and following embodiments, each $R_2$ is independently: —H.

In one embodiment, together with any one of the above and following embodiments, each $R_2$ is independently: -phenyl, each of which is unsubstituted or substituted with 1, 2 or 3 independently selected $R_7$ groups.

In one embodiment, together with any one of the above and following embodiments, each $R_2$ is independently: a group of Formula Q; wherein Q is:

[Structures showing various Q groups with $Z_1$, $Z_2$, $Z_3$, $Z_4$, J, $R_{10}$ substituents]

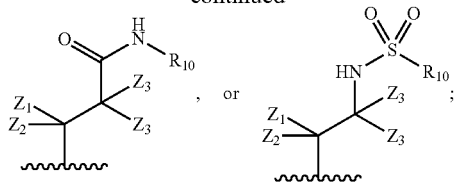

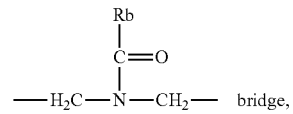

or a

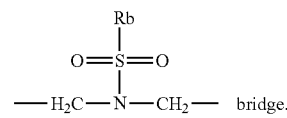

bridge.

Of which:
$Z_1$ is H, $OR_7$, $SR_7$, $CH_2$—$OR_7$, $CH_2$—$SR_7$, $CH_2$—$N(R_{10})_2$, or halo;
$Z_2$ is H, $(C_1$-$C_6)$alkyl, $(C_2$-$C_6)$alkenyl, $(C_2$-$C_6)$alkynyl, $CH_2$—$OR_7$, phenyl, or halo;
Each $Z_3$ is independently H, $(C_1$-$C_6)$alkyl, $(C_2$-$C_6)$alkenyl, $(C_2$-$C_6)$alkynyl, or phenyl;
$Z_4$ is H, OH, $OR_{10}$, $(C_1$-$C_6)$alkyl, or $N(R_{10})_2$;
J is $OR_{10}$, $SR_{10}$, $N(R_{10})_2$ or CN;

In one embodiment, together with any one of the above and following embodiments, each $R_2$ is independently: H.

In one embodiment, together with any one of the above and following embodiments, each $R_2$ is independently:

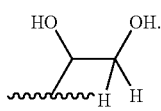

In one embodiment, together with any one of the above and following embodiments, each $R_2$ is independently:

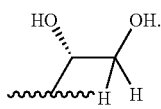

In one embodiment, together with any one of the above and following embodiments, each $R_2$ is independently:

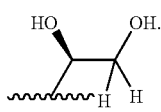

In one embodiment, together with any one of the above and following embodiments, each $R_3$
is independently: —H, $CH_2$—$OR_7$, $(C_1$-$C_6)$alkyl, halo, CN, OH, $NO_2$, or $NH_2$.

In one embodiment, together with any one of the above and following embodiments, each $R_3$ is independently: —H.

In one embodiment, together with any one of the above and following embodiments, each $R_3$ is independently: —$CH_3$.

In one embodiment, together with any one of the above and following embodiments, two $R_3$ groups together form a $(C_2$-$C_6)$bridge, which is unsubstituted or substituted with 1, 2 or 3 independently selected $R_4$ groups, and which bridge optionally contains —HC=CH— within the $(C_2$-$C_6)$bridge.

In one embodiment, together with any one of the above and following embodiments, two $R_3$ groups together form a —$CH_2$—N(Ra)—$CH_2$— bridge, a In one embodiment, together with any one of the above and following embodiments, $R_a$ is —H, $(C_1$-$C_6)$alkyl, $(C_3$-$C_8)$cycloalkyl, —$CH_2$—C(O)—$R_c$, —$CH_2$—C(O)—$OR_c$, —$CH_2$—C(O)—$N(R_c)_2$, —$(CH_2)_2$—O—$R_c$, —$(CH_2)_2$—S(O)_2$—$N(R_c)_2$, or —$(CH_2)_2$—$N(R_c)S(O)_2$—$R_c$.

In one embodiment, together with any one of the above and following embodiments, each $R_b$ is independently: —H, $(C_1$-$C_6)$alkyl, $(C_3$-$C_8)$cycloalkyl, —$N(R_c)_2$, or $N(R_c(C_3$-$C_8)$cycloalkyl.

In one embodiment, together with any one of the above and following embodiments, each $R_b$ is independently: phenyl, pyridyl, or naphthyl, each of which is unsubstituted or substituted with 1, 2 or 3 independently selected $R_7$ groups.

In one embodiment, together with any one of the above and following embodiments, each $R_c$ is independently —H or $(C_1$-$C_4)$alkyl.

In one embodiment, together with any one of the above and following embodiments, each $R_4$ is independently: —$(C_1$-$C_6)$alkyl, $(C_2$-$C_6)$alkenyl, $(C_2$-$C_6)$alkynyl, $(C_3$-$C_8)$cycloalkyl, $(C_5$-$C_8)$cycloalkenyl, or phenyl, each of which is optionally substituted with 1 or 2 hydroxy groups.

In one embodiment, together with any one of the above and following embodiments, each $R_4$ is independently: $(C_1$-$C_6)$alkyl, $(C_2$-$C_6)$alkenyl, $(C_2$-$C_6)$alkynyl, $(C_3$-$C_8)$cycloalkyl, $(C_5$-$C_8)$cycloalkenyl, or phenyl, each of which is substituted with 1 or 2 $R_d$.

In one embodiment, together with any one of the above and following embodiments, each $R_4$ is independently: —H, $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, CH=$NR_7$, $N(R_7)_2$, $NR_7OH$, $OR_7$, $C(O)R_7$, $C(O)OR_7$, $OC(O)OR_7$, $SR_7$, $S(O)R_7$, $S(O)_2R_7$, or —$R_7$.

In one embodiment, together with any one of the above and following embodiments, each $R_4$
is independently: —H.

In one embodiment, together with any one of the above and following embodiments, each $R_d$ is independently: $N(R_7)_2$, $NR_7OH$, $OR_7$, $C(O)R_7$, $C(O)OR_7$, $OC(O)OR_7$, $SR_7$, $S(O)R_7$, $S(O)_2R_7$;

In one embodiment, together with any one of the above and following embodiments, each $R_d$ is independently:

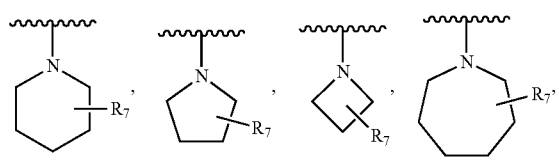

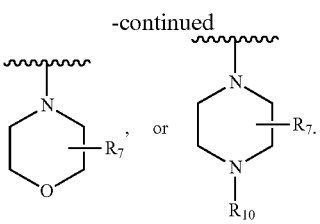

In one embodiment, together with any one of the above and following embodiments, each $R_5$ is independently: —H, halo, $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is optionally substituted with 1 or 2 hydroxy groups.

In one embodiment, together with any one of the above and following embodiments, each $R_5$ is independently: $(C_1-C_6)$alkyl, $(C_2-C_6)$alkenyl, $(C_2-C_6)$alkynyl, $(C_3-C_8)$cycloalkyl, $(C_5-C_3)$cycloalkenyl, or phenyl, each of which is substituted by 1 or 2 substituents independently selected from:

(i) $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, $CH=NR_7$, $N(R_7)_2$, $NR_7OH$, $OR_7$, $C(O)R_7$, $C(O)OR_7$, $OC(O)OR_7$, $SR_7$, $S(O)R_7$, or $S(O)_2R_7$; or (ii)

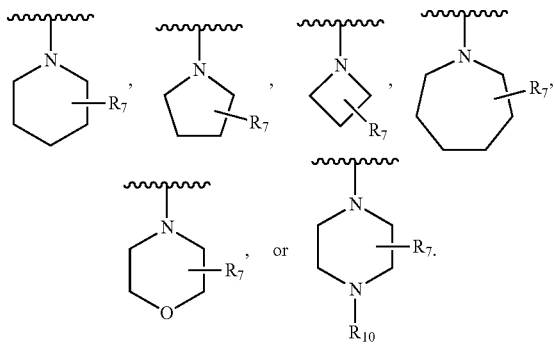

In one embodiment, together with any one of the above and following embodiments, each $R_5$ is independently: —H.

In one embodiment, together with any one of the above and following embodiments, each $R_5$ is independently: $(C_1-C_6)$alkyl.

In one embodiment, together with any one of the above and following embodiments, each $R_5$ is independently: —$CH_3$.

In one embodiment, together with any one of the above and following embodiments, each $R_5$ is independently: —$(C_2-C_6)$alkenyl.

In one embodiment, together with any one of the above and following embodiments, each $R_5$ is independently: —CH=$CH_2$.

In one embodiment, together with any one of the above and following embodiments, in which the two of $R_5$ are —$CH_3$, and another $R_5$ is —CH=$CH_2$.

In one embodiment, together with any one of the above and following embodiments, each $R_7$ is independently: —H, $(C_1-C_6)$alkyl, $(C_2-C_6)$alkenyl, $(C_2-C_6)$alkynyl, $(C_3-C_8)$cycloalkyl, $(C_5-C_8)$cycloalkenyl, phenyl, $(C_1-C_6)$haloalkyl, $(C_1-C_6)$hydroxyalkyl, $(C_1-C_6)$alkoxy$(C_1-C_6)$alkyl, $(C_1-C_6)$alkyl-$N(R_{10})_2$, or $CON(R_{10})_2$.

In one embodiment, together with any one of the above and following embodiments, each $R_{10}$ is independently: —H, $(C_1-C_4)$alkyl, $(C_1-C_4)$haloalkyl, $(C_1-C_4)$hydroxyallyl, or $(C_1-C_4)$alkoxy$(C_1-C_4)$alkyl.

One aspect of the present invention also encompasses compounds of Formula (III) or any pharmaceutically-acceptable salt or hydrate thereof:

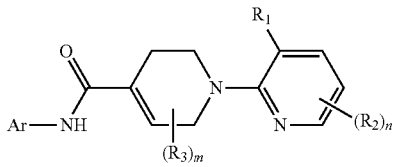

(III)

wherein Ar, $R_1$, $R_2$, $R_3$, m, and n are as defined as above.

In one embodiment, together with any one of the above and following embodiments, Ar is:

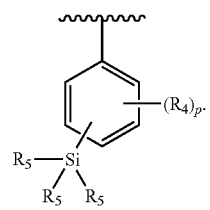

In one embodiment, together with any one of the above and following embodiments, Ar is:

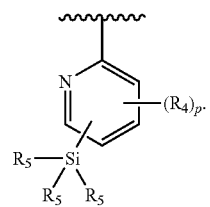

In one embodiment, together with any one of the above and following embodiments, Ar is:

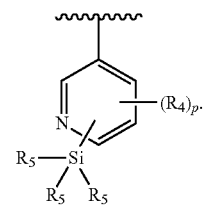

In one embodiment, together with any one of the above and following embodiments, m is 0.

In one embodiment, together with any one of the above and following embodiments, m is 1.

In one embodiment, together with any one of the above and following embodiments, m is 2.

In one embodiment, together with any one of the above and following embodiments, m is 3.

In one embodiment, together with any one of the above and following embodiments, m is 4.

In one embodiment, together with any one of the above and following embodiments, n is 0.

In one embodiment, together with any one of the above and following embodiments, n is 1.

In one embodiment, together with any one of the above and following embodiments, n is 2.

In one embodiment, together with any one of the above and following embodiments, n is 3.

In one embodiment, together with any one of the above and following embodiments, p is 0.

In one embodiment, together with any one of the above and following embodiments, p is 1.

In one embodiment, together with any one of the above and following embodiments, p is 2.

In one embodiment, together with any one of the above and following embodiments, p is 3.

In one embodiment, together with any one of the above and following embodiments, $R_1$ is: —H, -halo, —($C_1$-$C_4$)alkyl, —$NO_2$, —CN, —$NH_2$, —C(halo)$_3$, —CH(halo)$_2$, —$CH_2$(halo), —OC(halo)$_3$, —OCH(halo)$_2$ or —$OCH_2$(halo).

In one embodiment, together with any one of the above and following embodiments, $R_1$ is: -halo.

In one embodiment, together with any one of the above and following embodiments, $R_1$ is: Cl.

In one embodiment, together with any one of the above and following embodiments, $R_1$ is: F.

In one embodiment, together with any one of the above and following embodiments, $R_1$ is: —($C_1$-$C_4$)alkyl.

In one embodiment, together with any one of the above and following embodiments, $R_1$ is: —$CH_3$.

In one embodiment, together with any one of the above and following embodiments, $R_1$ is: —$CF_3$.

In one embodiment, together with any one of the above and following embodiments, each $R_2$ is independently: —H, -halo, —OH, —O($C_1$-$C_4$)alkyl, —CN, —$NO_2$, or —$NH_2$.

In one embodiment, together with any one of the above and following embodiments, each $R_2$ is independently: —H.

In one embodiment, together with any one of the above and following embodiments, each $R_2$ is independently: —($C_1$-$C_{10}$)alkyl, —($C_2$-$C_{10}$)alkenyl, or —($C_2$-$C_{10}$)alkynyl.

In one embodiment, together with any one of the above and following embodiments, each $R_2$ is independently: -phenyl, each of which is unsubstituted or substituted with 1, 2 or 3 independently selected $R_7$ groups.

In one embodiment, together with any one of the above and following embodiments, each $R_2$ is independently: a group of Formula Q; wherein Q is:

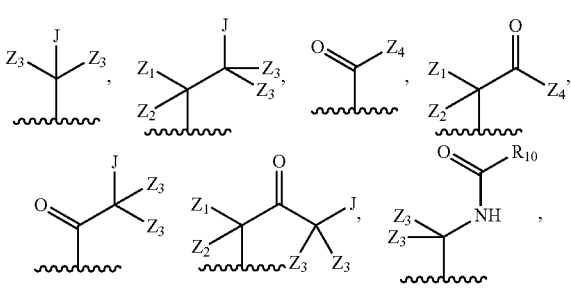

-continued

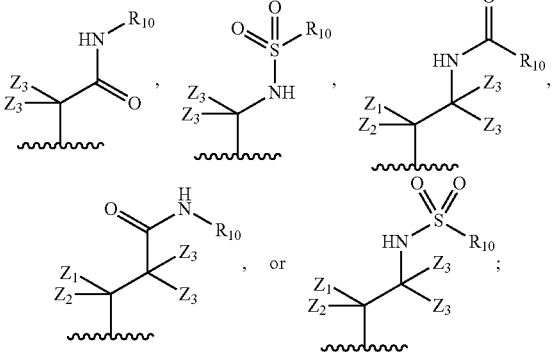

Of which:
$Z_1$ is H, $OR_7$, $SR_7$, $CH_2$—$OR_7$, $CH_2$—$SR_7$, $CH_2$—$N(R_{10})_2$, or halo;
$Z_2$ is H, ($C_1$-$C_6$)alkyl, ($C_2$-$C_6$)alkenyl, ($C_2$-$C_6$)alkynyl, $CH_2$—$OR_7$, phenyl, or halo;
Each $Z_3$ is independently H, ($C_1$-$C_6$)alkyl, ($C_2$-$C_6$)alkenyl, ($C_2$-$C_6$)alkynyl, or phenyl;
$Z_1$ is H, OH, $OR_{10}$, ($C_1$-$C_6$)alkyl, or $N(R_{10})_2$;
J is $OR_{10}$$SR_{10}$, $N(R_{10})_2$ or CN;

In one embodiment, together with any one of the above and following embodiments, each $R_2$ is independently: —H.

In one embodiment, together with any one of the above and following embodiments, each $R_2$ is independently:

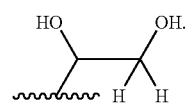

In one embodiment, together with any one of the above and following embodiments, each $R_2$ is independently:

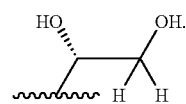

In one embodiment, together with any one of the above and following embodiments, each $R_2$ is independently:

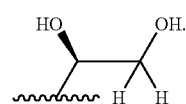

In one embodiment, together with any one of the above and following embodiments, each $R_3$ is independently: —H, $CH_2$—$OR_7$, ($C_1$-$C_6$)alkyl, halo, CN, OH, $NO_2$, or $NH_2$.

In one embodiment, together with any one of the above and following embodiments, each $R_3$ is independently: —H.

In one embodiment, together with any one of the above and following embodiments, each $R_3$ is independently: —$CH_3$.

In one embodiment, together with any one of the above and following embodiments, two $R_3$ groups together form a ($C_2$-$C_6$)bridge, which is unsubstituted or substituted with 1, 2 or 3 independently selected R₄ groups, and which bridge optionally contains —HC═CH— within the (C₂-C₆)bridge.

In one embodiment, together with any one of the above and following embodiments, two R₃ groups together form a —CH₂—N(Ra)—CH₂— bridge, a

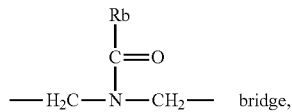

bridge, or a

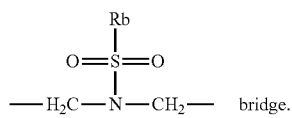

bridge.

In one embodiment, together with any one of the above and following embodiments, R$_a$ is —H, (C₁-C₆)alkyl, (C₃-C₈)cycloalkyl, —CH₂—C(O)—R$_c$, —CH₂—C(O)—OR$_c$, —CH₂—C(O)—N(R$_c$)₂, —(CH₂)₂—O—R$_c$, —(CH₂)₂—S(O)₂—N(R$_c$)₂, or —(CH₂)₂—N(R)S(O)₂—R$_c$.

In one embodiment, together with any one of the above and following embodiments, each R$_b$ is independently: —H, (C₁-C₆)alkyl, (C₃-C₈)cycloalkyl, —N(R$_c$)₂, or N(R$_c$)—(C₃-C₈)cycloalkyl.

In one embodiment, together with any one of the above and following embodiments, each R$_b$ is independently: phenyl, pyridyl, or naphthyl, each of which is unsubstituted or substituted with 1, 2 or 3 independently selected R₇ groups.

In one embodiment, together with any one of the above and following embodiments, each R$_d$ is independently —H or (C₁-C₄)alkyl.

In one embodiment, together with any one of the above and following embodiments, each R₄ is independently: (C₁-C₆)alkyl, (C₂-C₆)alkenyl, (C₂-C₆)alkynyl, (C₃-C₈)cycloalkyl, (C₅-C₈)cycloalkenyl, or phenyl, each of which is optionally substituted with 1 or 2 hydroxy groups.

In one embodiment, together with any one of the above and following embodiments, each R₄ is independently: (C₁-C₆)alkyl, (C₂-C₆)alkenyl, (C₂-C₆)alkynyl, (C₃-C₈)cycloalkyl, (C₅-C₈)cycloalkenyl, or phenyl, each of which is substituted with 1 or 2 R$_d$.

In one embodiment, together with any one of the above and following embodiments, each R₄ is independently: —H, CH₂C(halo)₃, C(halo)₃, CH(halo)₂, CH₂(halo), OC(halo)₃, OCH(halo)₂, OCH₂(halo), SC(halo)₃, SCH(halo)₂, SCH₂(halo), CN, OH, halo, N₃, NO₂, NH₂, CH═NR₇, N(R₇)₂, NR₇OH, OR₇, C(O)R₇, C(O)OR₇, OC(O)OR₇, SR₇, S(O)R₇, S(O)₂R₇, or —R₇.

In one embodiment, together with any one of the above and following embodiments, each R₄ is independently: —H.

In one embodiment, together with any one of the above and following embodiments, each R$_d$ is independently: N(R₇)₂, NR₇OH, OR₇, C(O)R₇, C(O)OR₇, OC(O)OR₇, SR₇, S(O)R₇, S(O)₂R₇;

In one embodiment, together with any one of the above and following embodiments, each R$_d$ is independently:

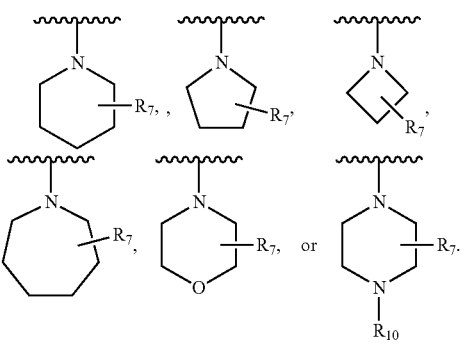

In one embodiment, together with any one of the above and following embodiments, each R₅ is independently: —H, halo, (C₁-C₆)alkyl, (C₂-C₆)alkenyl, (C₂-C₆)alkynyl, (C₃-C₈)cycloalkyl, (C₅-C₈)cycloalkenyl, or phenyl, each of which is optionally substituted with 1 or 2 hydroxy groups.

In one embodiment, together with any one of the above and following embodiments, each R₅ is independently: (C₁-C₆)alkyl, (C₂-C₆)alkenyl, (C₂-C₆)alkynyl, (C₃-C₈)cycloalkyl, (C₅-C₈)cycloalkenyl, or phenyl, each of which is substituted by 1 or 2 substituents independently selected from:
(i) CH₂C(halo)₃, C(halo)₃, CH(halo)₂, CH₂(halo), OC(halo)₃, OCH(halo)₂, OCH₂(halo), SC(halo)₃, SCH(halo)₂, SCH₂(halo), CN, OH, halo, N₃, NO₂, NH₂, CH═NR₇, N(R₇)₂, NR₇OH, OR₇, C(O)R₇, C(O)OR₇, OC(O)OR₇, SR₇, S(O)R₇, or S(O)₂R₇; or
(ii)

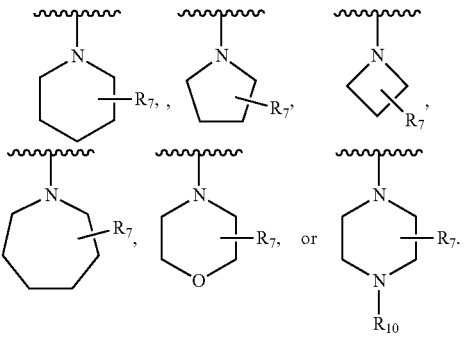

In one embodiment, together with any one of the above and following embodiments, each R₅ is independently: (C₁-C₆)alkyl.

In one embodiment, together with any one of the above and following embodiments, each R₅ is independently: —CH₃.

In one embodiment, together with any one of the above and following embodiments, each R₅ is independently: —(C₂-C₆)alkenyl.

In one embodiment, together with any one of the above and following embodiments, each R₅ is independently: —CH═CH₂.

In one embodiment, together with any one of the above and following embodiments, in which the two of R₅ are —CH₃, and another R₅ is —CH═CH₂.

In one embodiment, together with any one of the above and following embodiments, each R₇ is independently: —H, (C₁-C₆)alkyl, (C₂-C₆)alkenyl, (C₂-C₆)alkynyl, (C₃-C₈)cycloalkyl, (C₅-C₈)cycloalkenyl, phenyl, (C₁-C₆)haloalkyl, (C₁-C₆)hydroxyalkyl, (C₁-C₆)alkoxy(C₁-C₆)alkyl, (C₁-C₆)alkyl-N(R₁₀)₂, or CON(R₁₀)₂.

In one embodiment, together with any one of the above and following embodiments, each $R_{10}$ is independently: —H, $(C_1-C_4)$alkyl, $(C_1-C_4)$haloalkyl, $(C_1-C_4)$hydroxyalkyl, or $(C_1-C_4)$alkoxy$(C_1-C_4)$alkyl.

One aspect of the present invention also encompasses compounds of Formula (VIII) or any pharmaceutically-acceptable salt or hydrate thereof:

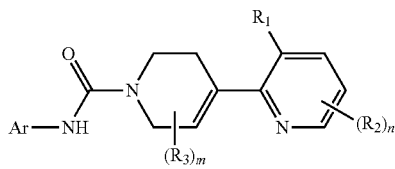

(VIII)

wherein Ar, $R_1$, $R_2$, $R_3$, m, and n are as defined as above.

In one embodiment, together with any one of the above and following embodiments, Ar is:

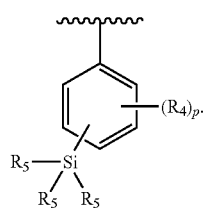

In one embodiment, together with any one of the above and following embodiments, Ar is:

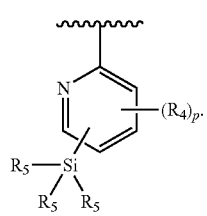

In one embodiment, together with any one of the above and following embodiments, Ar is:

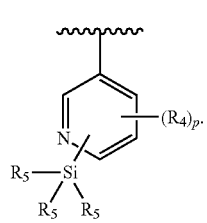

In one embodiment, together with any one of the above and following embodiments, m is 0.

In one embodiment, together with any one of the above and following embodiments, m is 1.

In one embodiment, together with any one of the above and following embodiments, m is 2.

In one embodiment, together with any one of the above and following embodiments, m is 3.

In one embodiment, together with any one of the above and following embodiments, m is 4.

In one embodiment, together with any one of the above and following embodiments, n is 0.

In one embodiment, together with any one of the above and following embodiments, n is 1.

In one embodiment, together with any one of the above and following embodiments, n is 2.

In one embodiment, together with any one of the above and following embodiments, n is 3.

In one embodiment, together with any one of the above and following embodiments, p is 0.

In one embodiment, together with any one of the above and following embodiments, p is 1.

In one embodiment, together with any one of the above and following embodiments, p is 2.

In one embodiment, together with any one of the above and following embodiments, p is 3.

In one embodiment, together with any one of the above and following embodiments, $R_1$ is: —H, -halo, —$(C_1-C_4)$alkyl, —$NO_2$, —CN, —$NH_2$, —C(halo)$_3$, —CH(halo)$_2$, —CH$_2$(halo), —OC(halo)$_3$, —OCH(halo)$_2$ or —OCH$_2$(halo).

In one embodiment, together with any one of the above and following embodiments, $R_1$ is: -halo.

In one embodiment, together with any one of the above and following embodiments, $R_1$ is: Cl.

In one embodiment, together with any one of the above and following embodiments, $R_1$ is: F.

In one embodiment, together with any one of the above and following embodiments, $R_1$ is: —$(C_1-C_4)$ In one embodiment, together with any one of the above and following embodiments, In one embodiment, together with any one of the above and following embodiments, $R_1$ is: —$CF_3$.

In one embodiment, together with any one of the above and following embodiments, each $R_2$ is independently: —H, -halo, —OH, —O$(C_1-C_4)$alkyl, —CN, —$NO_2$, or —$NH_2$.

In one embodiment, together with any one of the above and following embodiments, each $R_2$ is independently: —H.

In one embodiment, together with any one of the above and following embodiments, each $R_2$ is independently: —$(C_1-C_{10})$alkyl, —$(C_2-C_{10})$alkenyl, or —$(C_2-C_{10})$alkynyl.

In one embodiment, together with any one of the above and following embodiments, each $R_2$ is independently: -phenyl, each of which is unsubstituted or substituted with 1, 2 or 3 independently selected $R_7$ groups.

In one embodiment, together with any one of the above and following embodiments, each $R_2$ is independently: a group of Formula Q; wherein Q is:

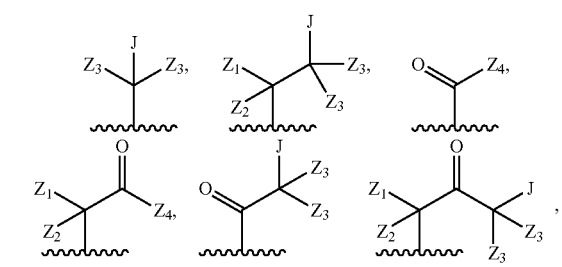

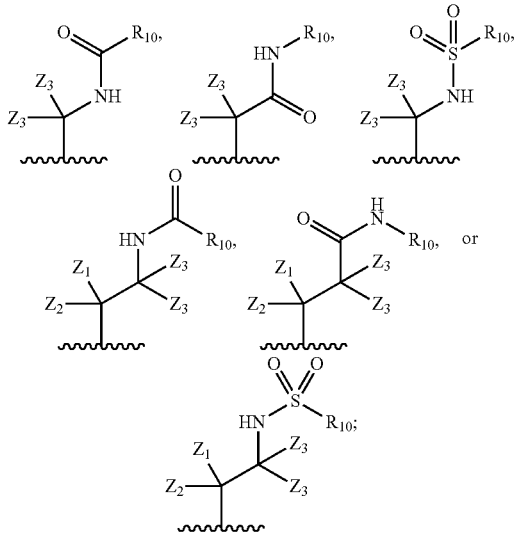

Of which:
$Z_1$ is H, $OR_7$, $SR_7$, $CH_2$—$OR_7$, $CH_2$—$SR_7$, $CH_2$—$N(R_{10})_2$, or halo;
$Z_2$ is H, $(C_1$-$C_6)$alkyl, $(C_2$-$C_6)$alkenyl, $(C_2$-$C_6)$alkynyl, $CH_2$—$OR_7$, phenyl, or halo;
Each $Z_3$ is independently H, $(C_1$-$C_6)$alkyl, $(C_2$-$C_6)$alkenyl, $(C_2$-$C_6)$alkynyl, or phenyl;
$Z_4$ is H, OH, $OR_{10}$, $(C_1$-$C_6)$alkyl, or $N(R_{10})_2$;
J is $OR_{10}$, $SR_{10}$, $N(R_{10})_2$ or CN;

In one embodiment, together with any one of the above and following embodiments, each $R_2$ is independently: —H.

In one embodiment, together with any one of the above and following embodiments, each $R_2$ is independently:

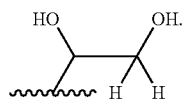 [SMILES: *C(O)CO]

In one embodiment, together with any one of the above and following embodiments, each $R_2$ is independently:

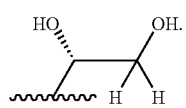

In one embodiment, together with any one of the above and following embodiments, each $R_2$ is independently:

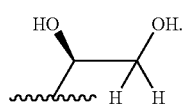 [SMILES: *[C@@H](O)CO]

In one embodiment, together with any one of the above and following embodiments, each $R_3$ is independently: —H, $CH_2$—$OR_2$, $(C_1$-$C_6)$alkyl, halo, CN, OH, $NO_2$, or $NH_2$.

In one embodiment, together with any one of the above and following embodiments, each $R_3$ is independently: —H.

In one embodiment, together with any one of the above and following embodiments, each $R_3$ is independently: —$CH_3$.

In one embodiment, together with any one of the above and following embodiments, two $R_3$ groups together form a $(C_2$-$C_6)$bridge, which is unsubstituted or substituted with 1, 2 or 3 independently selected $R_4$ groups, and which bridge optionally contains —HC=CH— within the $(C_2$-$C_6)$bridge.

In one embodiment, together with any one of the above and following embodiments, two $R_3$ groups together form a —$CH_2$—N(Ra)—$CH_2$— bridge, a

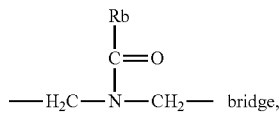

or a

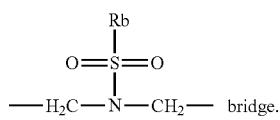

In one embodiment, together with any one of the above and following embodiments, $R_a$ is —H, $(C_1$-$C_6)$alkyl, $(C_3$-$C_8)$cycloalkyl, —$CH_2$—C(O)$R_c$, —$CH_2$—C(O)—$R_c$, —$CH_2$—C(O)—N($R_c$)$_2$, —$(CH_2)_2$—O—$R_c$, —$(CH_2)_2$—S(O)$_2$—N($R_c$)$_2$, or —$(CH_2)_2$—N($R_c$)S(O)$_2$—$R_c$.

In one embodiment, together with any one of the above and following embodiments, each $R_b$ is independently: —H, $(C_1$-$C_6)$alkyl, $(C_3$-$C_8)$cycloalkyl, —N($R_c$)$_2$, or N($R_c$)—$(C_3$-$C_8)$cycloalkyl.

In one embodiment, together with any one of the above and following embodiments, each $R_b$ is independently: phenyl, pyridyl, or naphthyl, each of which is unsubstituted or substituted with 1, 2 or 3 independently selected $R_7$ groups.

In one embodiment, together with any one of the above and following embodiments, each $R_c$ is independently —H or $(C_1$-$C_4)$alkyl.

In one embodiment, together with any one of the above and following embodiments, each $R_4$ is independently: $(C_1$-$C_6)$alkyl, $(C_2$-$C_6)$alkenyl, $(C_2$-$C_6)$alkynyl, $(C_3$-$C_8)$cycloalkyl, $(C_5$-$C_8)$cycloalkenyl, or phenyl, each of which is optionally substituted with 1 or 2 hydroxy groups.

In one embodiment, together with any one of the above and following embodiments, each $R_4$ is independently: $(C_1$-$C_6)$alkyl, $(C_2$-$C_6)$alkenyl, $(C_2$-$C_6)$alkynyl, $(C_3$-$C_8)$cycloalkyl, $(C_5$-$C_8)$cycloalkenyl, or phenyl, each of which is substituted with 1 or 2 $R_d$.

In one embodiment, together with any one of the above and following embodiments, each $R_4$ is independently: —H, $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, CH=$NR_7$, $N(R_7)_2$, $NR_7OH$, $OR_7$, $C(O)R_7$, $C(O)OR_7$, $OC(O)OR_7$, $SR_7$, $S(O)R_7$, $S(O)_2R_7$, or —$R_7$.

In one embodiment, together with any one of the above and following embodiments, each $R_4$ is independently: —H.

In one embodiment, together with any one of the above and following embodiments, each $R_d$ is independently: $N(R_7)_2$, $NR_7OH$, $OR_7$, $C(O)R_7$, $C(O)OR_7$, $OC(O)OR_7$, $SR_7$, $S(O)R_7$, $S(O)_2R_7$;

In one embodiment, together with any one of the above and following embodiments, each $R_d$ is independently:

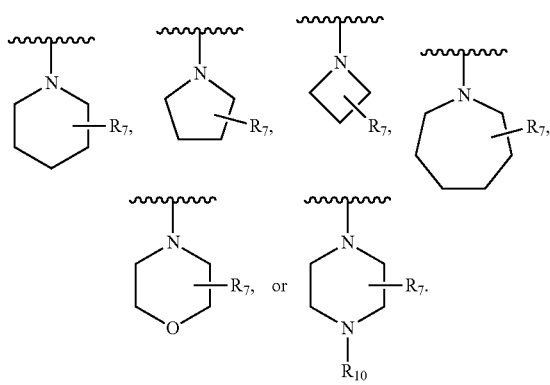

In one embodiment, together with any one of the above and following embodiments, each $R_5$ is independently: —H, halo, $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is optionally substituted with 1 or 2 hydroxy groups.

In one embodiment, together with any one of the above and following embodiments, each $R_5$ is independently: $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is substituted by 1 or 2 substituents independently selected from:
(i) $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, $CH=NR_7$, $N(R_7)_2$, $NR_7OH$, $OR_7$, $C(O)R_7$, $C(O)OR_7$, $OC(O)OR_7$, $SR_7$, $S(O)R_7$, or $S(O)_2R_7$; or
(ii)

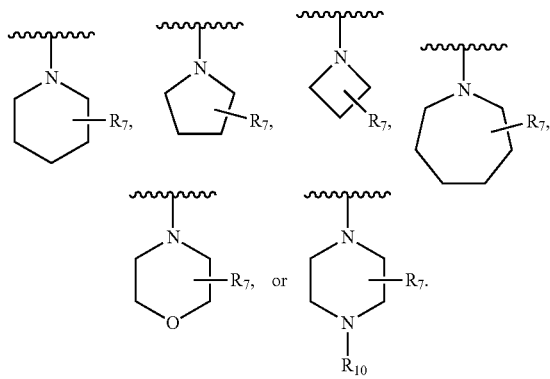

In one embodiment, together with any one of the above and following embodiments, each $R_5$ is independently: $(C_1-C_6)$ alkyl.

In one embodiment, together with any one of the above and following embodiments, each $R_5$ is independently: —$CH_3$.

In one embodiment, together with any one of the above and following embodiments, each $R_5$ is independently: —$(C_2-C_6)$ alkenyl.

In one embodiment, together with any one of the above and following embodiments, each $R_5$ is independently: —$CH=CH_2$.

In one embodiment, together with any one of the above and following embodiments, in which the two of $R_5$ are —$CH_3$, and another $R_5$ is —$CH=CH_2$.

In one embodiment, together with any one of the above and following embodiments, each $R_7$ is independently: —H, $(C_2-C_6)$alkenyl, $(C_2-C_6)$alkynyl, $(C_3-C_8)$cycloalkyl, $(C_5-C_8)$cycloalkenyl, phenyl, $(C_1-C_6)$haloalkyl, $(C_1-C_6)$hydroxyallyl, $(C_1-C_6)$alkoxy$(C_1-C_6)$alkyl, $(C_1-C_6)$alkyl-$N(R_{10})_2$, or $CON(R_{10})_2$.

In one embodiment, together with any one of the above and following embodiments, each $R_{10}$ is independently: —H, $(C_1-C_4)$alkyl, $(C_1-C_4)$haloalkyl, $(C_1-C_4)$hydroxyalkyl, or $(C_1-C_4)$alkoxy$(C_1-C_4)$alkyl.

One aspect of the present invention also encompasses compounds of Formula (IX) or any pharmaceutically-acceptable salt or hydrate thereof:

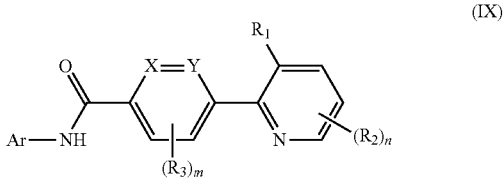

(IX)

wherein Ar, $R_1$, $R_2$, $R_3$, m, and n are as defined as above.

In one embodiment, together with any one of the above and following embodiments, each X is independently N.

In one embodiment, together with any one of the above and following embodiments, each X is independently C.

In one embodiment, together with any one of the above and following embodiments, each Y is independently N.

In one embodiment, together with any one of the above and following embodiments, each Y is independently C.

In one embodiment, together with any one of the above and following embodiments, Ar

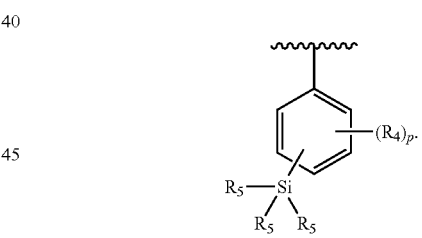

In one embodiment, together with any one of the above and following embodiments, Ar is:

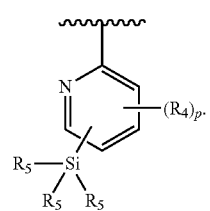

In one embodiment, together with any one of the above and following embodiments, Ar is:

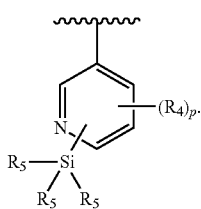

In one embodiment, together with any one of the above and following embodiments, m is 0.

In one embodiment, together with any one of the above and following embodiments, m is 1.

In one embodiment, together with any one of the above and following embodiments, m is 2.

In one embodiment, together with any one of the above and following embodiments, m is 3.

In one embodiment, together with any one of the above and following embodiments, m is 4.

In one embodiment, together with any one of the above and following embodiments, n is 0.

In one embodiment, together with any one of the above and following embodiments, n is 1.

In one embodiment, together with any one of the above and following embodiments, n is 2.

In one embodiment, together with any one of the above and following embodiments, n is 3.

In one embodiment, together with any one of the above and following embodiments, p is 0.

In one embodiment, together with any one of the above and following embodiments, p is 1.

In one embodiment, together with any one of the above and following embodiments, p is 2.

In one embodiment, together with any one of the above and following embodiments, p is 3.

In one embodiment, together with any one of the above and following embodiments, $R_1$ is: —H, -halo, —($C_1$-$C_4$)alkyl, —$NO_2$, —CN, —$NH_2$, —C(halo)$_3$, —CH(halo)$_2$, —$CH_2$(halo), —OC(halo)$_3$, —OCH(halo)$_2$ or —$OCH_2$(halo).

In one embodiment, together with any one of the above and following embodiments, $R_1$ is: -halo.

In one embodiment, together with any one of the above and following embodiments, $R_1$ is: Cl.

In one embodiment, together with any one of the above and following embodiments, $R_1$ is: F.

In one embodiment, together with any one of the above and following embodiments, $R_1$ s: —($C_1$-$C_4$)alkyl.

In one embodiment, together with any one of the above and following embodiments, $R_1$ is: —$CH_3$.

In one embodiment, together with any one of the above and following embodiments, $R_1$ is: —$CF_3$.

In one embodiment, together with any one of the above and following embodiments, each $R_2$ is independently: —H, -halo, —OH, —O($C_1$-$C_4$)alkyl, —CN, —$NO_2$, or —$NH_2$.

In one embodiment, together with any one of the above and following embodiments, each $R_2$ is independently: —H.

In one embodiment, together with any one of the above and following embodiments, each $R_2$ is independently: —($C_1$-$C_{10}$)alkyl, —($C_2$-$C_{10}$)alkenyl, or —($C_2$-$C_{10}$)alkynyl.

In one embodiment, together with any one of the above and following embodiments, each $R_2$ is independently: -phenyl, each of which is unsubstituted or substituted with 1, 2 or 3 independently selected $R_7$ groups.

In one embodiment, together with any one of the above and following embodiments, each $R_2$ is independently: a group of Formula Q; wherein Q is:

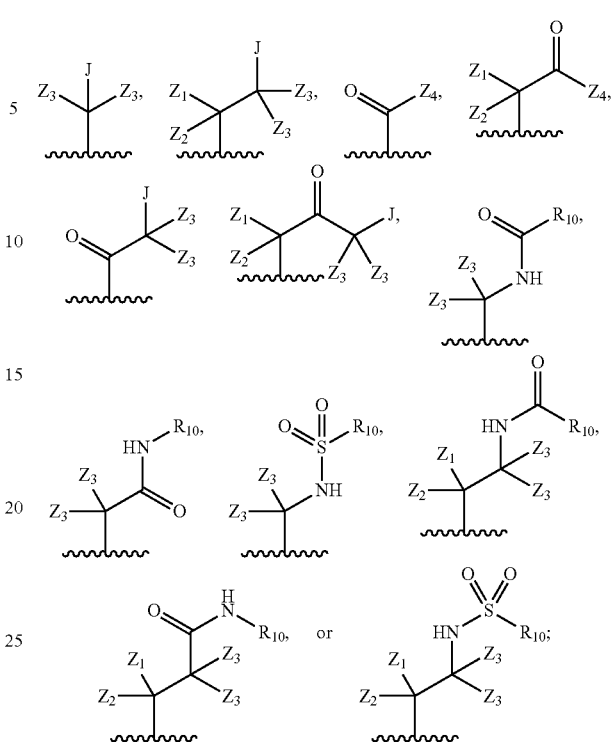

Of which:

$Z_1$ is H, $OR_7$, $SR_7$, $CH_2$—$OR_7$, $CH_2$—$SR_7$, $CH_2$—$N(R_{10})_2$, or halo;

$Z_2$ is H, ($C_1$-$C_6$)alkyl, ($C_2$-$C_6$)alkenyl, ($C_2$-$C_6$)alkynyl, $CH_2$—$OR_7$, phenyl, or halo;

Each $Z_3$ is independently H, ($C_1$-$C_6$)alkyl, ($C_2$-$C_6$)alkenyl, ($C_2$-$C_6$)alkynyl, or phenyl;

$Z_4$ is H, OH, $OR_{10}$, ($C_1$-$C_6$)alkyl, or $N(R_{10})_2$;

J is $OR_{to}$, $SR_{10}$, $N(R_{10})_2$ or CN;

In one embodiment, together with any one of the above and following embodiments, each $R_2$ is independently: —H.

In one embodiment, together with any one of the above and following embodiments, each $R_2$ is independently:

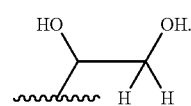

In one embodiment, together with any one of the above and following embodiments, each $R_2$ is independently:

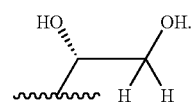

In one embodiment, together with any one of the above and following embodiments, each $R_2$ is independently:

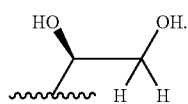

In one embodiment, together with any one of the above and following embodiments, each $R_3$ is independently: —H, $CH_2$—$OR_7$, $(C_1-C_6)$alkyl, halo, CN, OH, $NO_2$, or $NH_2$.

In one embodiment, together with any one of the above and following embodiments, each $R_3$ is independently: —H.

In one embodiment, together with any one of the above and following embodiments, each $R_3$ is independently: —$CH_3$.

In one embodiment, together with any one of the above and following embodiments, two $R_3$ groups together form a $(C_2-C_6)$bridge, which is unsubstituted or substituted with 1, 2 or 3 independently selected $R_4$ groups, and which bridge optionally contains —HC=CH— within the $(C_2-C_6)$bridge.

In one embodiment, together with any one of the above and following embodiments, two $R_3$ groups together form a —$CH_2$—N(Ra)—$CH_2$— bridge, a

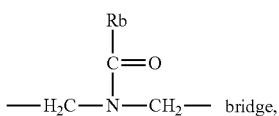

or a

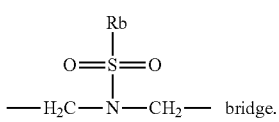

In one embodiment, together with any one of the above and following embodiments, $R_a$ is —H, $(C_1-C_6)$alkyl, $(C_3-C_8)$cycloalkyl, —$CH_2$—C(O)—$R_c$, —$CH_2$—C(O)—$OR_c$, —$CH_2$—C(O)—N$(R_c)_2$, —$(CH_2)_2$—O—$R_c$, —$(CH_2)_2$—S$(O)_2$—N$(R_c)_2$, or —$(CH_2)_2$—N$(R_c)$S$(O)_2$—$R_c$.

In one embodiment, together with any one of the above and following embodiments, each $R_b$ is independently: —H, $(C_1-C_6)$alkyl, $(C_3-C_8)$cycloalkyl, —N$(R_c)_2$, or N$(R_c)$—$(C_3-C_8)$cycloalkyl.

In one embodiment, together with any one of the above and following embodiments, each $R_b$ is independently: phenyl, pyridyl, or naphthyl, each of which is unsubstituted or substituted with 1, 2 or 3 independently selected $R_7$ groups.

In one embodiment, together with any one of the above and following embodiments, each $R_c$ is independently —H or $(C_1-C_4)$alkyl.

In one embodiment, together with any one of the above and following embodiments, each $R_4$ is independently: $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is optionally substituted with 1 or 2 hydroxy groups.

In one embodiment, together with any one of the above and following embodiments, each $R_4$ is independently: $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is substituted with 1 or 2 $R_d$.

In one embodiment, together with any one of the above and following embodiments, each $R_4$ is independently: —H, $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, CH=$NR_7$, $N(R_7)_2$, $NR_7OH$, $OR_7$, $C(O)R_7$, $C(O)OR_7$, $OC(O)OR_7$, $SR_7$, $S(O)R_7$, $S(O)_2R_7$, or —$R_7$.

In one embodiment, together with any one of the above and following embodiments, each $R_4$ is independently: —H.

In one embodiment, together with any one of the above and following embodiments, each $R_d$ is independently: $N(R_7)_2$, $NR_7OH$, $OR_7$, $C(O)R_7$, $C(O)OR_7$, $OC(O)OR_7$, $SR_7$, $S(O)R_7$, $S(O)_2R_7$;

In one embodiment, together with any one of the above and following embodiments, each $R_d$ is independently:

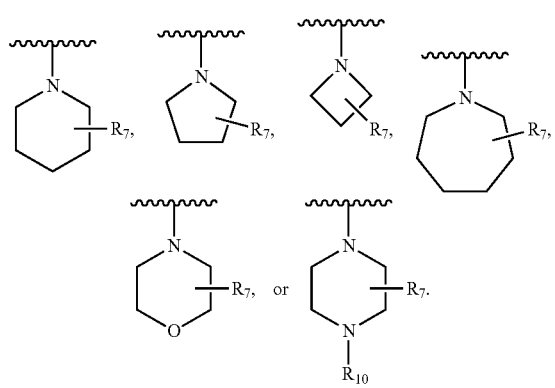

In one embodiment, together with any one of the above and following embodiments, each $R_5$ is independently: —H, halo, $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is optionally substituted with 1 or 2 hydroxy groups.

In one embodiment, together with any one of the above and following embodiments, each $R_5$ is independently: $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is substituted by 1 or 2 substituents independently selected from:

(i) $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, CH=$NR_7$, $N(R_7)_2$, $NR_7OH$, $OR_7$, $C(O)R_7$, $C(O)OR_7$, $OC(O)OR_7$, $SR_7$, $S(O)R_7$, or $S(O)_2R_7$; or (ii)

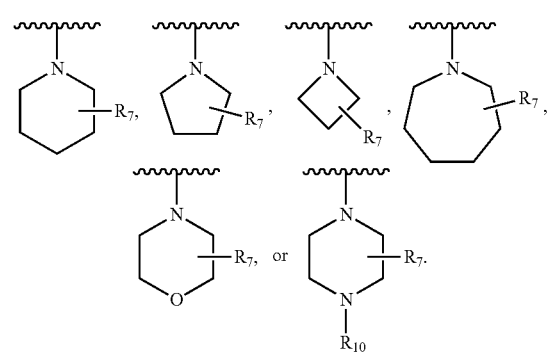

In one embodiment, together with any one of the above and following embodiments, each $R_5$ is independently: $(C_1-C_6)$alkyl.

In one embodiment, together with any one of the above and following embodiments, each $R_5$ is independently: —$CH_3$.

In one embodiment, together with any one of the above and following embodiments, each $R_5$ is independently: —($C_2$-$C_6$) alkenyl.

In one embodiment, together with any one of the above and following embodiments, each $R_5$ is independently: —CH=CH$_2$.

In one embodiment, together with any one of the above and following embodiments, in which the two of $R_5$ are —CH$_3$, and another $R_5$ is —CH=CH$_2$.

In one embodiment, together with any one of the above and following embodiments, each $R_7$ is independently: —H, ($C_1$-$C_6$)alkyl, ($C_2$-$C_6$)alkenyl, ($C_2$-$C_6$)alkynyl, ($C_3$-$C_8$)cycloalkyl, ($C_5$-$C_8$)cycloalkenyl, phenyl, ($C_1$-$C_6$)haloalkyl, ($C_1$-$C_6$)hydroxyalkyl, ($C_1$-$C_6$)alkoxy($C_1$-$C_6$)alkyl, ($C_1$-$C_6$) alkyl-N($R_{10}$)$_2$, or CON($R_{10}$)$_2$.

In one embodiment, together with any one of the above and following embodiments, each $R_{10}$ is independently: —H, ($C_1$-$C_4$)alkyl, ($C_1$-$C_4$)haloalkyl, ($C_1$-$C_4$)hydroxyalkyl, or ($C_1$-$C_4$)alkoxy($C_1$-$C_4$)alkyl.

One aspect of the present invention also encompasses compounds of Formula (V) or any pharmaceutically-acceptable salt or hydrate thereof:

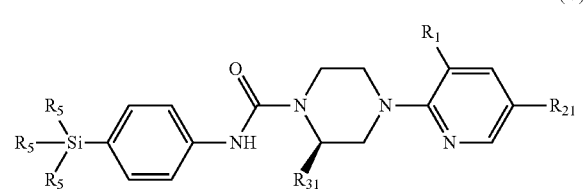
(V)

Wherein:
$R_1$ is -halo, —CH$_3$, or —CF$_3$.
$R_{21}$ is —H, or

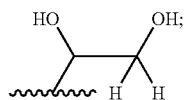

wherein

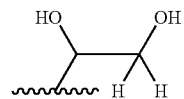

can be

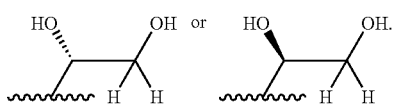

$R_{31}$ is —H or, —CH$_3$.
each $R_5$ is independently:
(a) —H, halo, ($C_1$-$C_6$)alkyl, ($C_2$-$C_6$)alkenyl, ($C_2$-$C_6$)alkynyl, ($C_3$-$C_8$)cycloalkyl, ($C_5$-$C_8$)cycloalkenyl, or phenyl, each of which is optionally substituted with 1 or 2 hydroxy groups; or
(b) ($C_1$-$C_6$)alkyl, ($C_2$-$C_6$)alkenyl, ($C_2$-$C_6$)alkynyl, ($C_3$-$C_8$) cycloalkyl, ($C_5$-$C_8$)cycloalkenyl, or phenyl, each of which is substituted by 1 or 2 substituents independently selected from:
(i) CH$_2$C(halo)$_3$, C(halo)$_3$, CH(halo)$_2$, CH$_2$(halo), OC(halo)$_3$, OCH(halo)$_2$, OCH$_2$(halo), SC(halo)$_3$, SCH(halo)$_2$, SCH$_2$(halo), CN, OH, halo, N$_3$, NO$_2$, NH$_2$, CH=NR$_7$, N(R$_7$)$_2$, NR$_7$OH, OR$_7$, C(O)R$_7$, C(O)OR$_7$, OC(O)OR$_7$, SR$_7$, S(O)R$_7$, or S(O)$_2$R$_7$; or
(ii)

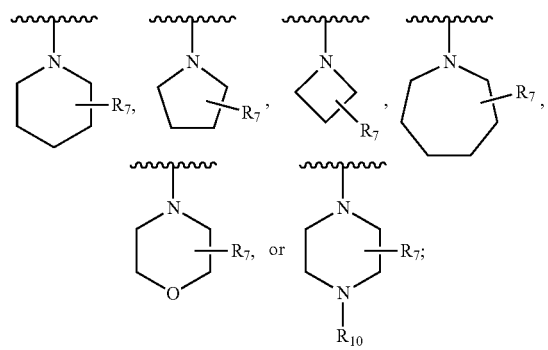

In one embodiment, $R_1$ of Formula (V) is: -halo.
In one embodiment, $R_1$ of Formula (V) is: —F.
In one embodiment, $R_1$, of Formula (V) is: —Cl.
In one embodiment, $R_1$ of Formula (V) is: —CH$_3$.
In one embodiment, $R_1$ of Formula (V) is: —CF$_3$.
In one embodiment, $R_{21}$ of Formula (V) is: —H.
In one embodiment, $R_{21}$ of Formula (V) is:

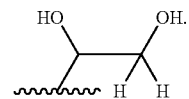

In one embodiment, $R_{21}$ of Formula (V) is:

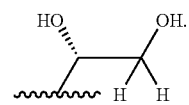

In one embodiment, $R_{21}$ of Formula (V) is:

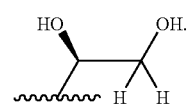 [SMILES: *[C@@H](O)CO]

In one embodiment, $R_{31}$ of Formula (V) is: —H.
In one embodiment, $R_{31}$ of Formula (V) is: —CH$_3$.

In one embodiment, each $R_5$ of Formula (V) is independently: —H, halo, ($C_1$-$C_6$)alkyl, ($C_2$-$C_6$)alkenyl, ($C_2$-$C_6$) alkynyl, ($C_3$-$C_8$)cycloalkyl, ($C_5$-$C_8$)cycloalkenyl, or phenyl, each of which is optionally substituted with 1 or 2 hydroxy groups.

In one embodiment, each $R_5$ of Formula (V) is independently: ($C_1$-$C_6$)alkyl, ($C_2$-$C_6$)alkenyl, ($C_2$-$C_6$)alkynyl, ($C_3$-$C_8$)cycloalkyl, ($C_5$-$C_8$)cycloalkenyl, or phenyl, each of which is substituted by 1 or 2 substituents independently selected from:
(i) CH$_2$C(halo)$_3$, C(halo)$_3$, CH(halo)$_2$, CH$_2$(halo), OC(halo)$_3$, OCH(halo)$_2$, OCH$_2$(halo), SC(halo)$_3$, SCH(halo)$_2$, SCH$_2$(halo), CN, OH, halo, N$_3$, NO$_2$, NH$_2$, CH=NR$_7$, N(R$_7$)$_2$, NR$_7$OH, OR$_7$, C(O)R$_7$, C(O)OR$_7$, OC(O)OR$_7$, SR$_7$, S(O)R$_7$, or S(O)$_2$R$_7$; or (ii)

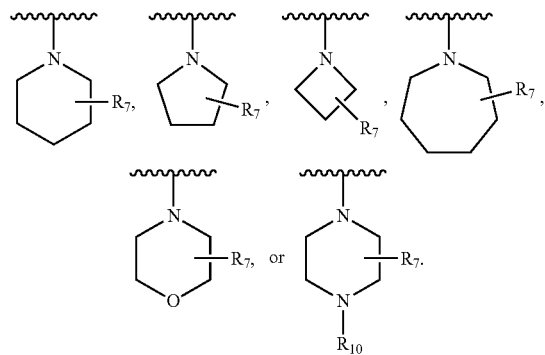

In one embodiment, each R$_5$ of Formula (V) is independently: —H.

In one embodiment, each R$_5$ of Formula (V) is independently: (C$_1$-C$_6$)alkyl.

In one embodiment, each R$_5$ of Formula (V) is independently: —CH$_3$.

In one embodiment, of Formula (V) R$_1$ is —F; R$_{31}$ is —H; R$_{21}$ is —H; R$_5$ is —CH$_3$.

In one embodiment, of Formula (V) R$_1$ is —F; R$_{31}$ is —H; R$_{21}$ is

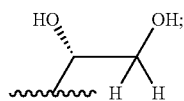

R$_5$ is —CH$_3$.

In one embodiment, of Formula (V) R$_1$ is —F; R$_{31}$ is —H; R$_{21}$ is

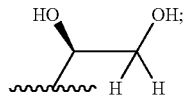

R$_5$ is —CH$_3$.

In one embodiment, of Formula (V) R$_1$ is —Cl; R$_{31}$ is —H; R$_{21}$ is —H; R$_5$ is —CH$_3$.

In one embodiment, of Formula (V) R$_1$ is —Cl; R$_{31}$ is —H; R$_{21}$ is

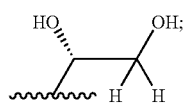

R$_5$ is —CH$_3$.

In one embodiment, of Formula (V) R$_1$ is —Cl; R$_{31}$ is —H; R$_{21}$ is

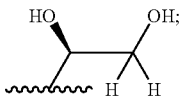 [SMILES: *[C@@H](O)CO]

R$_5$ is —CH$_3$.

In one embodiment, of Formula (V) R$_1$ is —CF$_3$; R$_{31}$ is —H; R$_{21}$ is —H; R$_5$ is —CH$_3$.

In one embodiment, of Formula (V) R$_1$ is —CF$_3$; R$_{31}$ is —H; R$_{21}$ is

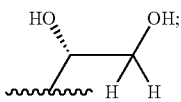

R$_5$ is —CH$_3$.

In one embodiment, of Formula (V) R$_1$ is —CF$_3$; R$_{31}$ is —H; R$_{21}$ is

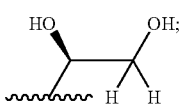 [SMILES: *[C@@H](O)CO]

R$_5$ is —CH$_3$.

In one embodiment, of Formula (V) R$_1$ is —F; R$_{31}$ is —CH$_3$; R$_{21}$ is —H; R$_5$ is —CH$_3$.

In one embodiment, of Formula (V) R$_1$ is —F; R$_{31}$ is —CH$_3$; R$_{21}$ is

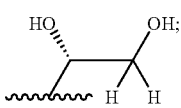

R$_5$ is —CH$_3$.

In one embodiment, of Formula (V) R$_1$ is —F; R$_{31}$ is —CH$_3$; R$_{21}$ is

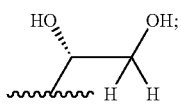

R$_5$ is —CH$_3$.

In one embodiment, of Formula (V) R$_1$ is —Cl; R$_{31}$ is —CH$_3$; R$_{21}$ is —H; R$_5$ is —CH$_3$.

In one embodiment, of Formula (V) R$_1$ is —Cl; R$_{31}$ is —CH$_3$; R$_{21}$ is In one embodiment, of Formula (V) R$_1$ is —Cl; R$_{31}$ is —CH$_3$; R$_{21}$ is

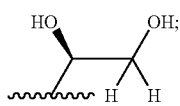 [SMILES: *[C@@H](O)CO]

$R_5$ is —$CH_3$.

In one embodiment, of Formula (V) $R_1$ is —$CF_3$; $R_{31}$ is —$CH_3$; $R_{21}$ is —H; $R_5$ is —$CH_3$.

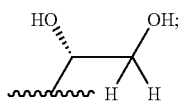 [SMILES: *[C@H](O)CO]

In one embodiment, of Formula (V) $R_1$ is —$CF_3$; $R_{31}$ is —$CH_3$; $R_{21}$ is $R_5$ is —$CH_3$.

In one embodiment, of Formula (V) $R_1$ is —$CF_3$; $R_{31}$ is —$CH_3$; $R_{21}$ is

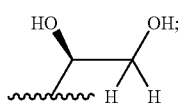 [SMILES: *[C@@H](O)CO]

$R_5$ is —$CH_3$.

One aspect of the present invention also encompasses compounds of Formula (VI) or any pharmaceutically-acceptable salt or hydrate thereof:

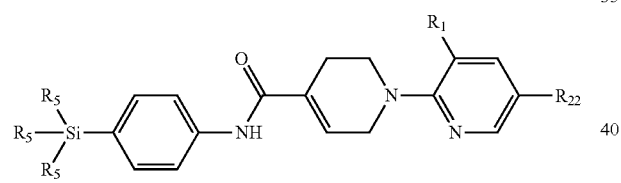

(VI)

Wherein:
$R_1$ is -halo, —$CH_3$, or —$CF_3$.
$R_{22}$ is —H, or

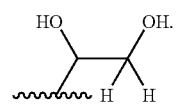

each $R_5$ is independently:
(a) —H, halo, ($C_1$-$C_6$)alkyl, ($C_2$-$C_6$)alkenyl, ($C_2$-$C_6$)alkynyl, ($C_3$-$C_8$)cycloalkyl, ($C_5$-$C_8$)cycloalkenyl, or phenyl, each of which is optionally substituted with 1 or 2 hydroxy groups; or
(b) ($C_1$-$C_6$)alkyl, ($C_2$-$C_6$)alkenyl, ($C_2$-$C_6$)alkynyl, ($C_3$-$C_8$)cycloalkyl, ($C_5$-$C_8$)cycloalkenyl, or phenyl, each of which is substituted by 1 or 2 substituents independently selected from:
(i) $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, $CH=NR_7$, $N(R_7)_2$, $NR_7OH$, $OR_7$, $C(O)R_7$, $C(O)OR_7$, $OC(O)OR_7$, $SR_7$, $S(O)R_7$, or $S(O)_2R_7$; or (ii)

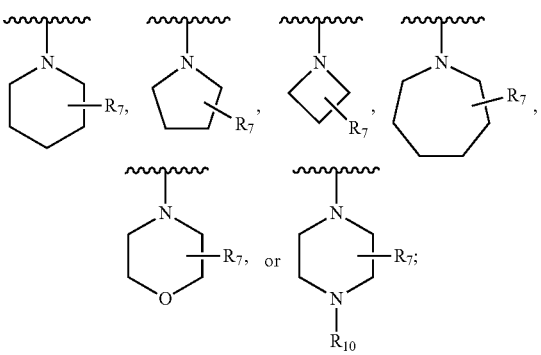

In one embodiment, $R_1$ of Formula (VI) is: -halo.
In one embodiment, $R_1$ of Formula (VI) is: —F.
In one embodiment, $R_1$ of Formula (VI) is: —Cl.
In one embodiment, $R_1$ of Formula (VI) is: —$CH_3$.
In one embodiment, $R_1$ of Formula (VI) is: —$CF_3$.
In one embodiment, $R_{22}$ of Formula (VI) is: —H.
In one embodiment, $R_{22}$ of Formula (VI) is:

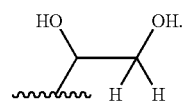

In one embodiment, $R_{22}$ of Formula (VI) is:

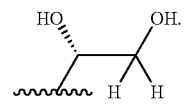

In one embodiment, $R_{22}$ of Formula (VI) is:

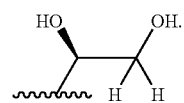

In one embodiment, each $R_5$ of Formula (VI) is independently: —H, halo, ($C_1$-$C_6$)alkyl, ($C_2$-$C_6$)alkenyl, ($C_2$-$C_6$)alkynyl, ($C_3$-$C_8$)cycloalkyl, ($C_5$-$C_8$)cycloalkenyl, or phenyl, each of which is optionally substituted with 1 or 2 hydroxy groups.

In one embodiment, each $R_5$ of Formula (VI) is independently: ($C_1$-$C_6$)alkyl, ($C_2$-$C_6$)alkenyl, ($C_2$-$C_6$)alkynyl, ($C_3$-$C_3$)cycloalkyl, ($C_5$-$C_8$)cycloalkenyl, or phenyl, each of which is substituted by 1 or 2 substituents independently selected from:
(i) $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, $CH=NR_7$, $N(R_7)_2$, $NR_7OH$, $OR_7$, $C(O)R_7$, $C(O)OR_7$, $OC(O)OR_7$, $SR_7$, $S(O)R_7$, or $S(O)_2R_7$; or (ii)

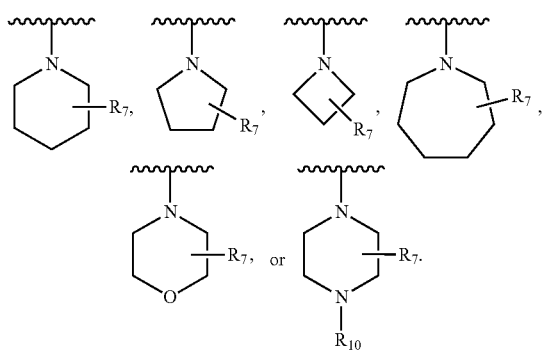

In one embodiment, each $R_5$ of Formula (VI) is independently: —H.

In one embodiment, each $R_5$ of Formula (VI) is independently: $(C_1$-$C_6)$alkyl.

In one embodiment, each $R_5$ of Formula (VI) is independently: —$CH_3$.

In one embodiment, of Formula (VI) $R_1$ is —F; $R_5$ is —$CH_3$; $R_{22}$ is —H.

In one embodiment, of Formula (VI) $R_1$ is —F; $R_5$ is —$CH_3$; $R_{22}$ is

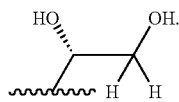

In one embodiment, of Formula (VI) $R_1$ is —F; $R_5$ is —$CH_3$; $R_{22}$ is

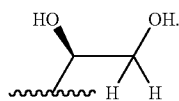 [SMILES: *[C@@H](O)CO]

In one embodiment, of Formula (VI) $R_1$ is —Cl; $R_5$ is —$CH_3$; $R_{22}$ is —H.

In one embodiment, of Formula (VI) $R_1$ is —Cl; $R_5$ is —$CH_3$; $R_{22}$ is

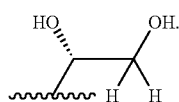

In one embodiment, of Formula (VI) $R_1$ is —Cl; $R_5$ is —$CH_3$; $R_{22}$ is

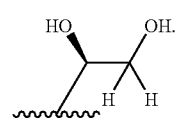

In one embodiment, of Formula (VI) $R_1$ is —$CF_3$; $R_5$ is —$CH_3$; $R_{22}$ is —H.

In one embodiment, of Formula (VI) $R_1$ is —$CF_3$; $R_5$ is —$CH_3$; $R_{22}$ is

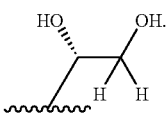

In one embodiment, of Formula (VI) $R_1$ is —$CF_3$; $R_5$ is —$CH_3$; $R_{22}$ is

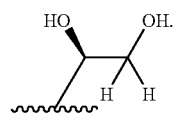

One aspect of the present invention also encompasses compounds of Formula (VII) or any pharmaceutically-acceptable salt or hydrate thereof:

(VII)

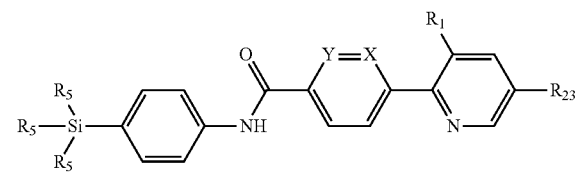

Wherein:
Each X is independently N or C.
Each Y is independently N or C.
$R_1$ is -halo, —$CH_3$, or —$CF_3$.
$R_{23}$ is —H, or

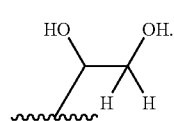

each $R_5$ is independently:
(a) —H, halo, $(C_1$-$C_6)$alkyl, $(C_2$-$C_6)$alkenyl, $(C_2$-$C_6)$alkynyl, $(C_3$-$C_8)$cycloalkyl, $(C_5$-$C_8)$cycloalkenyl, or phenyl, each of which is optionally substituted with 1 or 2 hydroxy groups; or
(b) $(C_1$-$C_6)$alkyl, $(C_2$-$C_6)$alkenyl, $(C_2$-$C_6)$alkynyl, $(C_3$-$C_8)$cycloalkyl, $(C_5$-$C_8)$cycloalkenyl, or phenyl, each of which is substituted by 1 or 2 substituents independently selected from:
(i) $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, $CH=NR_7$, $N(R_7)_2$, $NR_7OH$, $OR_7$, $C(O)R_7$, $C(O)OR_7$, $OC(O)OR_7$, $SR_7$, $S(O)R_7$, or $S(O)_2R_7$; or
(ii)

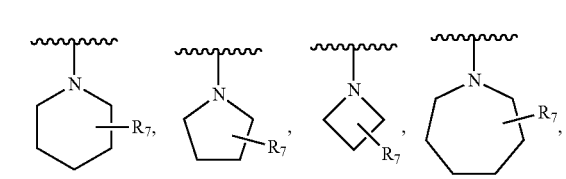

-continued

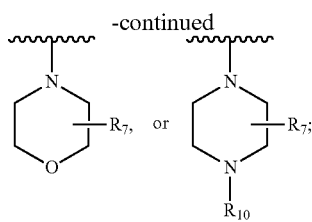

In one embodiment, each X of Formula (VII) is independently N.

In one embodiment, each X of Formula (VII) is independently C.

In one embodiment, each Y of Formula (VII) is independently N.

In one embodiment, each Y of Formula (VII) is independently C.

In one embodiment, $R_1$ of Formula (VII) is: -halo.
In one embodiment, $R_1$ of Formula (VII) is: —F.
In one embodiment, $R_1$ of Formula (VII) is: —Cl.
In one embodiment, $R_1$ of Formula (VII) is: —$CH_3$.
In one embodiment, $R_1$ of Formula (VII) is: —$CF_3$.
In one embodiment, $R_{23}$ of Formula (VII) is: —H.
In one embodiment, $R_{23}$ of Formula (VII) is:

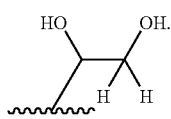

In one embodiment, $R_{23}$ of Formula (VII) is:

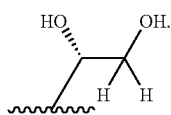

In one embodiment, $R_{23}$ of Formula (VII) is:

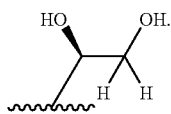

In one embodiment, each $R_5$ of Formula (VII) is independently: —H, halo, $(C_1\text{-}C_6)$alkyl, $(C_2\text{-}C_6)$alkenyl, $(C_2\text{-}C_6)$alkynyl, $(C_3\text{-}C_8)$cycloalkyl, $(C_5\text{-}C_8)$cycloalkenyl, or phenyl, each of which is optionally substituted with 1 or 2 hydroxy groups.

In one embodiment, each $R_5$ of Formula (VII) is independently: $(C_1\text{-}C_6)$alkyl, $(C_2\text{-}C_6)$alkenyl, $(C_2\text{-}C_6)$alkynyl, $(C_3\text{-}C_8)$cycloalkyl, $(C_5\text{-}C_8)$cycloalkenyl, or phenyl, each of which is substituted by 1 or 2 substituents independently selected from:

(i) $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, $CH=NR_7$, $N(R_7)_2$, $NR_7OH$, $OR_7$, $C(O)R_7$, $C(O)OR_7$, $OC(O)OR_7$, $SR_7$, $S(O)R_7$, or $S(O)_2R_7$; or (ii)

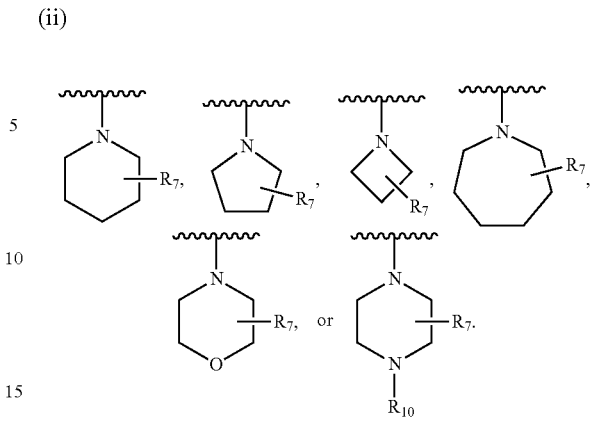

In one embodiment, each $R_5$ of Formula (VII) is independently: —H.

In one embodiment, each $R_5$ of Formula (VII) is independently: $(C_1\text{-}C_6)$alkyl.

In one embodiment, each $R_5$ of Formula (VII) is independently: —$CH_3$.

In one embodiment, of Formula (VII) X is N; Y is N; $R_1$ is —F; $R_5$ is —$CH_3$; $R_{23}$ is —H.

In one embodiment, of Formula (VII) X is N; Y is N; $R_1$ is —F; $R_5$ is —$CH_3$; $R_{23}$ is

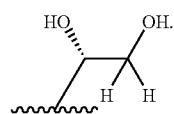

In one embodiment, of Formula (VII) X is N; Y is N; $R_1$ is —F; $R_5$ is —$CH_3$; $R_{23}$ is

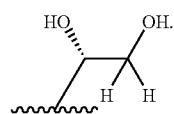

In one embodiment, of Formula (VII) X is N; Y is N; $R_1$ is —Cl; $R_5$ is —$CH_3$; $R_{23}$ is —H.

In one embodiment, of Formula (VII) X is N; Y is N; $R_1$ is —Cl; $R_5$ is —$CH_3$; $R_{23}$ is

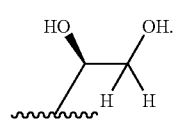

In one embodiment, of Formula (VII) X is N; Y is N; $R_1$ is —Cl; $R_5$ is —$CH_3$; $R_{23}$ is

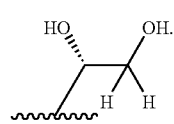

In one embodiment, of Formula (VII) X is N; Y is N; $R_1$ is —$CF_3$; $R_5$ is —$CH_3$; $R_{23}$ is —H.

In one embodiment, of Formula (VII) X is N; Y is N; $R_1$ is —$CF_3$; $R_5$ is —$CH_3$; $R_{23}$ is

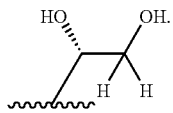

In one embodiment, of Formula (VII) X is N; Y is N; $R_1$ is —$CF_3$; $R_5$ is —$CH_3$; $R_{23}$ is

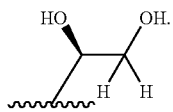

In one embodiment, of Formula (VII) X is N; Y is C; $R_1$ is —F; $R_5$ is —$CH_3$; $R_{23}$ is —H.

In one embodiment, of Formula (VII) X is N; Y is C; $R_1$ is —F; $R_5$ is —$CH_3$; $R_{23}$ is

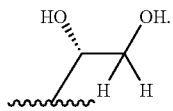

In one embodiment, of Formula (VII) X is N; Y is C; $R_1$ is —F; $R_5$ is —$CH_3$; $R_{23}$ is

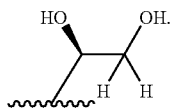

In one embodiment, of Formula (VII) X is N; Y is C; $R_1$ is —Cl; $R_5$ is —$CH_3$; $R_{23}$ is —H.

In one embodiment, of Formula (VII) X is N; Y is C; $R_1$ is —Cl; $R_5$ is —$CH_3$; $R_{23}$ is

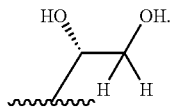

In one embodiment, of Formula (VII) X is N; Y is C; $R_1$ is —Cl; $R'_5$ is —$CH_3$; $R_{23}$ is

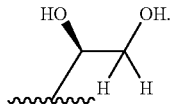

In one embodiment, of Formula (VII) X is N; Y is C; $R_1$ is —$CF_3$; $R_5$ is —$CH_3$; $R_{23}$ is —H.

In one embodiment, of Formula (VII) X is N; Y is C; $R_1$ is —$CF_3$; $R_5$ is —$CH_3$; $R_{23}$ is In one embodiment, of Formula (VII) X is N; Y is C; $R_1$ is —$CF_3$; $R_5$ is —$CH_3$; $R_{23}$ is In one embodiment, of Formula (VII) X is C; Y is C; $R_1$ is —F; $R_5$ is —$CH_3$; $R_{23}$ is —H.

In one embodiment, of Formula (VII) X is C; Y is C; $R_1$ is —F; $R_5$ is —$CH_3$; $R_{23}$ is

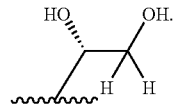

In one embodiment, of Formula (VII) X is C; Y is C; $R_1$ is —F; $R_5$ is —$CH_3$; $R_{23}$ is In one embodiment, of Formula (VII) X is C; Y is C; $R_1$ is —Cl; $R_5$ is —$CH_3$; $R_{23}$ is —H.

In one embodiment, of Formula (VII) X is C; Y is C; $R_1$ is —Cl; $R_5$ is —$CH_3$; $R_{23}$ is

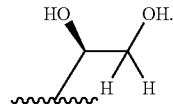 [SMILES: *[C@@H](O)CO]

In one embodiment, of Formula (VII) X is C; Y is C; $R_1$ is —Cl; $R_5$ is —$CH_3$; $R_{23}$ is In one embodiment, of Formula (VII) X is C; Y is C; $R_1$ is —$CF_3$; $R_5$ is —$CH_3$; $R_{23}$ is —H.

In one embodiment, of Formula (VII) X is C; Y is C; $R_1$ is —$CF_3$; $R_5$ is —$CH_3$; $R_{23}$ is

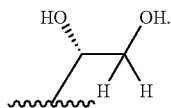

In one embodiment, of Formula (VII) X is C; Y is C; $R_1$ is —$CF_3$; $R_5$ is —$CH_3$; $R_{23}$ is

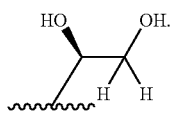

In one embodiment, of Formula (VII) X is C; Y is N; $R_1$ is —F; $R_5$ is —$CH_3$; $R_{23}$ is H.

In one embodiment, of Formula (VII) X is C; Y is N; $R_1$ is —F; $R_5$ is —$CH_3$; $R_{23}$ is

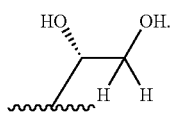

In one embodiment, of Formula (VII) X is C; Y is N; $R_1$ is —F; $R_5$ is —$CH_3$; $R_{23}$ is

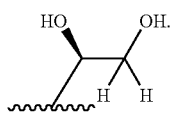

In one embodiment, of Formula (VII) X is C; Y is N; $R_1$ is —Cl; $R_5$ is —$CH_3$; $R_{23}$ is —H.

In one embodiment, of Formula (VII) X is C; Y is N; $R_1$ is —Cl; $R_5$ is —$CH_3$; $R_{23}$ is

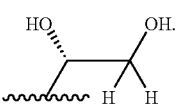

In one embodiment, of Formula (VII) X is C; Y is N; $R_1$ is —Cl; $R_5$ is —$CH_3$; $R_{23}$ is

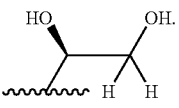 [SMILES: *[C@@H](O)CO]

In one embodiment, of Formula (VII) X is C; Y is N; $R_1$ is —$CF_3$; $R_5$ is —$CH_3$; $R_{23}$ is —H.

In one embodiment, of Formula (VII) X is C; Y is N; $R_1$ is —$CF_3$; $R_5$ is —$CH_3$; $R_{23}$ is

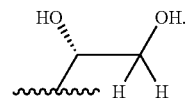

In one embodiment, of Formula (VII) X is C; Y is N; $R_1$ is —$CF_3$; $R_5$ is —$CH_3$; $R_{23}$ is

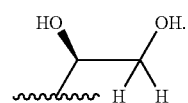 [SMILES: *[C@@H](O)CO]

The above compound and its pharmaceutically acceptable salt or hydrate have the advantages to be the structure determined, stable, potent activity, less toxic, no irritating for the skin and muscle, easily absorbed by animals or humans and so on. They can inhibit the TRPV1 function in cells expressed TRPV1, and can be used for the treatment or prevention of TRPV1-mediated diseases, such as acute, inflammatory and neuropathic pain, tooth pain, general headache, migraine, cluster headache, mixed type of vascular and non-vascular syndromes, tension headache, general inflammation, arthritis, rheumatic diseases, osteoarthritis, inflammatory bowel disease, anxiety, depression, inflammatory eye disorders, inflammatory or unstable bladder disorders, psoriasis, inflammatory skin diseases, chronic inflammation, inflammatory pain and associated hyperalgesia and allodynia, neuropathic pain and associated hyperalgesia and allodynia, diabetic neuropathy, burning pain, sustained sympathetic pain, differentiation syndromes, asthma, epithelial tissue damage or dysfunction, herpes simplex, respiratory, genitourinary, gastrointestinal or vascular regions visceral movement disorders, wounds, burns, allergic skin reactions, itching, vitiligo, general gastrointestinal disorders, gastric ulcer, duodenal ulcer, diarrhea, the necrosis factor induced gastric lesions, hair growth, vasomotor or allergic rhinitis, bronchial disorders or bladder disorders, addiction disease, Parkinson's disease, Parkinson's disease complication, epilepsy, stroke, seizures, psychosis, cognitive impairment, memory loss, restricted brain function, Huntington's chorea, ALS, dementia, retinopathy, muscle spasm, vomiting, motor dysfunction, etc. (each are "symptoms").

The present invention also relates to pharmaceutical compositions comprising any above compound or a pharmaceutically acceptable salt or hydrate thereof, and one or more pharmaceutically acceptable carriers.

In one embodiment, pharmaceutical compositions of the present invention also further comprise an effective amount another pharmaceutically acceptable therapeutic agent.

In one embodiment, the pharmaceutical composition of the present invention is a liquid, tablet, capsule, gel, cream, emulsion, or patch.

The present invention also relates to a use of any above compound or a pharmaceutically acceptable salt or hydrate thereof for the production of a medicament for the inhibition of the TRPV1 function in a cell expressing TRPV1.

The present invention also relates to a use of any above compound or a pharmaceutically acceptable salt or hydrate thereof for the production of a medicament for the treatment of pain.

The present invention also relates to a use of any above compound or a pharmaceutically acceptable salt or hydrate thereof for the production of a medicament for the treatment of an ulcer, IBD or IBS.

The present invention also relates to a method for treating pain comprising administering to a subject in need thereof an effective amount of any above compound or a pharmaceutically acceptable salt or hydrate thereof.

In one embodiment, the present invention also relates to a method for treating pain comprising administering to a subject in need thereof an effective amount of any above compound or a pharmaceutically acceptable salt or hydrate thereof, and an effective amount of another pharmaceutically acceptable therapeutic agent.

The present invention also relates to a method for treating UI, an ulcer, IBD, or IBS comprising administering to a subject in need thereof an effective amount of any above compound or a pharmaceutically acceptable salt or hydrate thereof.

In one embodiment, the present invention also relates to a method for treating UI, an ulcer, IBD, or IBS comprising administering to a subject in need thereof an effective amount of any above compound or a pharmaceutically acceptable salt or hydrate thereof, and an effective amount of another pharmaceutically acceptable therapeutic agent.

The above treatment of the diseases and disorders includes the pharmaceutical compositions comprising the compound of the present invention or a pharmaceutically acceptable salt or hydrate thereof. The object needed to treat can be animal or human, preferably mammalian or human, most preferably human.

The compound of the present invention and its pharmaceutically acceptable salt or hydrate can form a composition which can be applied to the object needed to treat through oral, inhalation, injection, local administration, rectal or parenteral administration. Pharmaceutical compositions of various formulations can be produced according to conventional pharmaceutical preparation methods. For example, the active ingredient with one or more pharmaceutically acceptable carrier can be mixed, and then made to the necessary forms. Pharmaceutical compositions contain preferably weight ratio of 0.1%-99.5% of the active ingredient, most preferably contains a weight ratio of 0.5%-95% of the active ingredient.

In the present invention, a pharmaceutically acceptable carrier refers to the pharmaceutical conventional pharmaceutically acceptable carrier, including but not limited to: diluents, excipients, fillers, binders, wetting agents, disintegrants, absorption enhancers, surfactants agents, adsorption carrier, lubricant, emulsifier, stabilizer, buffer, etc. The composition can be also added by other auxiliary agents, such as flavoring agents, sweeteners, etc. The present invention compounds can be used together with one or more carriers suitable to the route of the administration, such as compounds of the present invention can be mixed with lactose, sucrose, starch, cellulose chain acid esters, stearic acid, talc, hard magnesium stearate, magnesium oxide, sodium pity acid and sulfuric acid and calcium salt, Arabic gum, gelatin, sodium alginate, polyvinyl pyrrolidone, and/or polyvinyl alcohol mixture to form tablet or be encapsulated for conventional administration; the present invention compounds can be dissolved in saline, water, polyethylene glycol, propylene glycol, ethanol, corn oil, peanut oil, cottonseed oil, sesame oil, tragacanth and/or various buffers; and so on. In addition, it also can be the well-known pharmaceutical carriers and other delivery methods in the field. Carriers can also include the control release materials, such as glycerol monostearate or glycerol stearate alone or its mixture with wax, or other materials well known in this field.

The dose amount of the compound of the present invention or its pharmaceutically acceptable salt or hydrate is based on a variety of factors, including disease type, patient's age, weight, gender, medical conditions, disease severity, drug delivery approach and specific compounds used. Therefore, the choice of the dose can vary, but the practice can be determined in accordance with standard methods. The dose level of about 0.01 mg to 50 mg/kg body weight per day can be used for all disclosed methods in the present invention, preferably about 0.1 mg-30 mg/kg body weight. You can use one dose or several doses for the treatment.

The compound of the present invention and its pharmaceutically acceptable salt or hydrate can be processed in accordance with conventional pharmaceutical methods to prepare and administrate pharmaceutical to treat the patient, including human and other mammals. For example, the compound of the present invention and its pharmaceutically acceptable salt or hydrate can form composition to treat the objective needed through oral, inhalation, injection, local administration, rectal or parenteral administration, etc. Pharmaceutical compositions can be made of solid forms (including but not limited to, granules, powders or suppositories) or liquid forms (including but not limited to, solution, suspension or emulsion). Pharmaceutical compositions may be subjected to conventional pharmaceutical operations such as sterilization, and/or containing conventional additives such as preservatives, stabilizers, wetting agents, emulsifiers, buffers, etc.

Solid dosage forms for oral administration may include capsules, tablets, pills, powders and granules. In such solid dosage forms, the active compound can be mixed with at least one inert diluent such as sucrose, lactose or starch. As in normal practice, these formulations can also contain additional substances other than inert diluents, such as lubricants, and such as magnesium stearate. In capsules, tablets and pills, formulations can also contain buffering material. Tablets and pills can be additionally with enteric coating.

Liquid dosage forms for oral administration may include pharmaceutically acceptable emulsions, solutions, suspensions, syrups and elixirs agent, containing inert diluents commonly used in the field, such as water. Such compositions can also contain additives, such as moist, sweet, flavoring agent or fragrance.

Active ingredients can also be delivered by injection. When delivered by injection, the composition contains a suitable carrier, including saline, glucose or water. Daily parenteral dose is about 0.01-30 mg/kg for overall weight, preferably about 0.1-10 mg/kg for overall weight, more preferably about 0.025-1 mg/kg for overall weight. Using a suitable dispersing, diluting or suspending agent, the injection agent can be prepared according to known methods of preparation of injectable materials, such as sterile injectable water or oil suspension. The preparation of sterile injectable agents can also be in sterile injectable solution or suspension with not toxic, parenteral acceptable diluent or solvent, for example, 1,3-butanediol solution. An acceptable carrier and solvent can be water, Ringer's solution and isotonic sodium chloride solution. In addition, sterile oils are routinely used as a solvent or suspending medium. You can use any brand of sterile oils, including synthetic glycerol esters or diacylglycerol. In addition, fatty acids, such as oleic acid can be used for the preparation of injectable agents.

Mixing the drug with a suitable non-irritating excipient can be used to prepare rectal suppositories. The examples of such excipients include cocoa butter and polyethylene glycol, which is solid at room temperature, but a liquid at rectal temperature. Therefore it will melt in the rectum to release the drug.

Preparations of the formulations suitable for local administration include liquid or semi-liquid formulations suitable for penetrating the skin, such as liniment, lotion, ointment, patch, cream or paste; and the drops for eye, ear or nose administration.

Although the compound of the present invention can be administered as the sole active pharmaceutical ingredients, they can also work with one or more other active pharmaceutical ingredients used in combination. Administered as a composition, the therapeutic agent can be configured as a separate composition, administering at the same time or different times. It can also give a composition of the combined two or more active ingredients together used as a single therapeutic agent.

Compounds of the present invention can exist as isomers. They are the compounds with the same molecular formula but with different atomic arrangement of each other.

Compounds of the present invention may have one or more asymmetric chiral carbon atoms, which can exist in the form of optical isomers, and racemic mixture or other stereoisomeric form. The chiral isomers can be obtained by the separation of the racemic mixture according to the conventional methods. For example, the use of optically active acid or alkali generates diastereoisomer salt. Examples of suitable acid are tartaric acid, diacetyl tartaric acid, dibenzoyl tartaric acid, dimethyl benzoyl tartaric acid and camphor sulfonic acid. Separation using recrystallization gives each enantiomer, followed by the release of these optically active alkali (isomer) from the salt. A different separation process of isomers involves using a chiral column, by optimizing the parameters to maximize the separation of enantiomers. Another available method involves the covalent diastereoisomers molecule synthesis, so the optically pure compounds of the present invention react to the activation form of the optically pure acid or optically pure isocyanate. The diastereomeric isomers can be separated using conventional means of separation, such as chromatography, distillation, crystallization or sublimation. Then hydrolysis gives the pure enantiomers. The optically active compounds of the present invention can also be obtained from the optically active starting materials. These isomers can be free acid, free alkali, ester or salt form. To those of ordinary skill in art, the compounds of the present invention in the form of these isomers are interpreted to cover within the scope of the present invention.

Compounds of the present invention can be in salt forms derived from the use of inorganic or organic acids. Salts include, but are not limited to acetate, adipate, alginate, citrate, aspartate, benzoate, benzenesulfonate salts, bisulfate, butyrate, camphor salts, camphor sulfonate, digluconate, cyclopentane propionate, sodium lauryl sulfate, ethyl sulfate, glucoheptonate, glycerophosphate, hemisulfate salt, enanthate, hexanoate, fumarate, hydrochloride, hydrobromide, hydroiodide, 2-hydroxy-ethyl sulfate, lactate, maleate, methanesulfonate, nicotinate, 2-naphthalene sulfonate salts, oxalate, embonate, pectinate, persulfate, 2-phenyl-propionate, picrate, pivalate, propionate, succinate, tartrate, thiocyanate, tosylate, mesylate salts, and undecane. Moreover, the basic nitrogen-containing groups can be quaternized from following reagents, such as lower alkyl halides such as methyl, ethyl, propyl, and butyl chloride, bromide and iodide; dialkyl sulfate, such as dimethyl, diethyl, dibutyl and two pentyl sulfate; long chain halides such as the chloride, bromide and iodide of decyl, lauryl, tetradecy, stearyl; aryl alkyl based halide, such as benzyl and phenethyl bromide; and so on. The resulting oil-soluble or water-soluble or dispersed products are obtained.

The acids which can be used to generate a pharmaceutically acceptable acid addition salts include inorganic acid, such as hydrochloric acid, sulfuric acid, and phosphoric acid, and organic acids, such as oxalic acid, maleic acid, succinic acid and citric acid. Other examples include alkali metal or alkaline earth metal containing salt, such as sodium, potassium, calcium or magnesium salts, or organic base salt.

Furthermore, compounds of the present invention can exist in crystalline solid. They can be crystallized from common solvents such as ethanol, N,N-dimethylformamide and water. Thus, the compounds of the present invention can exist in crystalline form of the parent compound or its pharmaceutically acceptable salts polymorphs, solvate and/or hydrate. All these forms also can be interpreted to fall into the scope of the present invention.

Unless otherwise specified, the following definitions apply to the terms of the descriptions and claims:

1, "—$(C_1-C_{10})$alkyl" means a straight chain or branched non-cyclic hydrocarbon having from 1 to 10 carbon atoms. Representative straight chain —$(C_1-C_{10})$alkyls include methyl, ethyl, n-propyl, n-butyl, n-pentyl, n-hexyl, n-heptyl, n-octyl, n-nonyl and n-decyl, etc. Representative branched-chain —$(C_1-C_{10})$alkyls include isopropyl, sec-butyl, iso-butyl, tert-butyl, iso-pentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethyl butyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl and 3,3-dimethylheptyl.

2, "—$(C_1-C_6)$alkyl" means a straight chain or branched non-cyclic hydrocarbon having from 1 to 6 Carbon atoms. Representative straight chain —$(C_1-C_6)$alkyls include methyl, ethyl, n-propyl, n-butyl, n-pentyl and n-hexyl. Representative branched chain —$(C_1-C_6)$alkyls include isopropyl, sec-butyl, isobutyl, tert-butyl, iso-pentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethyl butyl, 3-ethylbutyl, 1,1-dimethylbutyl, 1,2-dimethylbutyl, 1,3-dimethylbutyl, 2,2-dimethylbutyl 2,3-dimethylbutyl and 3,3-dimethylbutyl.

3, "—$(C_1-C_4)$alkyl" means a straight chain or branched non-cyclic hydrocarbon having from 1 to 4 carbon atoms. Representative straight chain —$(C_1-C_4)$alkyl include methyl, ethyl, n-propyl and n-butyl. Representative branched chain —$(C_1-C_4)$alkyls include isopropyl, sec-butyl, isobutyl and tert-butyl.

4, "—$(C_2-C_{10})$alkenyl" means a straight-chain or branched non-cyclic hydrocarbon having from 2 to 10 carbon atoms and including at least one carbon-carbon double bond. Representative straight chain and branched-chain —$(C_2-C_{10})$alkenyls include vinyl, allyl, 1-butenyl, 2-butenyl, iso-butylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like.

5, "—$(C_2-C_6)$alkenyl" means a straight-chain or branched non-cyclic hydrocarbon having from 2 to 6 carbon atoms and including at least one carbon-carbon double bond. Representative straight chain and branched-chain —$(C_2-C_6)$alkenyls include vinyl, allyl, 1-butenyl, 2-butenyl, iso-butylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl and the like.

6, "—($C_2$-$C_{10}$)alkynyl" means a straight-chain or branched non-cyclic hydrocarbon having from 2 to 10 carbon atoms and including at least one carbon-carbon triple bond. Representative straight chain and branched-chain —($C_2$-$C_{10}$)alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl and the like.

7, "—($C_2$-$C_6$)alkynyl" means a straight-chain or branched non-cyclic hydrocarbon having from 2 to 6 carbon atoms and including at least one carbon-carbon triple bond. Representative straight chain and branched-chain —($C_2$-$C_6$)alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, and the like.

8, "—($C_3$-$C_8$)cycloalkyl" means a saturated cyclic hydrocarbon having from 3 to 8 carbon atoms. Representative —($C_3$-$C_8$)cycloalkyls include cyclopropyl, cyclobutyl, cyclopentyl, cyclohexyl, cycloheptyl, and cyclooctyl.

9, "—($C_5$-$C_8$)cycloalkenyl" means a cyclic non-aromatic hydrocarbon having at least one carbon-carbon double bond in the cyclic system and from 5 to 8 carbon atoms. Representative —($C_5$-$C_8$)cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl and the like.

10, -Phenyl means substituted and unsubstituted phenyl.

11, -Pyridyl means substituted and unsubstituted pyridyl.

12, -Naphthyl means substituted and unsubstituted naphthyl.

13, When the first group is "substituted" by "one or more" of the second group, one or more hydrogen atoms of the first group are substituted by the corresponding number of the second group. When the number of the second group is 2 or more, each second group can be the same or different. In one embodiment, the number of the second group is 1 or 2. In another embodiment, the number of the second group is 1.

14, To those of ordinary skill in art, "pharmaceutically acceptable salt" of the present invention means the salt prepared using conventional methods. And the "pharmaceutically acceptable salt" includes alkali salt of inorganic and organic acid, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid. If the compounds of the present invention include acid functional group, such as carboxyl. To those of ordinary skill in art, carboxyl groups can be formed salt using a pharmaceutically acceptable cation, including alkali, alkaline earth, ammonium, quaternary ammonium cation and so on. The other examples of the "pharmacologically acceptable salt" can be seen below and in Berge et al., J. Pharm. Sci. 66: 1 (1977).

The following specific examples give more detailed description of the present invention. These examples allow the professional and technical persons more fully understand the present invention, but not in any way limit the present invention.

EXPERIMENTAL METHODS

The following specific examples are the detailed description of the invention, but the present invention is not limited to this.

Unless otherwise mentioned, all starting materials are received from the commercial suppliers, and can be used without further purification. Unless otherwise noted, all reactions are according to weight, and temperature is Celsius degree. The following abbreviations are used:

-Me: methyl

—SiMe3: trimethylsilyl

DMSO: dimethyl sulfoxide

DMF: N,N-dimethyl formamide

DIPEA: diisopropyl ethylamine $Ac_2O$: acetic anhydride

THF: tetrahydrofuran

EtOAc: ethyl acetate

BOP: Benzotriazol-1-yloxytris(dimethylamino)-phosphonium hexafluorophosphate

LiHMDS: lithium hexamethyldisilazide

DPPP: 1,3-Bis(diphenylphosphino)propane

Pd (dppf)$Cl_2$: [1,1'-Bis(diphenylphosphino)ferrocene]dichloropalladium

LAH: lithium aluminum hydride $(Boc)_2O$: di-tert-butyl dicarbonate (BOC anhydride)

TFA: trifluoroacetic acid nBuLi: n-butyl lithium min. minutes h: hour

The compounds of this invention can be prepared by the conventional organic synthesis methods or prepared by following the examples described below.

1. Synthesis of N-substituted phenyl-4-(3-substituted-2-pyridyl)-piperazine-1-carboxamide compounds N-substituted phenyl-4-(3-substituted-2-pyridyl)-piperazine-1-carboxamide compounds can be prepared by following the synthetic route (referred below as method 1) as shown in the scheme 1.

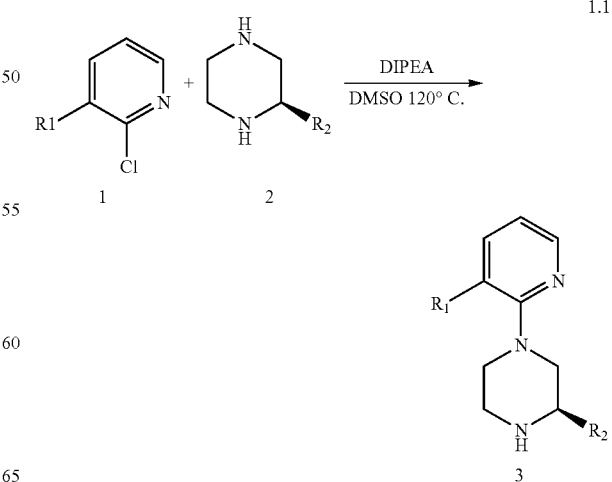

47

-continued 1.2.1

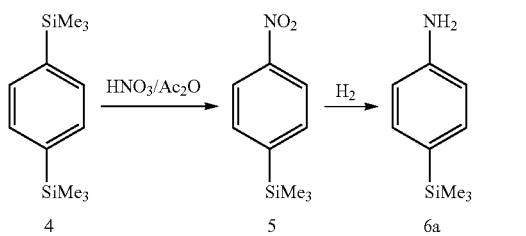

1.2.2

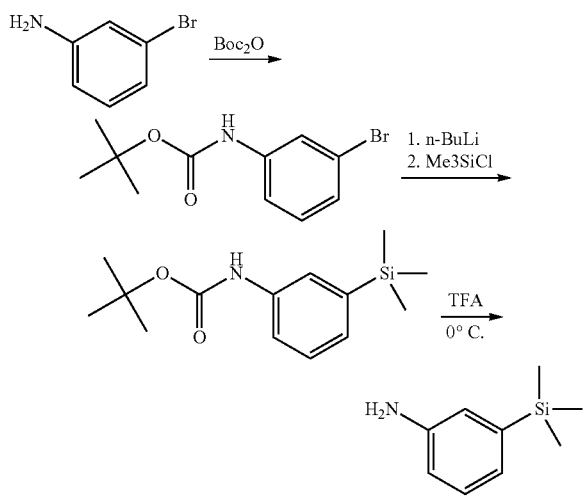

1.2.3

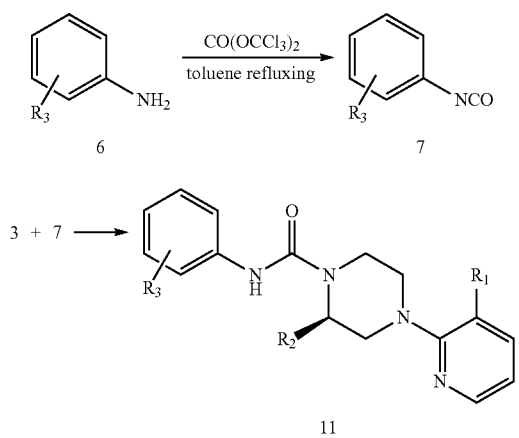

1.3

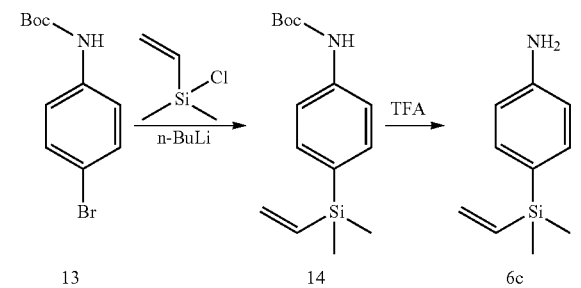

1.4

3 + 7 →

11

In which, as described above for $R_1$, $R_2$, and $R_3$, the preferred $R_1$ is —Cl, —CF$_3$, or —F; the preferred $R_2$ is —H or -Me; the preferred $R_3$ is p-SiMe$_3$, m-SiMe$_3$, or p-dimethyl (vinyl)silyl.

48

1.1 Synthesis of 1-(3-substituted-2-pyridyl)-piperazine (Compound 3)

The reaction mixture of 2-chloro-3-substituted pyridine (compound 1), 2-substituted piperazine (compound 2) (1.5 equivalent) and diisopropyl ethylamine in DMSO was heated to 120° C. overnight (14~16 h). After cooled to room temperature, the mixture was diluted with five times of ethyl acetate, then washed twice with 5 times of water, washed once with brine, and dried with anhydrous sodium sulfate. The organic layer was evaporated and concentrated to give a crude product compound 3 (yield 80 to 90%). The crude product compound 3 was directly used for the next step.

1.2 Synthesis of Trimethylsilyl Aniline (Compound 6)

1.2.1 Synthesis of p-Trimethylsilyl Aniline (Compound 6a of Scheme 1)

Following synthetic route 1.2.1 on Scheme 1, para ditrimethylsilyl benzene (compound 4) (5 g) was dissolved in 30 ml of acetic anhydride. Concentrated nitric acid (10 ml) was added slowly into the reaction mixture under vigorous stirring. The temperature of reaction solution increased to 80~100° C. in the adding process. After the reaction was heated to reflux overnight, the reaction mixture was cooled to room temperature. Ethyl acetate and 2N NaOH was added to the reaction mixture. The organic layer was washed with water and brine, and concentrated to give a crude product. The crude product was purified by the column using petroleum ether to give 2.3 g of pure product of para trimethylsilyl nitrobenzene (referred below as compound 5).

Compound 5 (200 mg) was dissolved in methanol, followed by adding 10 mg 10% Pd/C catalyst. The reaction was hydrogenated under a balloon filled with hydrogen for half an hour. The reaction mixture was filtered to remove the catalyst. The filtrate was evaporated and concentrated to give compound 6a (160 mg).

1.2.2 Compound 6B, m-Trimethylsilyl Aniline, can be Prepared Following Synthetic Route 1.2.2 of Scheme 1

1.2.3 Compound 6c, p-Dimethyl(Vinyl)Silyl Aniline, can be Prepared Following Synthetic Route 1.2.3 of Scheme 1. The detailed synthetic Method is illustrated in Example 11

1.3. Synthesis of Substituted Phenyl Isocynate (Compound 7)

According to synthetic route 1.3, the triphosgene (116 mg, 0.4 eq) was dissolved in 5 ml toluene as the reaction solution. Compound 6 (160 mg) in 2 ml toluene was slowly added to the reaction solution. Reaction mixture was stirred at room temperature for 15 min, and heated to reflux for 4 h. After the solid in reaction solution is completely gone, the solution was evaporated. Then appropriate amount of toluene was added and the solution was evaporated again. The obtained oily product (~100%) was directly used for the next step of the reaction.

1.4 Synthesis of N-Substituted Phenyl-4-(3-Substituted-2-Pyridyl)-Piperazine-1-carboxamide (Compound 11)

According to synthetic route 1.4, the isocyanate (compound 7) synthesized in 1.3 was dissolved in dichloromethane, and cooled to 0° C. 1 equivalent of compound 3 in dichloromethane solution was added to the reaction mixture. The reaction mixture was stirred at room temperature for half an hour. The solvent was evaporated. The product was purified by column chromatography to give compound 11.

2. Synthesis of N-Substituted Phenyl-(3-Substituted-2-Pyridyl)Benzamide compounds N-substituted phenyl-(3-substituted 2-pyridyl)benzamide compounds can be prepared by following the synthetic route (referred below as method 2) as shown in the scheme 2.

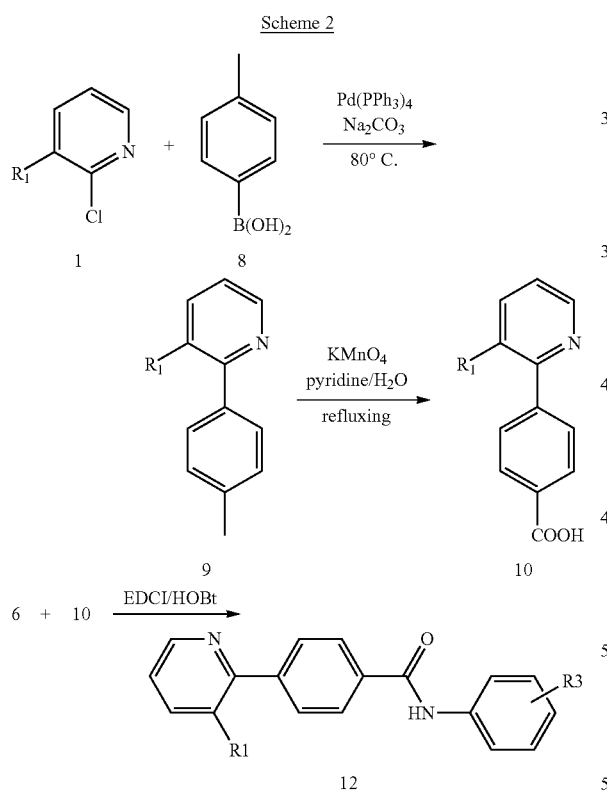

Scheme 2

In which, as described above for $R_1$ and $R_3$, the preferred $R_1$ is —Cl, —CF$_3$, or —F; the preferred $R_3$ is p-SiMe$_3$, m-SiMe$_3$, or p-dimethyl(vinyl)silyl.

2.1 Synthesis of 4-(3-Substituted 2-Pyridyl)Benzoic Acid (Compound 10)

Compound 1, p-tolylboronic acid (compound 8) (1 equivalent) and sodium carbonate (3 equivalents) were dissolved in 10% acetonitrile in water. After nitrogen bubbling for 30 min, Pd(PPh$_3$)$_4$ was added into the reaction mixture. The mixture was heated under nitrogen at 80° C. for 12 h. After cooled to room temperature, ethyl acetate was added. Ethyl acetate layer was washed with brine, dried with anhydrous sodium sulfate and concentrated to give a crude product, which was purified by column chromatography (100% petroleum ether to 10% ethyl acetate/petroleum ether) to give a pure product of 4-(3-substituted 2-pyridyl) toluene (referred below as compound 9) (yield about 80-90%).

Compound 9 was dissolved in pyridine/water (1:10) solvent mixture, followed by adding 3 times of potassium permanganate. The reaction mixture was heated to reflux for 4 hours. After Cooled to room temperature, a small amount of ethanol was added to remove excess potassium permanganate. Manganese dioxide solid was filtered, and the filtrate was acidified to pH 3, and extracted with ethyl acetate. The organic layer was dried with anhydrous sodium sulfate, and evaporated to give compound 10 (yield 100%).

2.2 Synthesis of N-substituted phenyl-4-(3-substituted-2-pyridyl)benzamide (compound 10)

Compound 6 (see the synthesis method described in the method 1), compound 10, BOP and triethylamine were mixed in tetrahydrofuran, and stirred under nitrogen overnight. The reaction solution was concentrated. Ethyl acetate and 0.5NHCl were added to the residue to give 2 layers. The organic layer was washed with water and brine, and then dried with anhydrous sodium sulfate. The organic layer was concentrated, and the crude product was purified by column chromatography to give compound 12.

3. Synthesis of the Compounds of Formula (X)

The compounds of Formula (X) can be synthesized by conventional methods of organic synthesis, and also can be synthesized following the synthetic route of Scheme 3. The detailed synthetic method of the synthetic route in Scheme 3 is very similar to the synthetic route of the Scheme 1 of PCT publication WO2008/133973 (please see page 68-72 of PCT publication WO2008/133973). To make it simple, we won't repeat it here.

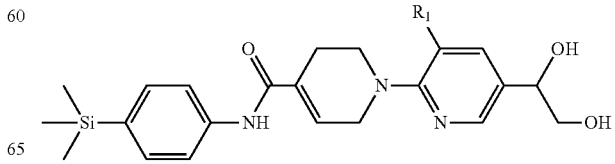

Formula (X)

Scheme 3
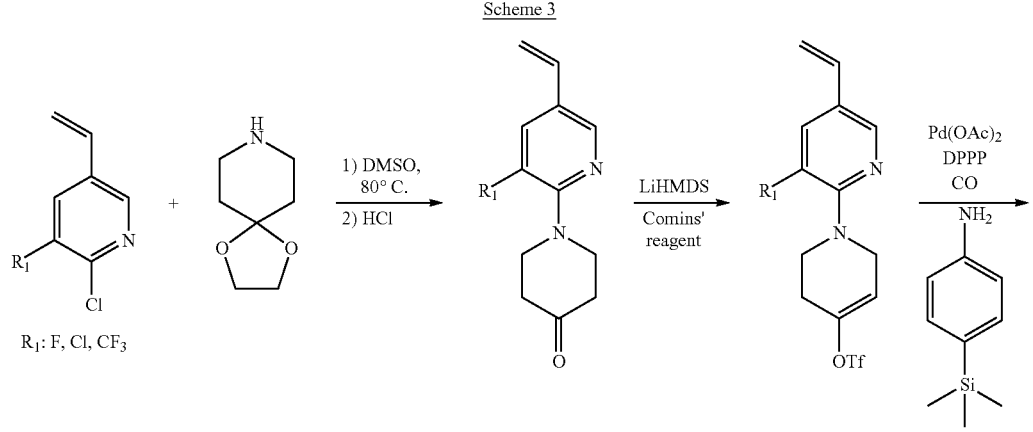
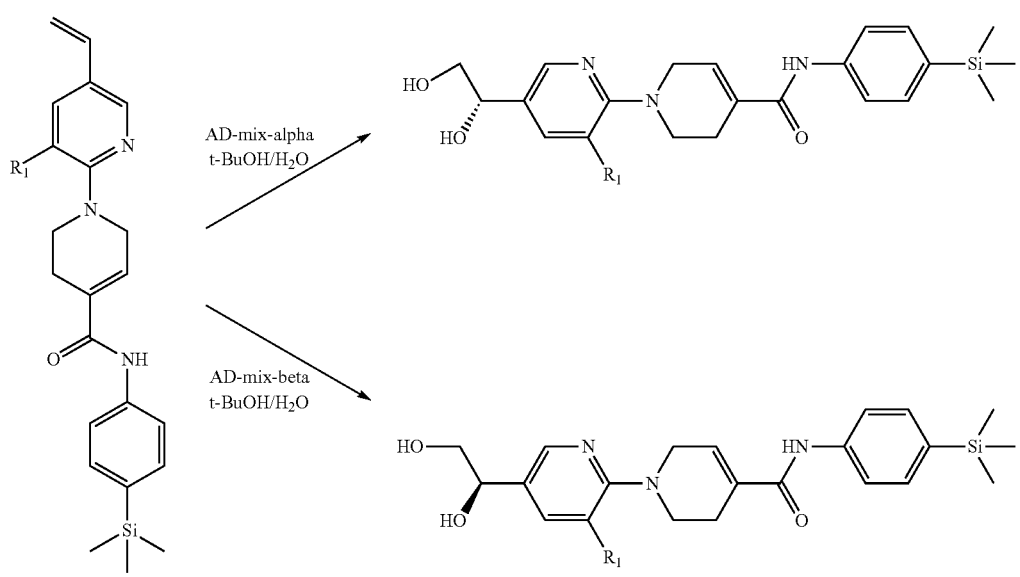
The compounds of formula (X) also can be synthesized by the synthetic route of Scheme 4, using the synthetic method similar to the synthetic method of the Scheme 1 in PCT publication WO2008/133973 (Please see page 68-72 of PCT publication WO2008/133973).

Scheme 4
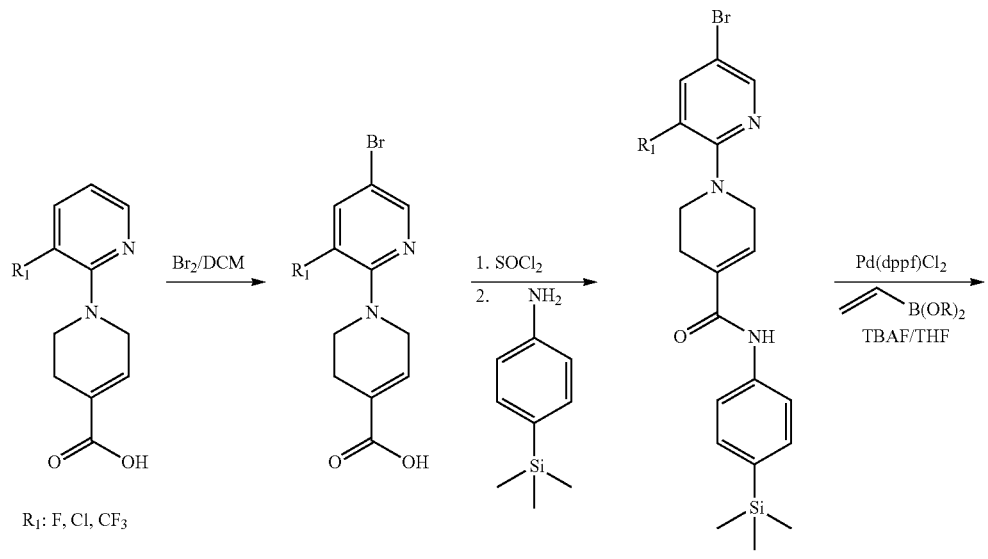
R$_1$: F, Cl, CF$_3$
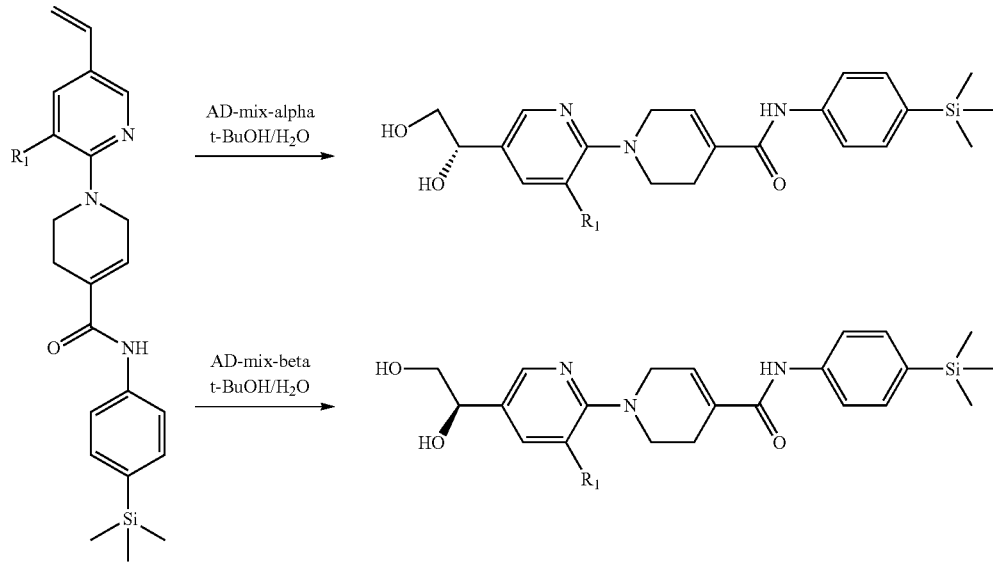
4. Synthesis of the Compounds of Formula (XI)
The compounds of Formula (XI) can be synthesized by conventional methods of organic synthesis, and also can be synthesized following the synthetic route of Scheme 5.
Formula (XI)
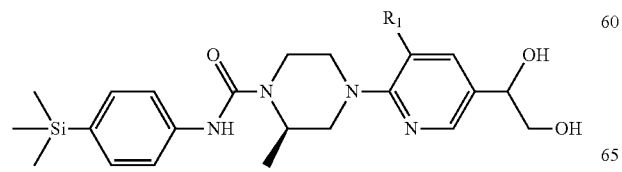

Scheme 5
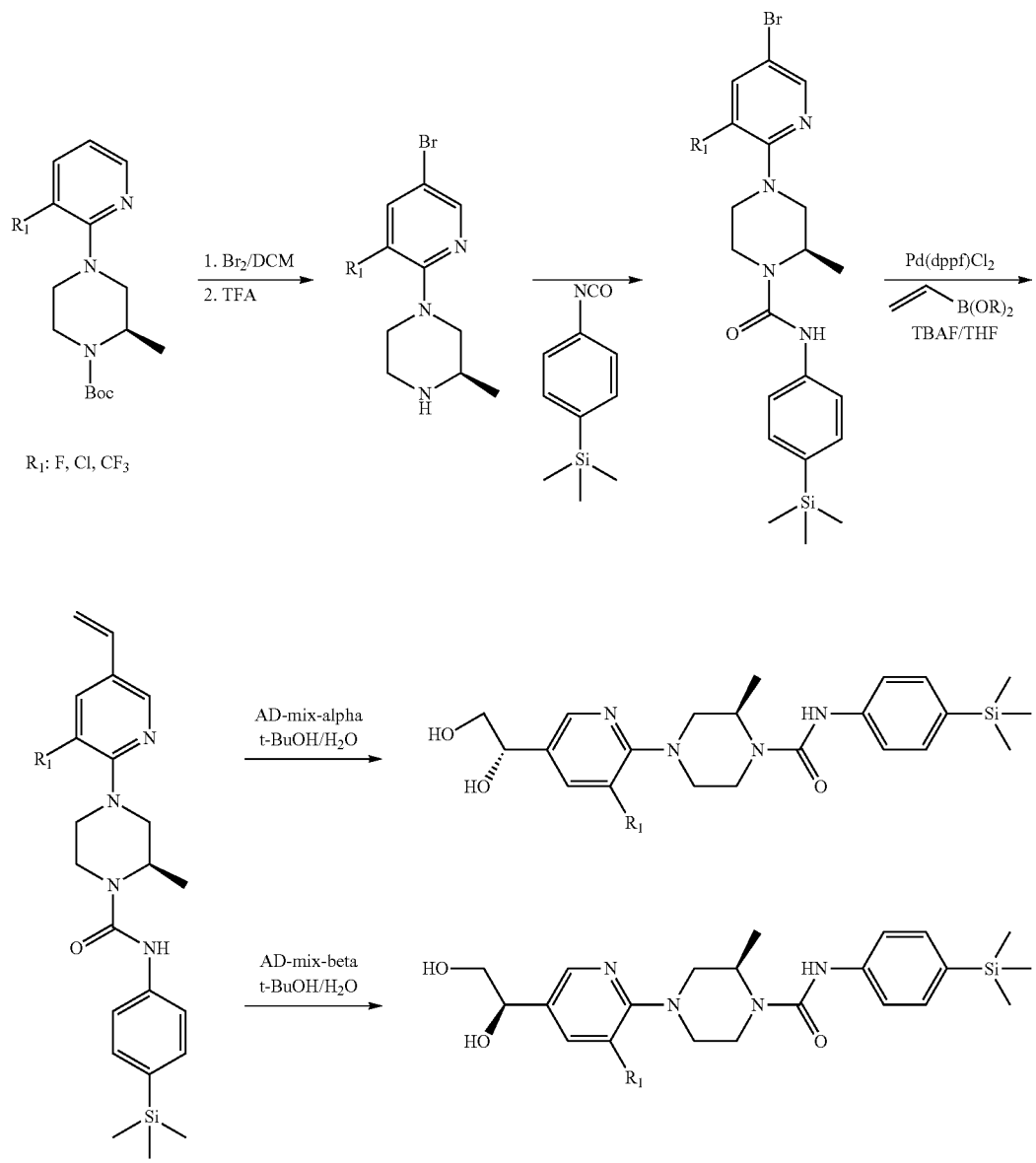
5. Synthesis of the Compounds of Formula (XII)
The compounds of Formula (XII) can be synthesized by conventional methods of organic synthesis, and also can be synthesized following the synthetic route of Scheme 6.
Formula (XII)
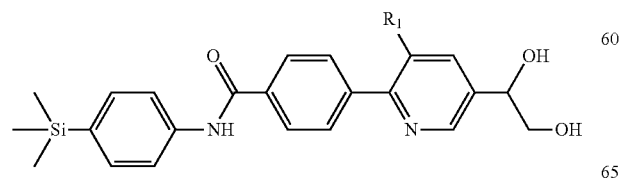

Scheme 6

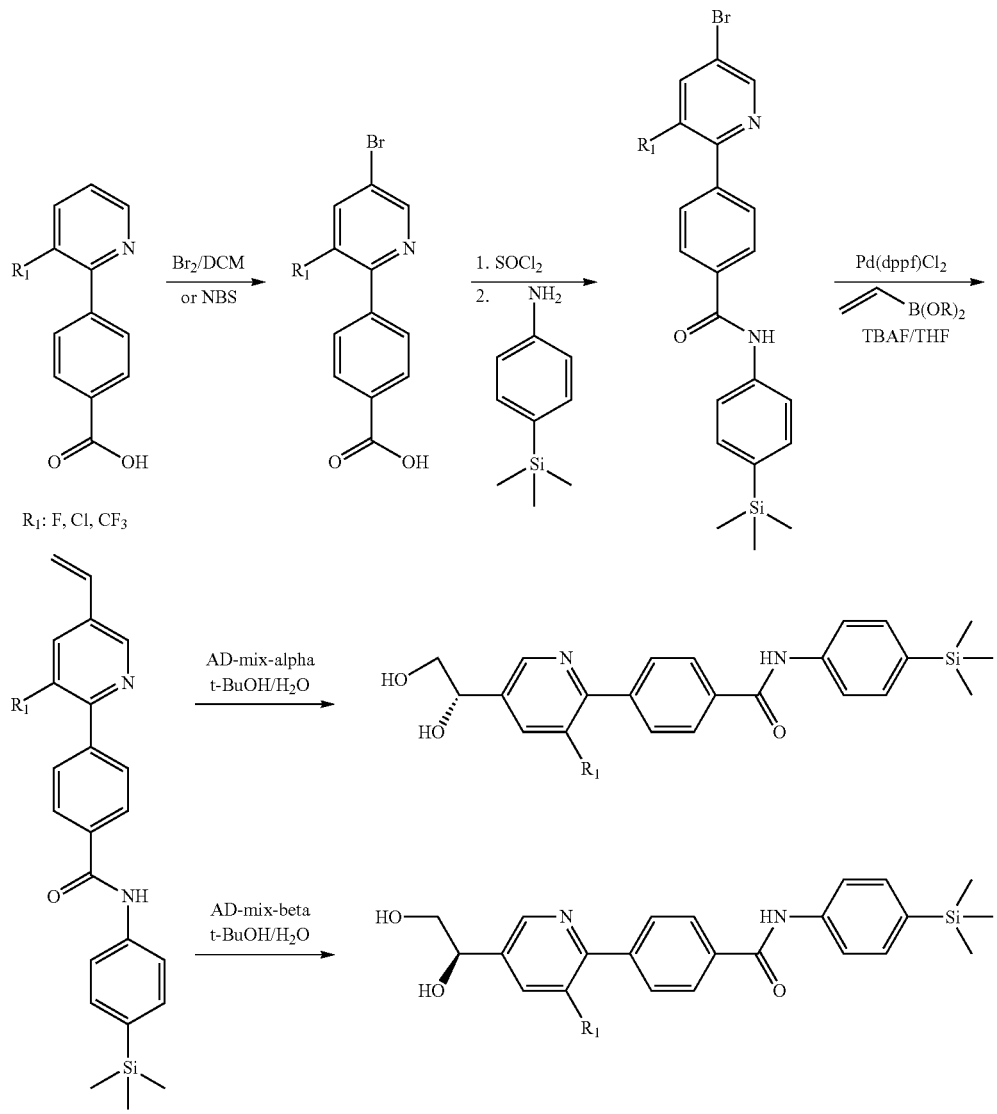

Example 1

Synthesis of 4(3-chloropyridin-2-yl)-N-(4-(trimethylsilyl)phenyl)piperazine-1-carboxamide (Compound A-01)

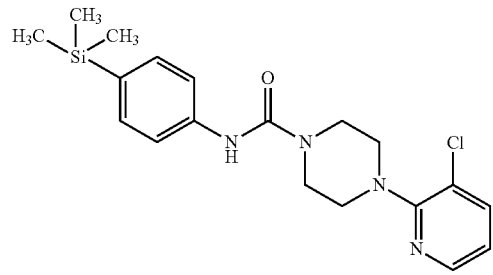

Compound A-01 can be synthesized according to method 1. Just $R_1$, $R_2$, and $R_3$ of Scheme 1 are respectively —Cl, —H and p-SiMe$_3$. More specifically, compound 1 is 2,3-dichloropyridine (2 g); compound 2 is piperazine; compound 3 is 1-(3-chloro-2-pyridyl)piperazine (2.3 g, yield 86.8%); compound 7 is compound 7a-p-(trimethylsilyl)phenyl isocynate.

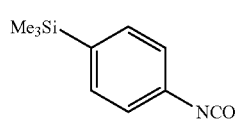

In this example, from 382 mg of compounds 7a, it gave about 500 mg of compound A-01. The yield is about 65%.

Using 1H NMR to identify compound A-01: 1H NMR (300 MHz, CDCl₃): δ8.18 (m, 1H), 7.63 (m, 1H), 7.45-7.34 (dd, 4H), 6.85 (m, 1H), 6.54 (s, 1H), 3.70-3.60 (m, 4H), 3.45-3.35 (m, 4H), 0.24 (s, 9H).

Example 2

Synthesis of (R)-4-(3-chloropyridin-2-yl)-2-methyl-N-(4-(trimethylsilyl)phenyl)piperazine-1-carboxamide (compound A-02)

A-02

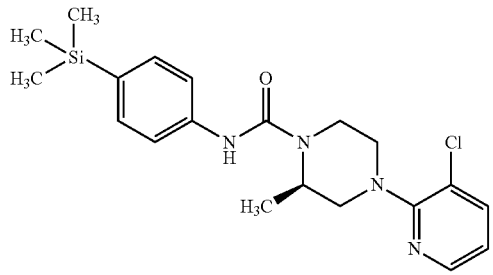

Compound A-02 can be synthesized according to method 1. Just R₁, R₂, and R₃ of Scheme 1 are respectively —Cl, -Me and p-SiMe₃. More specifically, compound 1 is 2,3-dichloropyridine (6 g), compound 2 is (R)-2-methylpiperazine, the synthesized compound 3 is 1-(3-chloro-2-pyridyl)-3-methylpiperazine (38 g, yield about 93.2%).

In this synthesis, from p-(trimethylsilyl)phenyl isocynate (compound 7a, 191 mg), it gave about 180 mg of compound A-02 (yield about 50%).

Using 1H NMR to identify compound A-02: NMR (300 MHz, CDCl₃): δ 8.20 (m, 1H), 7.63 (m, 1H), 7.46-7.38 (dd, 4H), 6.88 (m, 1H), 6.40 (s, 1H), 4.37 (m, 1H), 3.94-3.90 (m, 1H), 3.83-3.73 (m, 2H), 3.53-3.40 (m, 1H), 3.12-2.96 (m, 2H), 1.45 (d, 3H), 0.24 (s, 9H).

Example 3

Synthesis of (R)-2-methyl-4-(3-(trifluoromethyl)pyridin-2-yl)-N-(4-(trimethylsilyl)phenyl)piperazine-1-carboxamide (compound A-03)

A-03

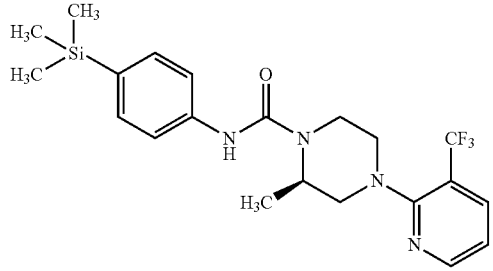

Compound A-03 can be synthesized according to method 1. Just of Scheme 1, R₁ is —CF₃; R₂ is -Me; R₃ is p-SiMe₃. More specifically, compound 1 is 2-chloro-3-(trifluoromethyl)-pyridine (2 g); compound 2 is (R)-2-methylpiperazine; the synthesized compound 3 is 3-methyl-1-(3-trifluoromethyl-2-pyridyl)piperazine (2.5 g, yield about 92.6%).

In this synthesis, from p-(trimethylsilyl)phenyl isocynate (compound 7a, 85 mg), it gave about 100 mg of compound A-03 (yield about 52%).

Using 1H NMR to identify compound A-03: NMR (300 MHz, CDCl₃): δ 8.47 (m, 1H), 7.91 (m, 1H), 7.46-7.35 (dd, 4H), 7.07 (m, 1H), 6.36 (s, 1H), 4.34 (m, 1H), 3.92-3.86 (m, 1H), 3.56-3.39 (m, 3H), 3.30-3.24 (m, 1H), 3.10-2.99 (m, 1H), 1.37 (d, 3H), 0.24 (s, 9H).

Example 4

Synthesis of 4-(3-(trifluoromethyl)pyridin-2-yl)-N-(4-(trimethylsilyl)phenyl)piperazine-1-carboxamide (compound A-07)

A-07

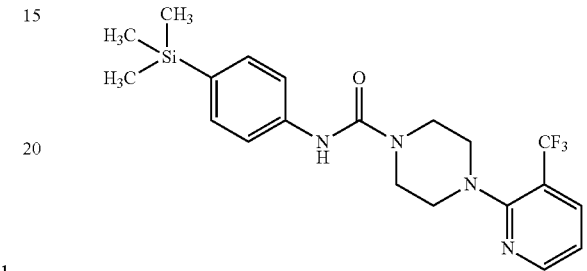

Compound A-07 can be synthesized according to method 1. Just of Scheme 1, R₁ is —CF₃; R₂ is —H; R₃ is p-SiMe₃. More specifically, compound 1 is 2-chloro-3-(trifluoromethyl)pyridine (2 g); compound 2 is piperazine; the synthesized compound 3 is 1-(3-(trifluoromethyl)-2-pyridyl)piperazine (2.3 g, yield about 90.1%).

From p-(trimethylsilyl)phenyl isocynate (compound 7a, 96 mg), it gave about 130 mg of compound A-07 (yield about 61.5%).

Using 1H NMR to identify compound A-07: NMR (300 MHz, CDCl₃): δ 8.46 (m, 1H), 7.91 (m, 1H), 7.47-7.34 (dd, 4H), 7.06 (m, 1H), 6.43 (s, 1H), 3.65 (m, 4H), 3.35 (m, 4H), 0.25 (s, 9H).

Example 5

Synthesis of (R)-2-methyl-4-(3-(trifluoromethyl)pyridin-2-yl)-N-(3-(trimethylsilyl)phenyl)piperazine-1-carboxamide (compound A-09)

A-09

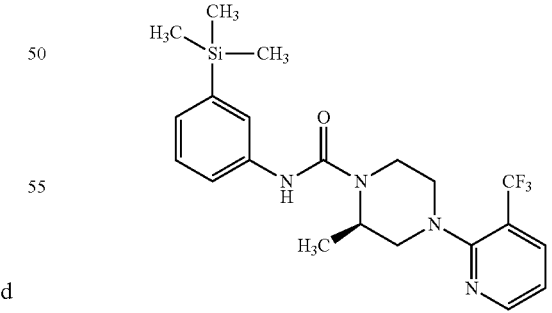

Compound A-09 can be synthesized according to method 1. Just of Scheme 1, R₁ is —CF₃; R₂ is -Me; R₃ is m-SiMe₃.

More specifically, compound 1 is 2-chloro-3-trifluoroethylpyridine (2 g); compound 2 is (R)-2-methyl piperazine; the synthesized compound 3 is 3-methyl-1-(3-trifluoromethyl-2-pyridyl)piperazine (2.5 g, yield about 92.6%).

From m-(trimethylsilyl)phenyl isocynate (compound 7b, 200 mg), it gave about 280 mg of compound A-09 (yield about 61.4%).

Using 1H NMR to identify compound A-09: NMR (300 MHz, CDCl₃): δ 8.47 (m, 1H), 7.91 (m, 1H), 7.50-7.41 (m, 2H), 7.30 (t, 1H), 7.20 (m, 1H), 7.05 (m, 1H), 6.37 (s, 1H), 4.45-4.34 (m, 1H), 3.92-3.86 (m, 1H), 3.60-3.39 (m, 3H), 3.30-3.20 (m, 1H), 3.12-2.99 (m, 1H), 1.39 (d, 3H), 0.26 (s, 9H).

Example 6

Synthesis of (R)-4-(3-chloropyridin-2-yl)-2-methyl-N-(3-(trimethylsilyl)phenyl)piperazine-1-carboxamide (compound A-10)

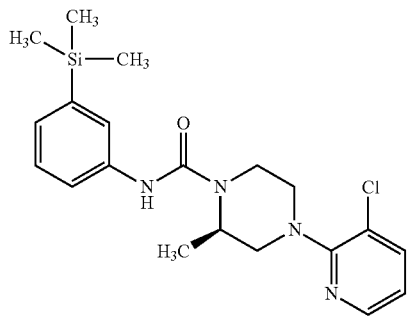

Compound A-10 can be synthesized according to method 1. Just of Scheme 1, R₁ is —Cl; R₂ is -Me; R₃ is m-SiMe₃. More specifically, compound 1 is 2,3-dichloro pyridine (6 g); compound 2 is (R)-2-methyl piperazine; the synthesized compound 3 is 3-methyl-1-(3-chloro-2-pyridyl)piperazine (8 g, yield about 93.2%).

From m-(trimethylsilyl)phenyl isocynate (compound 7b, 200 mg), it gave about 280 mg of compound A-10 (yield about 66.6%).

Using 1H NMR to identify of compound A-10: NMR (300 MHz, CDCl₃): δ 8.20 (m, 1H), 7.63 (m, 1H), 7.46-7.38 (m, 2H), 7.30 (t, 1H), 7.20-7.15 (m, 1H), 6.92-6.85 (m, 1H), 6.39 (s, 1H), 4.39 (m, 1H), 3.96-3.90 (m, 1H), 3.83-3.74 (m, 2H), 3.55-3.45 (m, 1H), 3.15-2.92 (m, 2H), 1.46 (d, 3H), 0.27 (s, 9H).

Example 7

Synthesis of 4-(3-chloropyridin-2-yl)-N-(3-(trimethylsilyl)phenyl)piperazine-1-carboxamide (compound A-11)

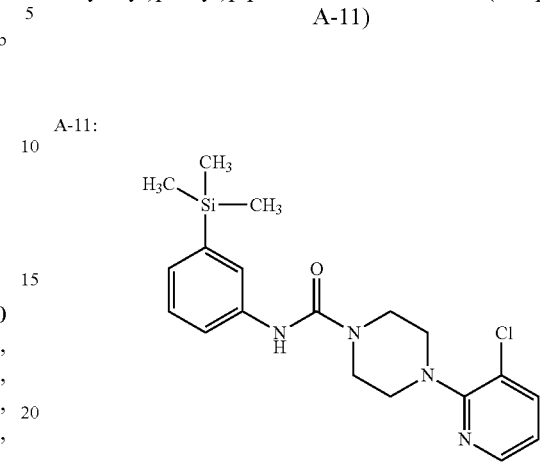

Compound A-11 can be synthesized according to method 1. Just of Scheme 1, R₁ is —Cl; R₂ is —H; R₃ is m-SiMe₃. More specifically, compound 1 is 2,3-dichloro pyridine (2 g); compound 2 is piperazine; the synthesized compound 3 is 1-(3-chloro-2-pyridyl)piperazine (2.3 g, yield about 86.8%).

From m-(trimethylsilyl)phenyl isocynate (compound 7b, 200 mg), it gave about 300 mg of compound A-11 (yield about 73.6%).

Using 1H NMR to identify compound A-11: NMR (300 MHz, CDCl₃ 88.20 (m, 1H), 7.63 (m, 1H), 7.47-7.41 (m, 2H), 7.35 (t, 1H), 7.20-7.15 (m, 1H), 6.92-6.80 (m, 1H), 6.39 (s, 1H), 3.68 (m, 4H), 3.42 (m, 4H), 0.26 (s, 9H).

Example 8

Synthesis of (R)-4-(3-chloropyridin-2-yl)-N-(4-(dimethyl(vinyl)silyl)phenyl)-2-methylpiperazine-1-carboxamide (compound A-15)

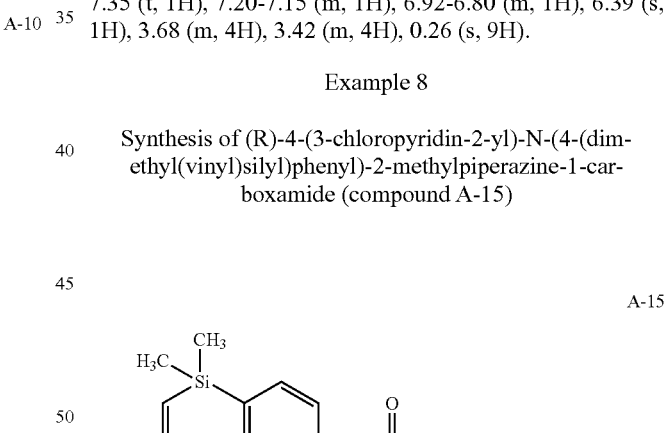

The synthesis method of compound A-15 is similar to example 1. Just R₁ is —Cl; R₂ is -Me; R₃ is dimethyl(vinyl) silyl.

More specifically, compound 1 is 2,3-dichloro pyridine (2 g); compound 2 is (R)-2-methyl-piperazine; the synthesized compound 3 is 1-(3-chloro-2-pyridyl)-3-methyl-piperazine (8 g, yield 86.8%). From p-dimethyl(vinyl)silyl phenyl isocynate (compound 7c, 200 mg), it gave about 250 mg of compound A-15 (yield about 61.2%).

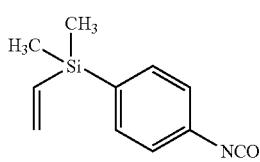
(7c)

Using 1H NMR to identify compound A-15: NMR (300 MHz, CDCl₃): δ 8.20 (m, 1H), 7.63 (m, 1H), 7.40-7.35 (dd, 4H), 6.88 (m, 1H), 6.40 (s, 1H), 6.30-6.20 (m, 1H), 6.05-6.95 (m, 1H), 5.75-5.65 (m, 1H), 4.37 (m, 1H), 3.94-3.90 (m, 1H), 3.88-3.73 (m, 2H), 3.55-3.40 (m, 1H), 3.15-2.96 (m, 2H), 1.45 (d, 3H), 0.35 (s, 9H).

Example 9

Synthesis of 4-(3-(trifluoromethyl)pyridin-2-yl)-N-(4-(trimethylsilyl)phenyl)benzamide (compound A-04)

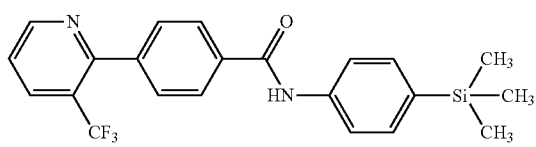
A-04

Compound A-04 can be synthesized according to method 2. Just R₁ and R₃ of Scheme 2 are, respectively, CF₃ and p-SiMe₃. namely: compound 6 is 4-trimethylsilyl aniline (compound 6a 35 mg); compound 10 is 4-(3-trifluoromethylpyridine-2-yl)benzoic acid (compound 10b); compound 12 is compound A-04 (60 mg, yield 68.3%).

6a

Me₃Si——NH₂

10b

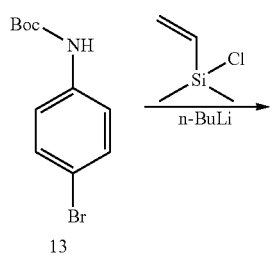

Using 1H NMR to identify compound A-04: 1H NMR (300 MHz, CDCl₃): δ 8.86 (m, 1H), 8.11 (m, 1H), 8.15-7.92 (m, 3H), 7.67-7.45 (m, 7H), 0.24 (s, 9H).

Example 10

Synthesis of 4-(3-fluoro-pyridin-2-yl)-N-(4-(trimethylsilyl)phenyl)benzamide (compound A-08)

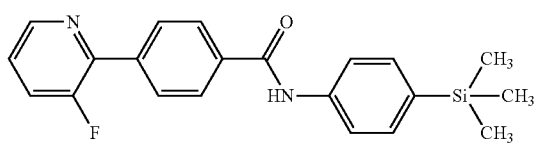
A-08

The synthesis method of compound A-08 is similar to example 9. Just R₁ and R₃ of Scheme 2 are, respectively, F and p-SiMe₃. namely: compound 6 is 4-trimethylsilyl aniline (compound 6a 35 mg); compound 10 is 4-(3-fluoro-pyridine-2-yl)benzoic acid (compound 10c); compound 12 is compound A-08 (62 mg, yield 80.23%).

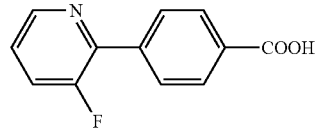
10c

The Using 1H NMR to identify compound A-08: ¹H NMR (300 MHz, CDCl₃): δ8.53 (m, 1H), 8.10-7.95 (m, 4H), 7.90 (s, 1H), 7.65-7.45 (m, 5H), 7.31 (m, 1H), 0.26 (s, 9H).

Example 11

Synthesis of N-(4-(dimethyl(2-(piperidin-1-yl)ethyl) silyl)phenyl)-4-(3-(trifluoromethyl)pyridin-2-yl) benzamide (compound A-22)

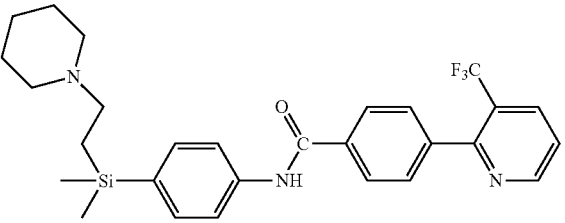
A-22

1. Synthesis of 4-(dimethyl(2-(piperidin-1-yl)ethyl) silyl)aniline according to the synthetic route in Scheme 7 (compound 16 in Scheme 7)

Scheme 7

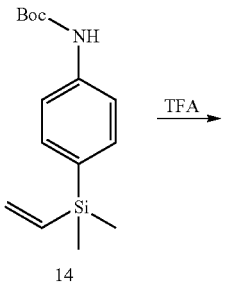
13

14

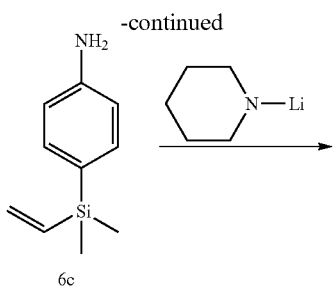

6c

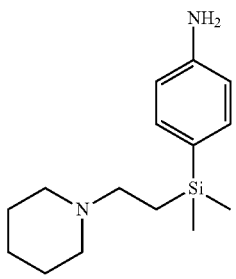

16

(1) Synthesis of tert-butyl 4-(dimethyl(vinyl)silyl)phenylcarbamate (compound 14)

At −78° C., n-butyl lithium (2.5 ml/L, 37 ml) was slowly added dropwise into the THF solution of compound 13(10 g, 36.8 mmol). The reaction mixture was stirred at low the temperature for 30 minutes. Trimethyl chlorosilane (6.6 g, 55 mmol) was slowly added into the solution, and then the mixture was kept and stirred at low temperature for 1 hour, followed by slowly warming to room temperature and stirred overnight. After three times of water was added into reaction solution, the reaction solution was extracted by ethyl acetate. The organic layer was dried and evaporated to give a crude product which was used directly for the next step.

(2) Synthesis of 4-(dimethyl(vinyl)silyl)aniline (compound 6c)

At 0° C., 10 ml TFA was slowly added dropwise in the CH$_2$Cl$_2$ solution of compound 14. The reaction mixture was stirred at 0° C. for 2 hours. After adjusting pH to 8 by adding saturated Na HCO$_3$, the reaction mixture was extracted by ethyl acetate. The organic layer was dried and evaporated to give a crude product, which was purified using column chromatography to give the product (7 g, 72%).

(3) Synthesis of 4-(dimethyl(2-(piperidin-1-yl)ethyl) silyl)aniline (Compound 16)

At 50° C., n-butyl lithium (8 ml/L, 21 ml) was slowly added dropwise into the THF solution of piperidine (3.5 g, 41 mmol). After the solution was stirred at 50° C. for 30 minutes, compound 6c (0.6 g, 3.4 mmol) in THF was slowly added into the reaction mixture. After the reaction mixture was stirred at 50° C. for 2 hours, three times of water was added into the reaction solution, followed by extracted with ethyl acetate. The organic layer was dried and evaporated to give a crude product, which was purified using column chromatography to give the product.

2. Synthesis of N-(4-(dimethyl(2-(piperidin-1-yl) ethyl)silyl)phenyl)-4-(3-(trifluoromethyl)pyridine-2-yl)benzamide (compound A-22) according to the Synthetic Route on Scheme 8

Scheme 8

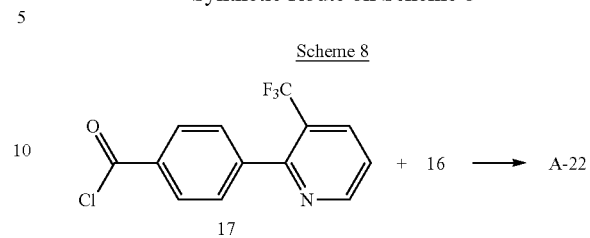

At 0°, C 4-(3-trifluoro methyl-2-pyridyl)benzoyl chloride (compound 17) (1.1 equivalent) was added into a solution of compound 16 (1 equivalent) and triethylamine (2 equivalent) in CH$_2$Cl$_2$. The reaction mixture was stirred at room temperature for 30 minutes. Reaction mixture was washed with aqueous hydrochloric acid, extracted with ethyl acetate and dried. The organic layer was evaporated to give a crude product, which was purified using column chromatography to give the product.

Using 1H NMR to identify compound A-22: $^1$H NMR (300 MHz, CDCl$_3$) δ8.9-8.8 (d, 1H), 8.2-8.1 (m, 2H), 8.0-7.9 (d, 2H), 7.7-7.6 (m, 4H), 7.6-7.4 (m, 3H), 2.5-2.2 (m, 6H), 1.7-1.5 (m, 4H), 1.5-1.4 (m, 2H), 1.1-1.0 (m, 2H), 0.3 (s, 9H).

MS: 512 (M+1)+.

Example 12

Synthesis of 4-(3-chloropyridin-2-yl)-N-(4-(dimethyl (2-(piperidin-1-yl)ethyl)silyl)phenyl)benzamide (compound A-24)

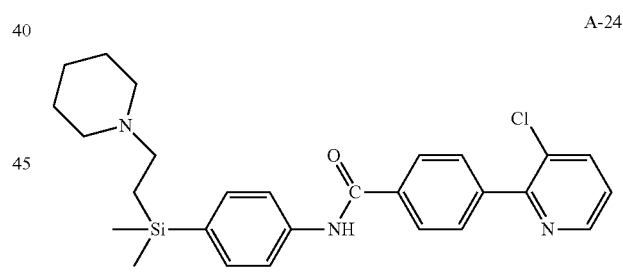

In this example, the synthesis of compound A-24 is similar to the synthesis of A-22 in example 11, just using 4-(3-chloropyridin-2-yl)benzoyl chloride (compound 18) to replace 4-(3-(trifluoromethyl)pyridin-2-yl)benzoyl chloride.

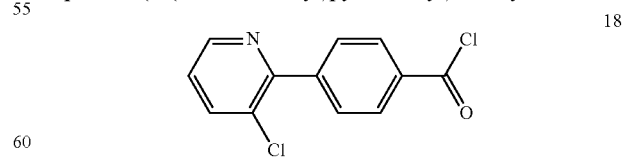

Using 1H NMR to identify compound A-24: $^1$H NMR (300 MHz, CDCl$_3$) δ8.6-8.5 (d, 1H), 8.1-8.0 (s, 1H), 8.0-7.9 (d, 2H), 7.9-7.8 (d, 3H), 7.7-7.6 (d, 2H), 7.6-7.5 (d, 2H), 7.3-7.2 (m, 1H), 2.5-2.3 (m, 6H), 1.7-1.5 (m, 4H), 1.5-1.4 (m, 2H), 1.1-1.0 (m, 2H), 0.3 (s, MS: 478 (M+1)$^+$

Example 13

Synthesis of 1-(3-chloropyridin-2-yl)-N-(4-(dimethyl (2-(piperidin-1-yl)ethyl)silyl)phenyl)-1,2,3,6-tetrahydropyridine-4-carboxamide (compound A-23)

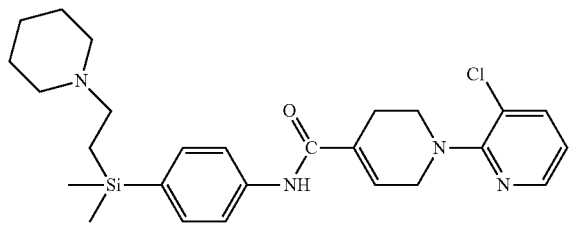

A-23

In this example, the synthesis of compound A-23 is similar to the synthesis of A-22 in example 11, just using 1-(3-chloropyridin-2-yl)-1,2,3,6-tetrahydropyridine-4-carbonyl chloride (compound 25 in Scheme 9) to replace 4-(3-(trifluoromethyl)pyridin-2-yl)benzoyl chloride (compound 17). And compound 25 can be synthesized using the synthetic route shown in Scheme 9.

1. Synthesis of 1-(3-chloropyridin-2-yl)piperidin-4-ol (Compound 20)

2,3-dichloropyridine (10 g, 68 mmol) and 5-hydroxyl piperidine (compound 19) (26 g, 272 mmol) in DMSO was heated at 120° C. and stirred overnight. After the reaction was completed, three times of water was added into the reaction solution. The reaction mixture was extracted by ethyl acetate. The organic layer was evaporated to give a crude product, which was purified using column chromatography to give the product. (17 g, 93%)

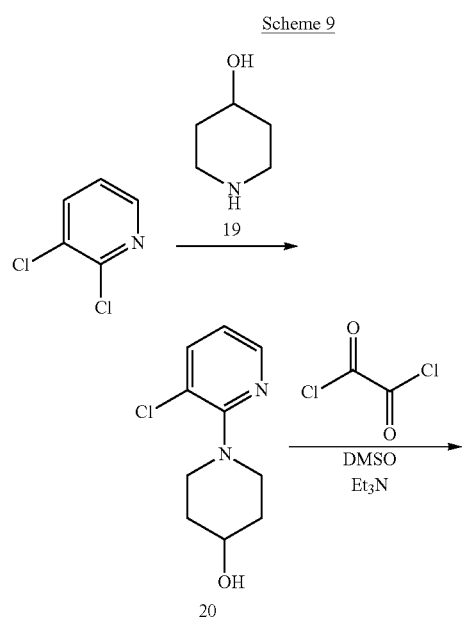

Scheme 9

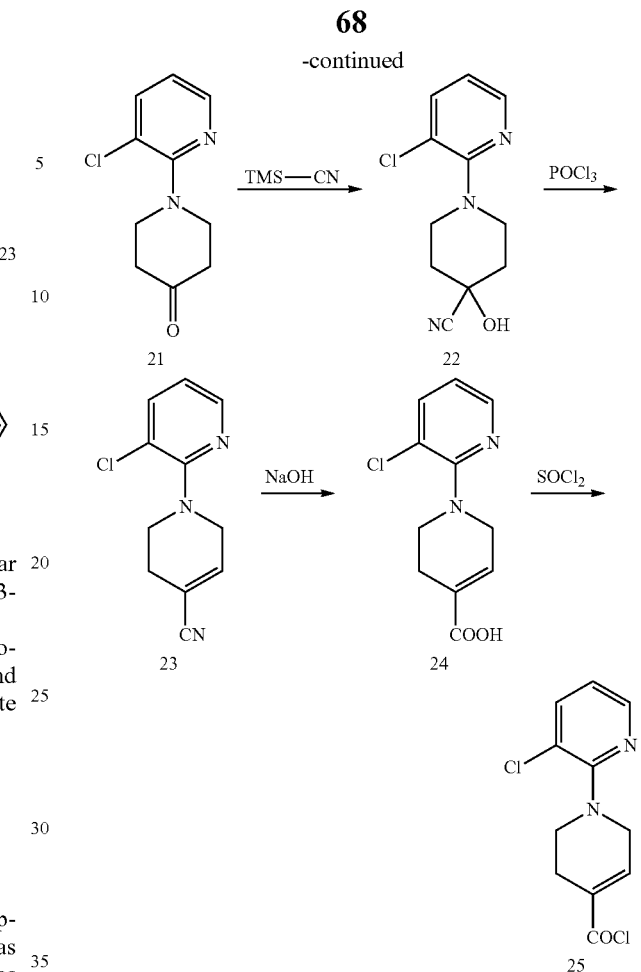

2. Synthesis of 1-(3-chloropyridin-2-yl)piperidin-4-one (Compound 21)

At −78° C., DMSO (10 g, 138 mmol) was added slowly into a dichloromethane (40 ml) solution of oxalyl dichloride. After 15 minutes, N-(3-chloro-2-pyridyl)-4-hydroxy piperidine (compound 20) in methylene chloride was added dropwise into the reaction mixture. After 30 minutes, 31 g of triethylamine was slowly added, when the reaction solution was maintained at −78° C. Reaction mixture was slowly warmed to room temperature. Three times of water was added into the reaction solution. The reaction mixture was extracted by ethyl acetate. The organic layer was evaporated to give a crude product, which was purified using column chromatography to give the product. (13 g, 93%)

3. Synthesis of 1-(3-chloropyridin-2-yl)-4-hydroxypiperidine-4-carbonitrile (Compound 22)

A solution of N-(3-chloro-2-pyridyl)-4-piperidone (compound 21) (13 g, 62 mmol), TMS-CN (6.2 g, 62 mmol) and AlCl₃ (0.1 g) in toluene (100 ml) was heated to 60° C., and stirred overnight. Then 0.1 equivalent of methanesulfonic acid was added, and the reaction mixture was heated to reflux for half an hour. After the reaction was completed, three times of water was added into the reaction solution. The reaction mixture was extracted by ethyl acetate. The organic layer was evaporated to give a crude product, which was purified using column chromatography to give the product. (8 g, 55%)

4. Synthesis of 1-(3-chloropyridin-2-yl)-1,2,3,6-tetrahydropyridine-4-carbonitrile (Compound 23)

At 0° C., phosphoryl trichloride (10 g, 68 mmol) was slowly added into a solution of 1-(3-chloropyridin-2-yl)-4-hydroxypiperidine-4-carbonitrile (compound 22) (8 g, 33 mmol) in pyridine. After stirred at RT for 30 minutes, the reaction was washed by a HCl solution, and extracted by ethyl acetate. The organic layer was evaporated to give a crude product, which was purified using column chromatography to give the product.

5. Synthesis of 1-(3-chloropyridin-2-yl)-1,2,3,6-tetrahydropyridine-4-carboxylic Acid (Compound 24)

A solution of 1-(3-chloropyridin-2-yl)-1,2,3,6-tetrahydropyridine-4-carbonitrile (compound 23) in 120 ml of NaOH (5 g, 125 mmol) water solution and methanol (20 ml) (V/V=1:1) was heated to reflux, and stirred overnight. The reaction was washed by a HCl solution in an ice bath, and extracted by ethyl acetate. The organic layer was evaporated to give a crude product, which was purified using column chromatography to give the product.

6. Synthesis of 1-(3-chloropyridin-2-yl)-1,2,3,6-tetrahydropyridine-4-carbonyl Chloride (Compound 25)

A solution of 1-(3-chloropyridin-2-yl)-1,2,3,6-tetrahydropyridine-4-carboxylic acid (compound 24) (8 g, 34 mmol) and thionyl chloride (12 g, 100 mmol) in benzene was refluxed for two hours. The solvent was evaporated to give a crude product, which can be directly used for the next step.

Using 1H NMR to identify compound A-23: $^1$H NMR (300 MHz, CDCl$_3$) δ 8.2-8.1 (d, 1H), 7.7-7.4 (m, 6H), 6.9-6.8 (m, 1H), 6.7 (s, 1H), 4.2-4.1 (m, 2H), 3.6-3.5 (m, 2H), 2.8-2.6 (m, 2H), 2.5-2.3 (m, 6H), 1.7-1.5 (m, 4H), 1.5-1.3 (m, 2H), 1.1-0.9 (m, 2H), 0.3 (s, 6H).
MS: 483 (M+1)$^+$

Example 14

Synthesis of 1-(3-chloropyridin-2-yl)-N-(4-(trimethylsilyl)phenyl)-1,2,3,6-tetrahydropyridine-4-carboxamide (compound A-05)

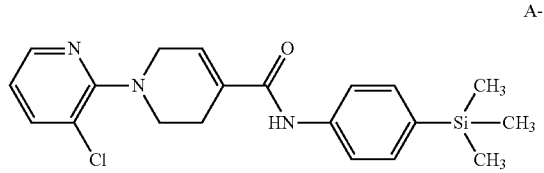

A-05

1-(3-chloropyridin-2-yl)-N-(4-(trimethylsilyl)phenyl)-1,2,3,6-tetrahydropyridine-4-carboxamide can be synthesized by the synthetic route shown in Scheme 10, and can be prepared using the method similar to the method 2 which was described in 2.2; The reaction of compound 24 (70 mg) and compound 6a gave 1-(3-chloropyridin-2-yl)-N-(4-(trimethylsilyl)phenyl)-1,2,3,6-tetrahydropyridine-4-carboxamide (80 mg, yield 70%). And compound 24 has been described in the example 13. The synthesis of compounds 6a has also been described in the method 1. To make it simple and clear, we won't repeat it here.

Scheme 10

24 + 6a ⟶

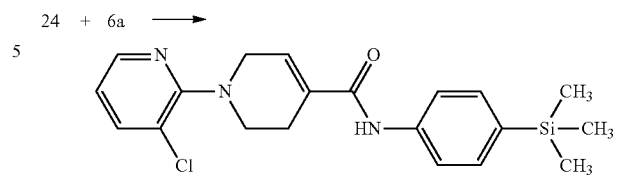

Using 1H NMR to identify compound A-05: 1H NMR (300 MHz, CDCl$_3$) 0.18 (m, 1H), 7.65-7.45 (m, 6H), 6.86-6.80 (m, 1H), 6.75 (s, 1H), 4.10-4.00 (m, 2H), 3.60-3.50 (t, 2H), 2.70-2.62 (m, 2H), 0.24 (s, 9H).

Example 15

Synthesis of 1-(3-chloropyridin-2-yl)-N-(3-((dimethylamino)methyl)-4-(trimethylsilyl)phenyl)-1,2,3,6-tetrahydropyridine-4-carboxamide (compound A-33)

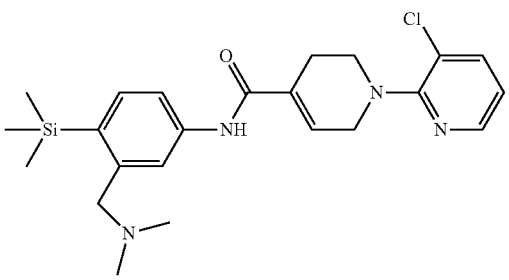

A-33

In this example, the synthesis of compound A-33 is similar to the synthetic method for compound A-23 in example 13, just using 3-((dimethylamino)methyl)-4-(trimethylsilyl)aniline (compound 30) to replace compound 16. And compound 30 can be synthesized by the synthetic route shown in Scheme 11.

Scheme 11

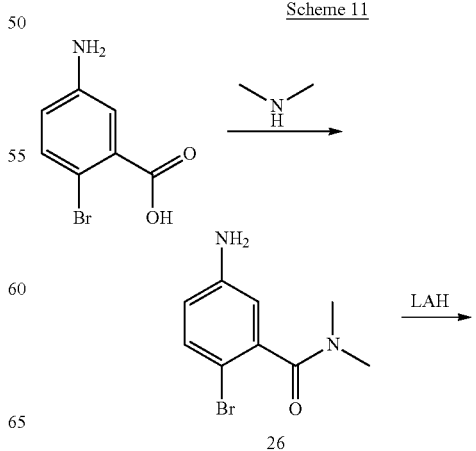

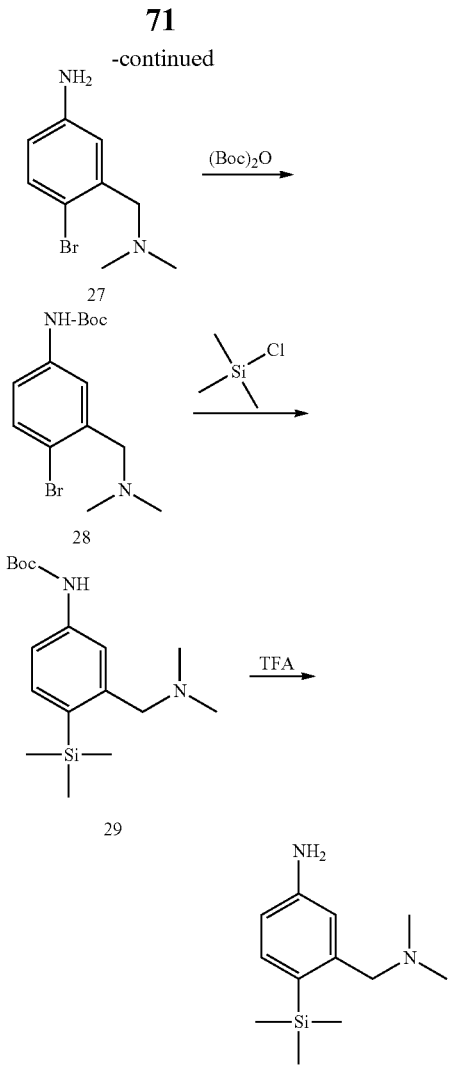

1. Synthesis of 5-amino-2-bromo-N,N-dimethylbenzamide (Compound 26)

Diisopropyl ethylamine (21 ml, 121 mmol) was dissolved in a solution of 5-amino-2-bromo benzoic acid (5 g, 23 mmol), dimethylamine (5 g, 115 mmol) and BOP (51 g, 121 mmol) in 100 ml DMF. And the reaction mixture was stirred at room temperature 30 minutes. Three times of water was added into the reaction solution. The reaction mixture was extracted by ethyl acetate. The organic layer was evaporated to give a crude product, which was purified using column chromatography to give the product. (3.1 g, 54%)

2. Synthesis of 4-bromo-3-((dimethylamino)methyl)aniline (Compound 27)

At 0° C., LAH (1.5 g 40 mmol) was added slowly in several portions into a suspension of 5-amino-2-bromo-N,N-dimethylbenzamide (compound 26) (3.1 g, 12.7 mmol) in THF. The reaction mixture was stirred at 0° C. for 2 hours. Then at 0° C. water was added dropwise to the reaction solution slowly until there was no bubble forming in the reaction. After ethyl acetate was added, the reaction mixture was stirred for 30 minutes. The mixture was filtered, washed three times with ethyl acetate. The solvent was evaporated to give a crude product, which can be directly used for the next step.

3. Synthesis of tert-butyl 4-bromo-3-((dimethylamino)methyl)phenylcarbamate (Compound 28)

(Boc)$_2$O (2.5 g, 11.5 mmol) was added into a solution of 4-bromo-3-((dimethylamino)methyl) aniline (compound 27) in CH$_2$Cl$_2$. The mixture was stirred at room temperature overnight. The solvent was evaporated to give a crude product, which can be directly used for the next step. (2.7 g, 87%)

4. Synthesis of tert-butyl 3-((dimethylamino)methyl)-4-(trimethylsilyl)phenylcarbamate (Compound 29)

At −78° C., n-butyl lithium (2.5 ml/L, 3 ml) was slowly added dropwise into a solution of tert-butyl 4-bromo-3-((dimethylamino)methyl)phenylcarbamate (compound 28) (2.7 g, 8 mmol) in THF. The reaction mixture was stirred at low-temperature for 30 minutes, followed by adding trimethylchlorosilane (1.1 g, 9.6 mmol). And then the reaction mixture was stirred at low-temperature for 1 hour. After the mixture was warmed to RT and stirred overnight, three times of water was added into the reaction solution. The reaction mixture was extracted by ethyl acetate. The solvent was dried and evaporated to give a crude product, which can be directly used for the next step.

5. Synthesis of 3-((dimethylamino)methyl)-4-(trimethylsilyl)aniline (Compound 30)

At 0° C., 5 ml TFA was slowly added into a solution of tert-butyl 3-((dimethylamino)methyl)-4-(trimethylsilyl)phenylcarbamate (compound 29) in CH$_2$Cl$_2$. The reaction mixture was stirred at 0° for 2 hours. After adjusted with saturated NaHCO$_3$ solution to pH 8, the reaction mixture was extracted by ethyl acetate. The organic layer was dried and evaporated to give a crude product, which was purified using column chromatography to give the product. (0.9 g, 32%)

Using 1H NMR to identify compound A-33: 1 H NMR (300 MHz, CDCl$_3$) δ 8.2-8.1 (d, 1H), 7.7-7.4 (m, 5H), 6.9-6.7 (m, 2H), 4.1-4.0 (m, 2H), 3.6-3.4 (m, 4H), 2.7-2.6 (m, 2H), 2.2 (s, 6H), 0.3 (s, 9H)

MS: 443 (M+1)$^+$

Example 16

Synthesis of 4-(3-chloropyridin-2-yl)-N-(3-((dimethylamino)methyl)-4-(trimethylsilyl)phenyl)benzamide (compound A-28)

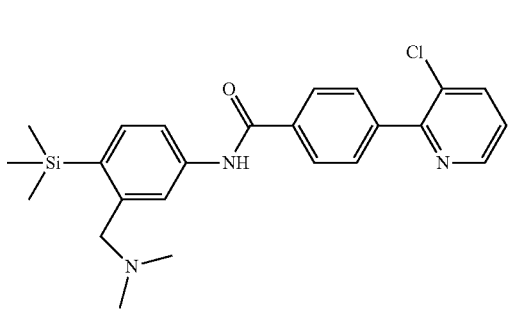

In this example, the synthesis of compound A-28 can be referred to the synthetic route of Scheme 12 and the synthetic method of compound A-22 in the example 11. And the synthesis of compound 30 can be referred to the example 15.

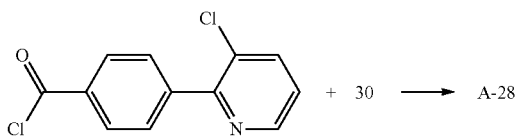

Using 1H NMR to identify compound A-28: $^1$H NMR (300 MHz, CDCl$_3$) δ 8.6-8.5 (d, 1H), 8.1 (s, 1H), 8.0-7.9 (d, 2H), 7.9-7.8 (m, 4H), 7.6-7.4 (m, 2H), 7.3-7.2 (m, 1H), 3.6 (s, 2H), 2.3 (s, 6H), 0.3 (s, 9H)

MS: 438 (M+1)$^+$

Example 17

Synthesis of 4-(3-(trifluoromethyl)pyridin-2-yl)-N-(5-(trimethylsilyl)pyridin-2-yl)benzamide (compound A-20)

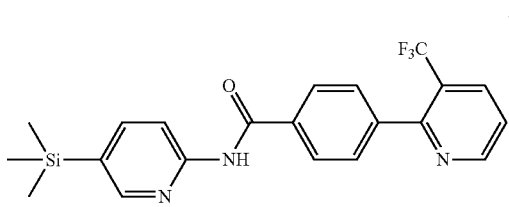

In this example, the synthetic method of compound A-20 is similar to the synthetic method of compound A-22 in the example 11, just using 5-(trimethylsilyl)pyridin-2-amine (compound 38) to replace compound 16. And compound 38 can be synthesized following the synthetic route in Scheme 13, and referring the synthesis of compound 15 in the example 11. (3 g, 55%).

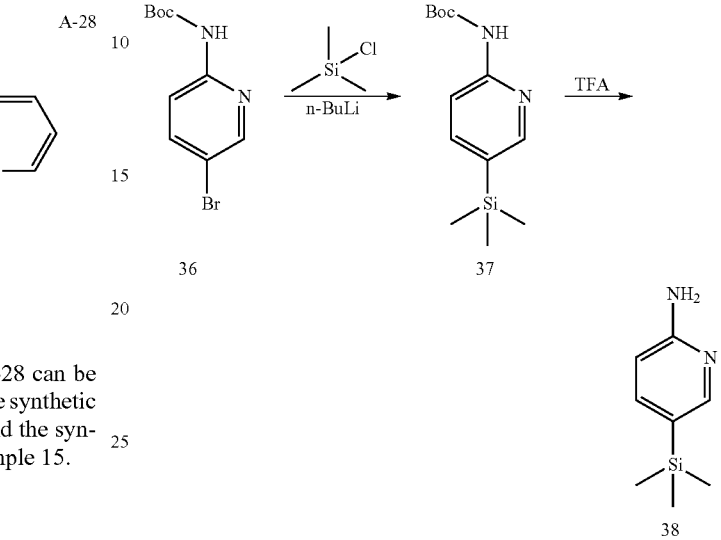

Using 1H NMR to identify compound A-20: $^1$H NMR (300 MHz, CDCl$_3$) δ 9.0-8.8 (m, 2H), 8.4-8.3 (m, 2H), 8.2-8.0 (m, 3H), 7.9-7.8 (d, 1H), 7.7-7.6 (d, 2H), 7.5-7.4 (m, 1H), 0.3 (s, 9H).

MS: 416 (M+1)$^+$

Example 18

Synthesis of 4-(3-chloropyridin-2-yl)-N-(3-(2-(dimethylamino)ethyl)-4-(trimethylsilyl)phenyl)benzamide (compound A-25)

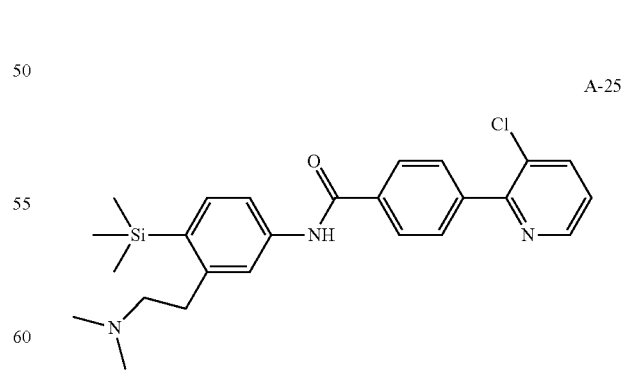

In this example, the synthetic method of compound A-25 is similar to the synthetic method of compound A-24 in the example 12, just using 3-(2-(dimethylamino)ethyl)-4-(trimethylsilyl)aniline (compound 44) to replace compound 16. And compound 44 can be synthesized following the synthetic route in Scheme 14, and referring the synthesis of compound 30 in the example 15. (4 g, 48%)

Using 1H NMR to identify compound A-25: 1H NMR (300 MHz, CDCl₃) δ 8.6-8.5 (d, 1H), 8.3 (s, 1H), 8.0-7.9 (d, 2H), (m, 3H), 7.6-7.4 (m, 3H), 7.3-7.2 (m, 1H), 3.0-2.8 (m, 2H), 2.6-2.5 (m, 2H), 2.3 (s, 6H), 0.3 (s, 9H).

MS: 452 (M+1)⁺

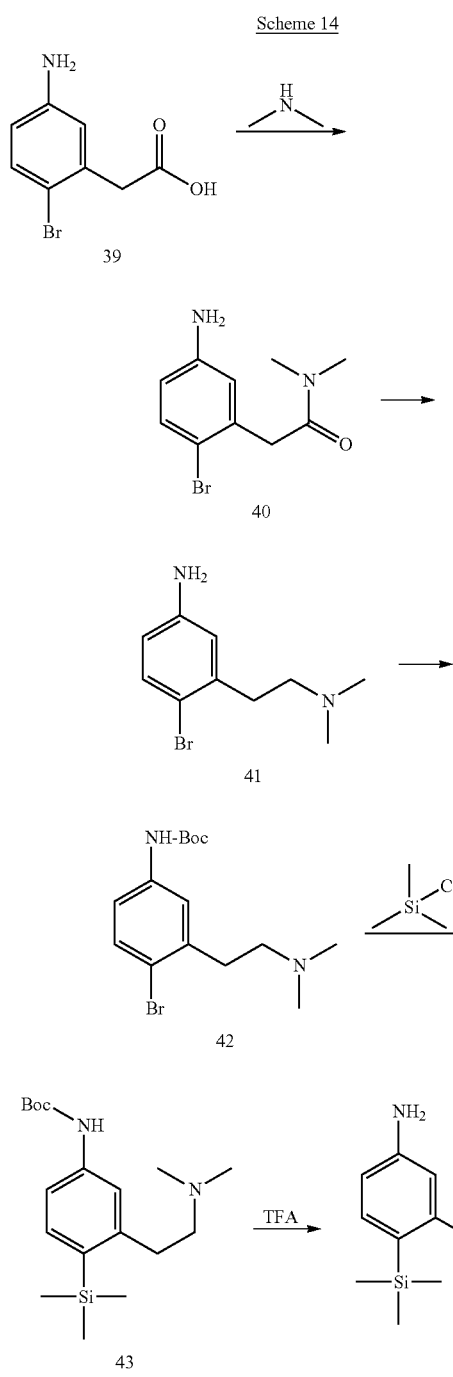

Scheme 14

Example 19

Synthesis of 4-(3-chloropyridin-2-yl)-N-(3-(2-(dimethylamino)ethyl)-4-(trimethylsilyl)phenyl)benzamide (compound A-26)

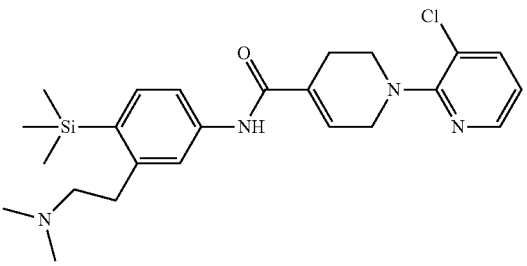

A-26

The synthetic method of compound A-26 is similar to the synthetic method of compound A-33 in the example 15, just using 3-(2-(dimethylamino)ethyl)-4-(trimethylsilyl)aniline (compound 44) to replace compound 30. And the synthesis of compound 44 can be referred to the example 18.

Using 1H NMR to identify compound A-26: 1H NMR (300 MHz, CDCl₃) δ 8.2-8.1 (d, 1H), 7.7-7.6 (d, 1H), 7.5-7.3 (m, 4H), 6.9-6.8 (m, 1H), 6.8-6.7 (s, 1H), 4.1-4.0 (m, 2H), 3.6-3.5 (m, 2H), 3.0-2.9 (m, 2H), 2.7-2.6 (m, 2H), 2.6-2.5 (m, 2H), 2.3 (s, 6H), 0.3 (s, 9H).

Example 20

Determination of In Vitro Activity

The functional activity of compounds at the TRPV1 receptor was determined using a Molecular Devices FLIPR based $Ca^{2+}$ influx assay, employing a $Ca^{2+}$ sensitive fluorescent dye and a CHO-K1 cell line, stably expressing recombinant human TRPV1, under the control of a CMV promoter (TRPV1.CHO cells). TRPV1.CHO cells were routinely maintained at 37° C./5% $CO_2$ in normal growth medium (Dulbecco's Modified Eagles medium (DMEM/NUT.M-DC.F-12 GLUTAMAX-1 (1:1) with PYRIDOXINE) supplemented with 10% fetalclone II serum and 0.4 mg/ml G418, (all Invitrogen).

Test compounds were prepared as 10 mM stock solution in DMSO and tested for activity over several log units (ranging $10^-$ M-100 pM). Serial dilutions (half-log dose response) were prepared in 100% DMSO with further dilutions in aqueous assay buffer to final assay concentration for $IC_{50}$ determination (1% DMSO final).

TRPV1.CHO cells were seeded (10,000 cells/well) in a 384 clear bottom plate (Costar) 24 hr prior to assay. Cells were maintained at 37° C./5% $CO_2$ in normal growth medium (Dulbecco's Modified Eagles medium (DMEM/NUT-.MIX.F-12 GLUTAMAX-1 (1:1) with PYRIDOXINE) supplemented with 10% fetalclone II serum. Prior to assay, growth medium was removed and cells were incubated with 25 μl/well 1× Calcium3 dye (Molecular devices) for 1 hr at room temperature. The 1× dye is prepared by diluting 2× Calcium3 dye 1:1 in TRPV1 assay buffer (160 mM NaCl, 4.5 mM KCl, 10 mM HEPES, 10 mM Glucose, 2 mM $CaCl_2$, 1 mM $MgCl_2$ and 0.5 mM Probenecid, pH7).

TRPV1 responses were assessed following addition, in the FLIPR, of 12.5 μl/well of test compound (to give appropriate final concentration) for 15 mins time followed by 12.5 μl/well of 120 nM capsaicin (agonist) in TRPV1 buffer to give a final concentration of capsaicin of 30 nM (~$EC_{80}$ concentration). $Ca^{2+}$ influx was assessed by measurement of fluorescence. Baseline fluorescence responses were measured for approximately 10 s prior to addition of capsaicin. Increases in fluorescence emission following capsaicin addition were measured for a further 110 s. Responses were recorded as Max-Min fluorescence. Antagonist induced inhibition of TRPV1 mediated increases in intracellular [$Ca^{2+}$] was assessed relative to wells on the same plate to which capsaicin was added in the absence of antagonist (i.e pre-incubation in buffer alone).

Based on the above method, the typical $IC_5$ Value of in vitro analysis of the compounds of the present invention is 1 μM or less. Such as $IC_{50}$ of compound A-01 is 0.5 nM; $IC_{50}$ of compound A-04 is 5.4 nM; $IC_{50}$ of compound A-05 is 2.3 nM.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

INDUSTRIAL APPLICATIONS

The invention provides such a new compound and its pharmaceutically acceptable salt or hydrate has medical use, and be used to treat diseases, such as the TRPV1-mediated disease and other diseases, such as inflammatory or neuropathic pain and the disease involving in sensory nerve function, and such as such as asthma, rheumatic arthritis, osteoarthritis, inflammatory bowel disease, allergic bowel disease, incontinence, ulcers, migraine and psoriasis.

What is claimed is:
1. A compound of Formula (I):

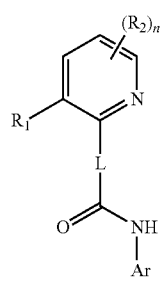

or any pharmaceutically-acceptable salt or hydrate thereof, wherein:
L is

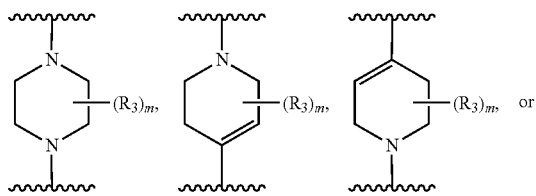

Ar is

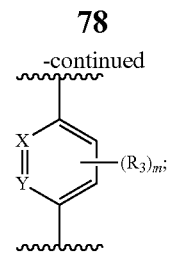

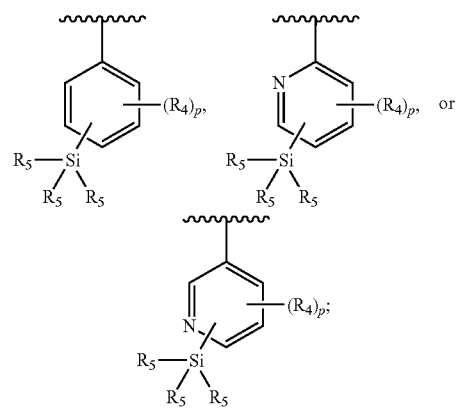

each X is independently N or C;
each Y is independently N or C;
m is 0, 1, 2, 3 or 4;
n is 0, 1, 2 or 3;
p is 0, 1, 2 or 3;
$R_1$ is —H, -halo, —($C_1$-$C_4$)alkyl, —$NO_2$, —CN, —$NH_2$, —C(halo)$_3$, CH(halo)$_2$, —$CH_2$(halo), —OC(halo)$_3$, —OCH(halo)$_2$ or —$OCH_2$(halo);
each $R_2$ is independently:
 (a) —H, halo OH, —O($C_1$-$C_4$)alkyl, —CN, —$NO_2$, or —$NH_2$;
 (b) —($C_1$-$C_{10}$)alkyl, —($C_2$-$C_{10}$)alkenyl, or —($C_2$-$C_{10}$) alkynyl;
 (c) -phenyl, each of which is unsubstituted or substituted with 1, 2 or 3 independently selected $R_7$ groups; or
 (d) a group of Formula Q; wherein Q is

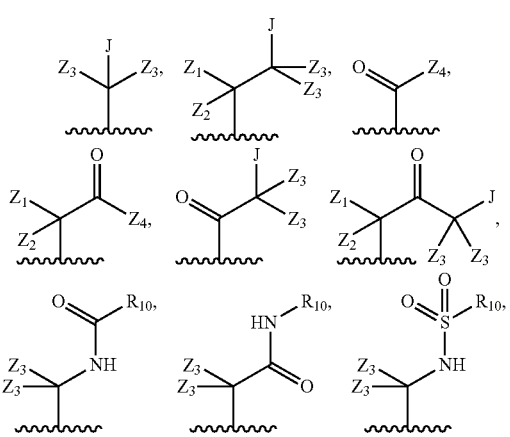

-continued

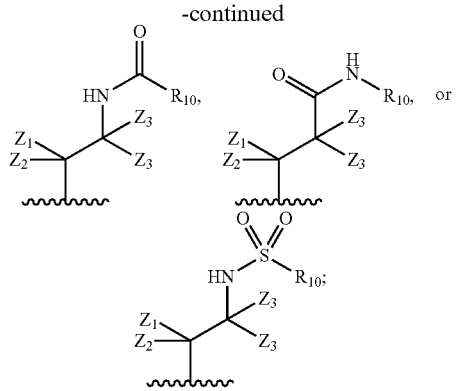

of which:
Z$_1$ is H, OR$_7$, SR$_7$, CH$_2$—OR$_7$, CH$_2$—SR$_7$, CH$_2$—N(R$_{10}$)$_2$, or halo;
Z$_2$ is H, (C$_1$-C$_6$)alkyl, (C$_2$-C$_6$)alkenyl, (C$_2$-C$_6$)alkynyl, CH$_2$—OR$_7$, phenyl, or halo;
each Z$_3$ is independently H, (C$_1$-C$_6$)alkyl, (C$_2$-C$_6$)alkenyl, (C$_2$-C$_6$)alkynyl, or phenyl;
Z$_4$ is H, OH, OR$_{10}$, (C$_1$-C$_6$)alkyl, or N(R$_{10}$)$_2$;
J is OR$_{10}$, SR$_{10}$, N(R$_{10}$)$_2$ or CN;
each R$_3$ is independently
  (a) —H, CH$_2$—OR$_7$, (C$_1$-C$_6$)alkyl, halo, CN, OH, NO$_2$, or NH$_2$;
  (b) two R$_3$ groups together form a (C$_2$-C$_6$)bridge, which is unsubstituted or substituted with 1, 2 or 3 independently selected R$_4$ groups, and which bridge optionally contains —HC═CH— within the (C$_2$-C$_6$)bridge; or
  (c) two R$_3$ groups together form a —CH$_2$—N(R$_a$)—CH$_2$— bridge, a

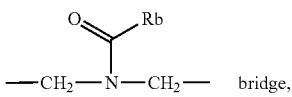 bridge, or a

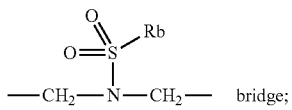 bridge;

wherein
R$_a$ is —H, (C$_1$-C$_6$)alkyl, (C$_3$-C$_8$)cycloalkyl, —CH$_2$—C(O)—R$_c$, —CH$_2$—C(O)—OR$_c$, —CH$_2$—C(O)—N(R$_c$)$_2$, —(CH$_2$)$_2$—O—R$_c$, —(CH$_2$)$_2$—S(O)$_2$—N(R$_c$)$_2$, or —(CH$_2$)$_2$—N(R$_c$)S(O)$_2$R$_c$;
each R$_b$ is independently:
  (a) —H, (C$_1$-C$_6$)alkyl, (C$_3$-C$_8$)cycloalkyl, —N(R$_c$)$_2$, or N(R$_c$)—(C$_3$-C$_8$)cycloalkyl;
  (b) phenyl, pyridyl, or naphthyl, each of which is unsubstituted or substituted with 1, 2 or 3 independently selected R$_7$ groups;
each R$_c$ is independently —H or (C$_1$-C$_4$)alkyl;
each R$_4$ is independently:
  (a) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is optionally substituted with 1 or 2 hydroxy groups;
  (b) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is substituted with 1 or 2 R$_d$; or
  (c) —H, CH$_2$C(halo)$_3$, C(halo)$_3$, CH(halo)$_2$, CH$_2$(halo), OC(halo)$_3$, OCH(halo)$_2$, OCH$_2$(halo), SC(halo)$_3$, SCH(halo)$_2$, SCH$_2$(halo), CN, OH, halo, N$_3$, NO$_2$, NH$_2$, CH═NR$_7$, N(R$_7$)$_2$, NR$_7$OH, OR$_7$, C(O)R$_7$, C(O)OR$_7$, OC(O)OR$_7$, SR$_7$, S(O)R$_7$, S(O)$_2$R$_7$, or —R$_7$;
each R$_d$ is independently:
  (a) N(R$_7$)$_2$, NR$_7$OH, OR$_7$, C(O)R$_7$, C(O)OR$_7$, OC(O)OR$_7$, SR$_7$, S(O)R$_7$, S(O)$_2$R$_7$; or
  (b)

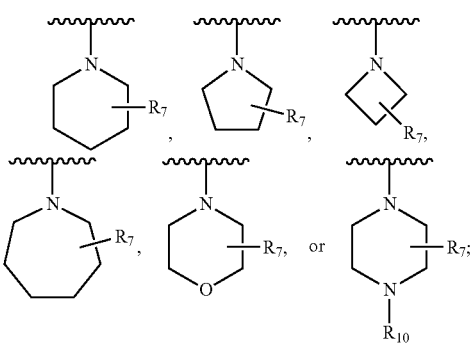

each R$_5$ is independently:
  (a) —H, halo, (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is optionally substituted with 1 or 2 hydroxy groups; or
  (b) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is substituted by 1 or 2 substituents independently selected from:
    (i) CH$_2$C(halo)$_3$, C(halo)$_3$, CH(halo)$_2$, CH$_2$(halo), OC(halo)$_3$, OCH(halo)$_2$, OCH$_2$(halo), SC(halo)$_3$, SCH(halo)$_2$, SCH$_2$(halo), CN, OH, halo, N$_3$, NO$_2$, NH$_2$, CH═NR$_7$, N(R$_7$)$_2$, NR$_7$OH, OR$_7$, C(O)R$_7$, C(O)OR$_7$, OC(O)OR$_7$, SR$_7$, S(O)R$_7$, or S(O)$_2$R$_7$; or
    (ii)

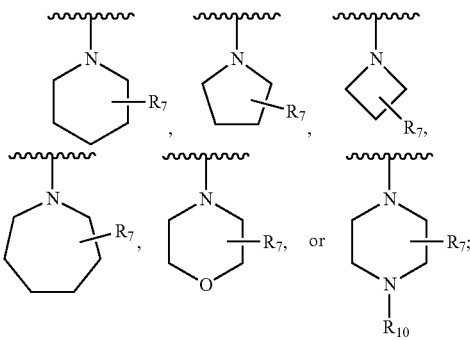

R$_7$ is —H, (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, phenyl, (C$_1$-C$_6$)haloalkyl, (C$_1$-C$_6$)hydroxyalkyl, (C$_1$-C$_6$)alkoxy(C$_1$-C$_6$)alkyl, (C$_1$-C$_6$)alkyl-N(R$_{10}$)$_2$, or CON(R$_{10}$)$_2$; and
R$_{10}$ is —H, (C$_1$-C$_4$)alkyl, (C$_1$-C$_4$)haloalkyl, (C$_1$-C$_4$)hydroxyalkyl, or (C$_1$-C$_4$)alkoxy(C$_1$-C$_4$)alkyl.

2. The compound of claim 1 having formula (II):

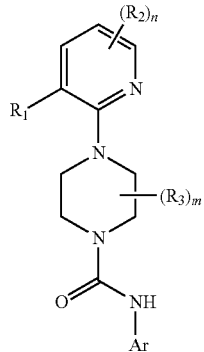

(II)

or any pharmaceutically-acceptable salt or hydrate thereof, wherein:

Ar is

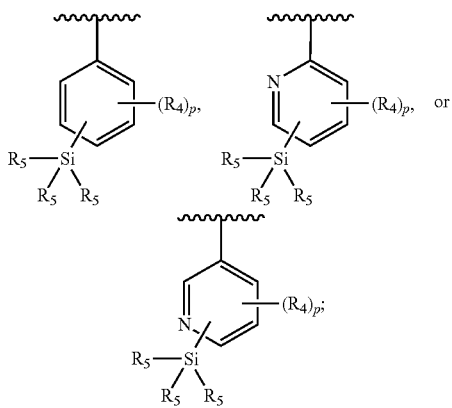

m is 0, 1, 2, 3 or 4;
n is 0, 1, 2 or 3;
p is 0, 1, 2 or 3;
$R_1$ is —H, -halo, —$(C_1\text{-}C_4)$alkyl, —$NO_2$, —CN, —$NH_2$—C(halo)$_3$, —CH(halo)$_2$, —$CH_2$(halo), OC(halo)$_3$, —OCH(halo)$_2$ or OCH$_2$(halo);

each $R_2$ is independently:
 (a) —H, -halo, —OH, —O$(C_1\text{-}C_4)$alkyl, —CN, —$NO_2$, or —$NH_2$;
 (b) —$(C_1\text{-}C_{10})$alkyl, —$(C_2\text{-}C_{10})$alkenyl, or —$(C_2\text{-}C_{10})$alkynyl;
 (c) -phenyl, each of which is unsubstituted or substituted with 1, 2 or 3 independently selected $R_7$ groups; or
 (d) a group of Formula Q, wherein Q is

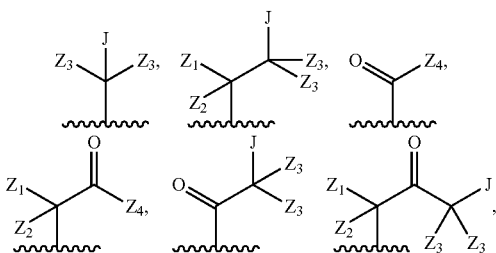

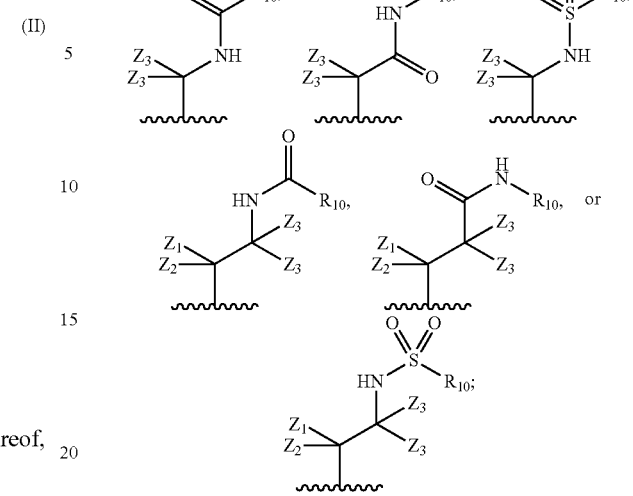

wherein:
 $Z_1$ is H, $OR_7$, $SR_7$, $CH_2$—$OR_7$, $CH_2$—$SR_7$, $CH_2$—$N(R_{10})_2$, or halo;
 $Z_2$ is H, $(C_1\text{-}C_6)$alkyl, $(C_2\text{-}C_6)$alkenyl, $(C_2\text{-}C_6)$alkynyl, $CH_2$—$OR_7$, phenyl, or halo;
 each $Z_3$ is independently H, $(C_1\text{-}C_6)$alkyl, $(C_2\text{-}C_6)$alkenyl, $(C_2\text{-}C_6)$alkynyl, or phenyl;
 $Z_4$ is H, OH, $OR_{10}$, $(C_1\text{-}C_6)$alkyl, or $N(R_{10})_2$;
 J is $OR_{10}$, $SR_{10}$, $N(R_{10})_2$ or CN;

each $R_3$ is independently
 (a) —H, $CH_2$—$OR_7$, $(C_1\text{-}C_6)$alkyl, halo, CN, OH, $NO_2$, or $NH_2$;
 (b) two $R_3$ groups together form a $(C_2\text{-}C_6)$bridge, which is unsubstituted or substituted with 1, 2 or 3 independently selected $R_4$ groups, and which bridge optionally contains —HC=CH— within the $(C_2\text{-}C_6)$bridge; or
 (c) two $R_3$ groups together form a —$CH_2$—$N(R_a)$—$CH_2$— bridge, a

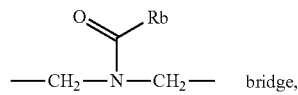 bridge, or a

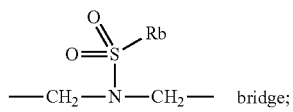 bridge;

wherein
 $R_a$ is —H, $(C_1\text{-}C_6)$alkyl, $(C_3\text{-}C_8)$cycloalkyl, —$CH_2$—C(O)—$R_c$, —$CH_2$—C(O)—$OR_c$, —$CH_2$—C(O)—$N(R_c)_2$, —$(CH_2)_2$—O—$R_c$, —$(CH_2)_2$—$S(O)_2$—$N(R_c)_2$, or —$(CH_2)_2$—$N(R_c)S(O)_2$—$R_c$;
 each $R_b$ is independently:
 (a) —H, $(C_1\text{-}C_6)$alkyl, $(C_3\text{-}C_8)$cycloalkyl, —$N(R_c)_2$, or $N(R_c)$—$(C_3\text{-}C_8)$cycloalkyl;
 (b) phenyl, pyridyl, or naphthyl, each of which is unsubstituted or substituted with 1, 2 or 3 independently selected $R_7$ groups;

each $R_c$ is independently —H or $(C_1-C_4)$alkyl;
each $R_4$ is independently:
(a) $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is optionally substituted with 1 or 2 hydroxy groups;
(b) $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is substituted with 1 or 2 $R_d$; or
(c) —H, $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, $CH=NR_7$, $N(R_7)_2$, $NR_7OH$, $OR_7$, $C(O)R_7$, $C(O)OR_7$, $OC(O)OR_7$, $SR_7$, $S(O)R_7$, $S(O)_2R_7$, or —$R_7$;

each $R_d$ is independently:
(a) $N(R_7)_2$, $NR_7OH$, $OR_7$, $C(O)R_7$, $C(O)OR_7$, $OC(O)OR_7$, $SR_7$, $S(O)R_7$, $S(O)_2R_7$; or
(b)

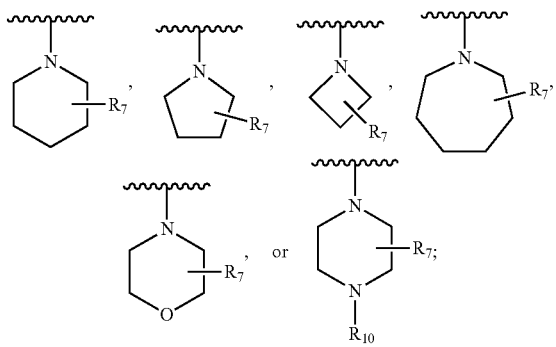

each $R_5$ is independently:
(a) —H, halo, $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is optionally substituted with 1 or 2 hydroxy groups; or
(b) $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is substituted by 1 or 2 substituents independently selected from:
(i) $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, $CH=NR_7$, $N(R_7)_2$, $NR_7OH$, $OR_7$, $C(O)R_7$, $C(O)OR_7$, $OC(O)OR_7$, $SR_7$, $S(O)R_7$, or $S(O)_2R_7$; or
(ii)

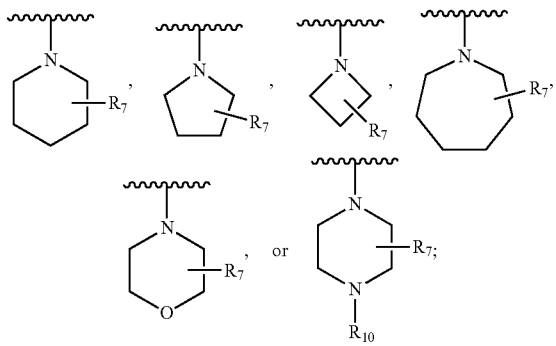

wherein:
$R_7$ is —H, $(C_1-C_6)$alkyl, $(C_2-C_6)$alkenyl, $(C_2-C_6)$alkynyl, $(C_3-C_8)$cycloalkyl, $(C_5-C_8)$cycloalkenyl, phenyl, $(C_1-C_6)$haloalkyl, $(C_1-C_6)$hydroxyalkyl, $(C_1-C_6)$alkoxy$(C_1-C_6)$alkyl, $(C_1-C_6)$alkyl-$N(R_{10})_2$, or $CON(R_{10})_2$; $R_{10}$ is —H, $(C_1-C_4)$alkyl, $(C_1-C_4)$haloalkyl, $(C_1-C_4)$hydroxyalkyl, or $(C_1-C_4)$alkoxy$(C_1-C_4)$alkyl.

3. The compound of claim 1 having formula (III):

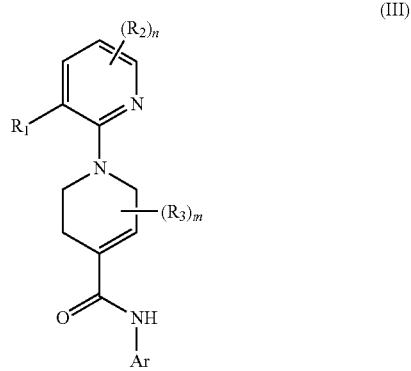

(III)

or any pharmaceutically-acceptable salt or hydrate thereof, wherein:
Ar is

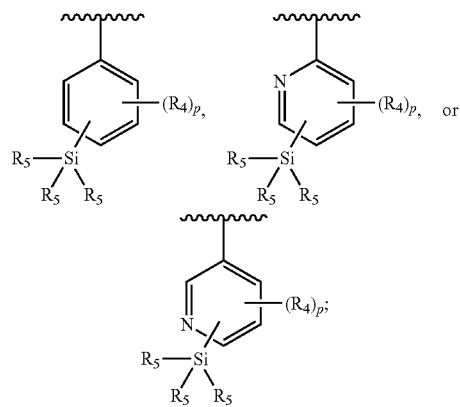

m 0, 1, 2, 3 or 4;
n is 0, 1, 2 or 3;
p is 0, 1, 2 or 3;
$R_1$ is —H, -halo, —$(C_1-C_4)$alkyl, —$NO_2$, —CN, —$NH_2$, —$C(halo)_3$, —$CH(halo)_2$, —$CH_2(halo)$, —$OC(halo)_3$, —$OCH(halo)_2$ or —$OCH_2(halo)$;
each $R_2$ is independently:
(a) —H, -halo, —OH, —$O(C_1-C_4)$alkyl, —CN, —$NO_2$, or —$NH_2$;
(b) —$(C_1-C_{10})$alkyl, —$(C_2-C_{10})$alkenyl, or —$(C_2-C_{10})$alkynyl;
(c) -phenyl, each of which is unsubstituted or substituted with 1, 2 or 3 independently selected $R_7$ groups; or
(d) a group of Formula Q; wherein Q is

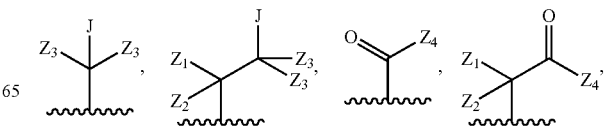

-continued

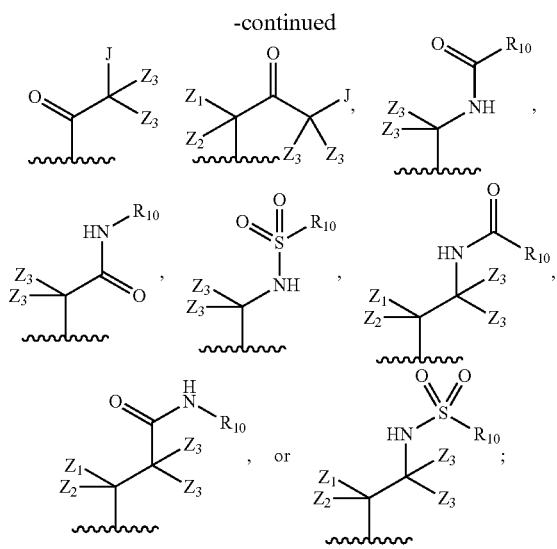

wherein:
Z$_1$ is H, OR$_7$, SR$_7$, CH$_2$—OR$_7$, CH$_2$—SR$_7$, CH$_2$—N(R$_{10}$)$_2$, or halo;
Z$_2$ is H, (C$_1$-C$_6$)alkyl, (C$_2$-C$_6$)alkenyl, (C$_2$-C$_6$)alkynyl, CH$_2$—OR$_7$, phenyl, or halo;
each Z$_3$ is independently H, (C$_1$-C$_6$)alkyl, (C$_2$-C$_6$)alkenyl, (C$_2$-C$_6$)alkynyl, or phenyl;
Z$_4$ is H, OH, OR$_{10}$, (C$_1$-C$_6$)alkyl, or N(R$_{10}$)$_2$;
J is OR$_{10}$, SR$_{10}$, N(R$_{10}$)$_2$ or CN;
each R$_3$ is independently
(a) —H, CH$_2$—OR$_7$, (C$_1$-C$_6$)alkyl, halo, CN, OH, NO$_2$, or NH$_2$;
(b) two R$_3$ groups together form a (C$_2$-C$_6$)bridge, which is unsubstituted or substituted with 1, 2 or 3 independently selected R$_4$ groups, and which bridge optionally contains —HC═CH— within the (C$_2$-C$_6$)bridge; or
(c) two R$_3$ groups together form a —CH$_2$—N(R$_a$)—CH$_2$— bridge, a

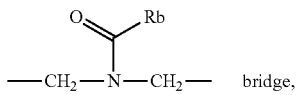

or a

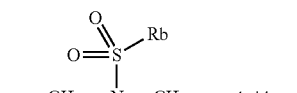

wherein
R$_a$ is —H, (C$_1$-C$_6$)alkyl, (C$_3$-C$_8$)cycloalkyl, —CH$_2$—C(O)—R$_c$, —CH$_2$—C(O)—OR$_c$, —CH$_2$—C(O)—N(R$_c$)$_2$, —(CH$_2$)$_2$—O—R$_c$, —(CH$_2$)$_2$—S(O)$_2$—N(R$_c$)$_2$, or —(CH$_2$)$_2$—N(R$_c$)S(O)$_2$—R$_c$;
each R$_b$ is independently:
(a) —H, (C$_1$-C$_6$)alkyl, (C$_3$-C$_8$)cycloalkyl, —N(R$_c$)$_2$, or N(R$_c$)—(C$_3$-C$_8$)cycloalkyl;
(b) phenyl, pyridyl, or naphthyl, each of which is unsubstituted or substituted with 1, 2 or 3 independently selected R$_7$ groups;
each R$_c$ is independently —H or (C$_1$-C$_4$)alkyl;

each R$_4$ is independently:
(a) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is optionally substituted with 1 or 2 hydroxy groups;
(b) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is substituted with 1 or 2 R$_d$; or
(c) —H, CH$_2$C(halo)$_3$, C(halo)$_3$, CH(halo)$_2$, CH$_2$(halo), OC(halo)$_3$, OCH(halo)$_2$, OCH$_2$(halo), SC(halo)$_3$, SCH(halo)$_2$, SCH$_2$(halo), CN, OH, halo, N$_3$, NO$_2$, NH$_2$, CH═NR$_7$, N(R$_7$)$_2$, NR$_7$OH, OR$_7$, C(O)R$_7$, C(O)OR$_7$, OC(O)OR$_7$, SR$_7$, S(O)R$_7$, S(O)$_2$R$_7$, or —R$_7$;
each R$_d$ is independently:
(a) N(R$_7$)$_2$, NR$_7$OH, OR$_7$, C(O)R$_7$, C(O)OR$_7$, OC(O)OR$_7$, SR$_7$, S(O)R$_7$, S(O)$_2$R$_7$; or
(b)

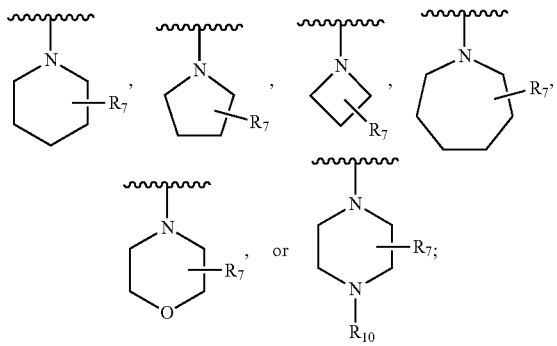

each R$_5$ is independently:
(a) —H, halo, (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is optionally substituted with 1 or 2 hydroxy groups; or
(b) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is substituted by 1 or 2 substituents independently selected from:
(i) CH$_2$C(halo)$_3$, C(halo)$_3$, CH(halo)$_2$, CH$_2$(halo), OC(halo)$_3$, OCH(halo)$_2$, OCH$_2$(halo), SC(halo)$_3$, SCH(halo)$_2$, SCH$_2$(halo), CN, OH, halo, N$_3$, NO$_2$, NH$_2$, CH═NR$_7$, N(R$_7$)$_2$, NR$_7$OH, OR$_7$, C(O)R$_7$, C(O)OR$_7$, OC(O)OR$_7$, SR$_7$, S(O)R$_7$, or S(O)$_2$R$_7$; or
(ii)

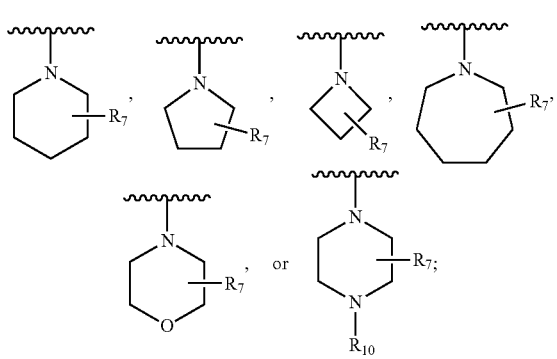

wherein:
R$_7$ is —H, (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, phenyl, (C$_1$-

$C_6$)haloalkyl, ($C_1$-$C_6$)hydroxyalkyl, ($C_1$-$C_6$)alkoxy($C_1$-$C_6$)alkyl, ($C_1$-$C_6$)alkyl-$N(R_{10})_2$, or $CON(R_{10})_2$; and
$R_{10}$ is —H, ($C_1$-$C_4$)alkyl, ($C_1$-$C_4$)haloalkyl, ($C_1$-$C_4$)hydroxyalkyl, or ($C_1$-$C_4$)alkoxy($C_1$-$C_4$)alkyl.

4. The compound of claim 1 having formula (IV):

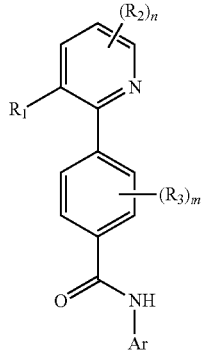

(IV)

or any pharmaceutically-acceptable salt or hydrate thereof, wherein:

Ar is

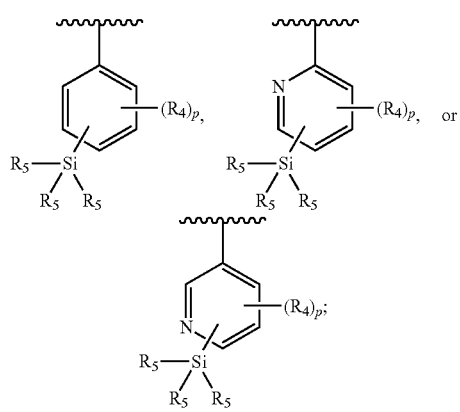

m 0, 1, 2, 3 or 4;
n is 0, 1, 2 or 3;
p is 0, 1, 2 or 3;
$R_1$ is —H, -halo, —($C_1$-$C_4$)alkyl, —$NO_2$, —CN, —$NH_2$, —C(halo)$_3$, —CH(halo)$_2$, —$CH_2$(halo), —OC(halo)$_3$, —OCH(halo)$_2$ or $OCH_2$(halo);
each $R_2$ is independently:
(a) —H, -halo, —OH, —O($C_1$-$C_4$)alkyl, —CN, —$NO_2$, or —$NH_2$;
(b) —($C_1$-$C_{10}$)alkyl, —($C_2$-$C_{10}$)alkenyl, or —($C_2$-$C_{10}$)alkynyl;
(C) -phenyl, each of which is unsubstituted or substituted with 1, 2 or 3 independently selected $R_7$ groups; or
(d) a group of Formula Q; wherein Q is:

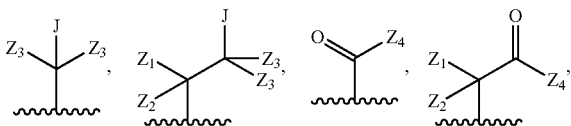

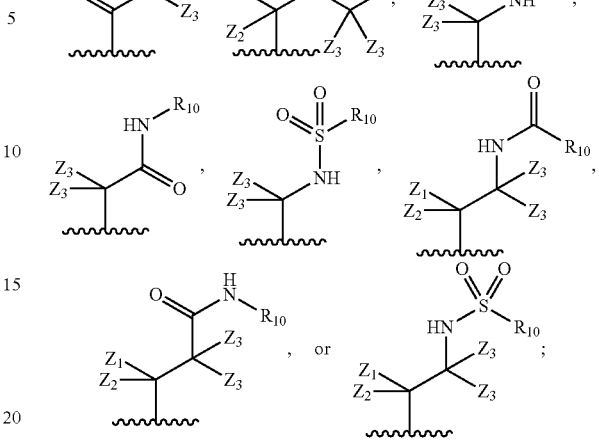

wherein:
$Z_1$ is H, $OR_7$, $SR_7$, $CH_2$—$OR_7$, $CH_2$—$SR_7$, $CH_2$—$N(R_{10})_2$, or halo;
$Z_2$ is H, ($C_1$-$C_6$)alkyl, ($C_2$-$C_6$)alkenyl, ($C_2$-$C_6$)alkynyl, $CH_2$—$OR_7$, phenyl, or halo;
each $Z_3$ is independently H, ($C_1$-$C_6$)alkyl, ($C_2$-$C_6$)alkenyl, ($C_2$-$C_6$)alkynyl, or phenyl;
$Z_4$ is H, OH, $OR_{10}$, ($C_1$-$C_6$)alkyl, or $N(R_{10})_2$;
J is $OR_{10}$, $SR_{10}$, $N(R_{10})_2$ or CN;
each $R_3$ is independently
(a) —H, $CH_2$—$OR_7$, ($C_1$-$C_6$)alkyl, halo, CN, OH, $NO_2$, or $NH_2$;
(b) two $R_3$ groups together form a ($C_2$-$C_6$)bridge, which is unsubstituted or substituted with 1, 2 or 3 independently selected $R_4$ groups, and which bridge optionally contains —HC=CH— within the ($C_2$-$C_6$)bridge; or
(c) two $R_3$ groups together form a —$CH_2$—N($R_a$)—$CH_2$— bridge, a —$CH_2$—N(C(O)Rb)—$CH_2$— bridge, or a —$CH_2$—N(S(O)$_2$Rb)—$CH_2$— bridge;

wherein
$R_a$ is —H, ($C_1$-$C_6$)alkyl, ($C_3$-$C_8$)cycloalkyl, —$CH_2$—C(O)—$R_c$, —$CH_2$—C(O)—$OR_c$, —$CH_2$—C(O)—N($R_c$)$_2$, —($CH_2$)$_2$—O—$R_c$, —($CH_2$)$_2$—$S(O)_2$—N($R_c$)$_2$, or —($CH_2$)$_2$—N($R_c$)$S(O)_2$—$R_c$;
each $R_b$ is independently:
(a) —H, ($C_1$-$C_6$)alkyl, ($C_3$-$C_8$)cycloalkyl, —N($R_c$)$_2$, or N($R_c$)—($C_3$-$C_8$)cycloalkyl;
(b) phenyl, pyridyl, or naphthyl, each of which is unsubstituted or substituted with 1, 2 or 3 independently selected $R_7$ groups;
each $R_c$ is independently —H or ($C_1$-$C_4$)alkyl;

each R$_4$ is independently:
(a) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is optionally substituted with 1 or 2 hydroxy groups;
(b) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is substituted with 1 or 2 R$_d$; or
(c) —H, CH$_2$C(halo)$_3$, C(halo)$_3$, CH(halo)$_2$, CH$_2$(halo), OC(halo)$_3$, OCH(halo)$_2$, OCH$_2$(halo), SC(halo)$_3$, SCH(halo)$_2$, SCH$_2$(halo), CN, OH, halo, N$_3$, NO$_2$, NH$_2$, CH=NR$_7$, N(R$_7$)$_2$, NR$_7$OH, OR$_7$, C(O)R$_7$, C(O)OR$_7$, OC(O)OR$_7$, SR$_7$, S(O)R$_7$, S(O)$_2$R$_7$, or —R$_7$;

each R$_d$ is independently:
(a) N(R$_7$)$_2$, NR$_7$OH, OR$_7$, C(O)R$_7$, C(O)OR$_7$, OC(O)OR$_7$, SR$_7$, S(O)R$_7$, S(O)$_2$R$_7$; or
(b)

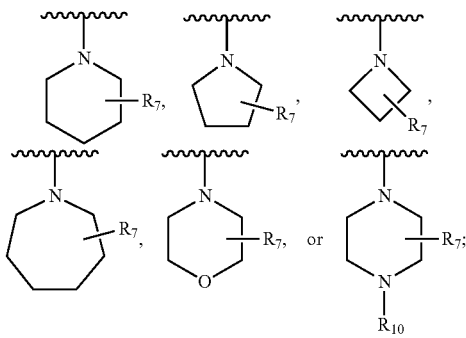

each R$_5$ is independently:
(a) —H, halo, (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is optionally substituted with 1 or 2 hydroxy groups; or
(b) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is substituted by 1 or 2 substituents independently selected from:
(i) CH$_2$C(halo)$_3$, C(halo)$_3$, CH(halo)$_2$, CH$_2$(halo), OC(halo)$_3$, OCH(halo)$_2$, OCH$_2$(halo), SC(halo)$_3$, SCH(halo)$_2$, SCH$_2$(halo), CN, OH, halo, N$_3$, NO$_2$, NH$_2$, CH=NR$_7$, N(R$_7$)$_2$, NR$_7$OH, OR$_7$, C(O)R$_7$, C(O)OR$_7$, OC(O)OR$_7$, SR$_7$, S(O)R$_7$, or S(O)$_2$R$_7$; or
(ii)

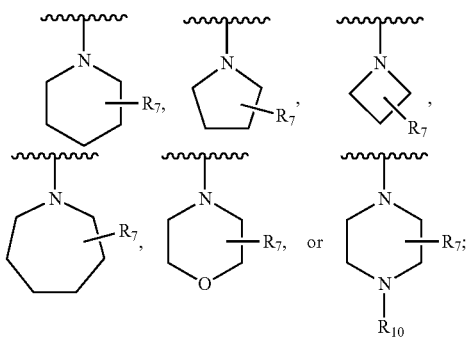

R$_7$ is —H, (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, phenyl, (C$_1$-C$_6$)haloalkyl, (C$_1$-C$_6$)hydroxyalkyl, (C$_1$-C$_6$)alkoxy(C$_1$-C$_6$)alkyl, (C$_1$-C$_6$)alkyl-N(R$_{10}$)$_2$, or CON(R$_{10}$)$_2$; and R$_{10}$ is —H, (C$_1$-C$_4$)alkyl, (C$_1$-C$_4$)haloalkyl, (C$_1$-C$_4$)hydroxyalkyl, or (C$_1$-C$_4$)alkoxy(C$_1$-C$_4$)alkyl.

5. The compound according to claim 1, wherein R$_5$ is methyl.

6. The compound according to claim 5, wherein R$_2$ is:

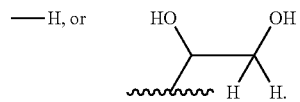

7. The compound according to claim 6, wherein R$_1$ is -halo, methyl, —CF$_3$.

8. The compound according to claim 1, wherein R$_2$ is:

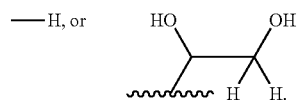

9. The compound according to claim 8, wherein R$_2$ is:

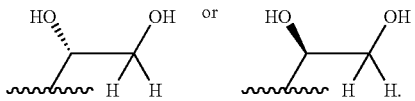

10. The compound according to claim 8, wherein R$_1$ is -halo, methyl, —CF$_3$.

11. The compound according to claim 1, wherein R$_1$ is -halo, methyl, —CF$_3$.

12. The compound of claim 2 having formula (V):

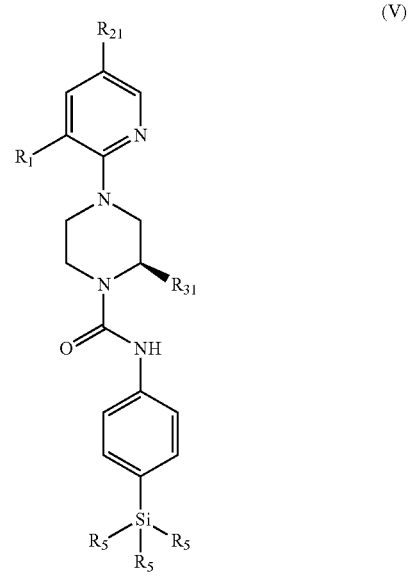

or any pharmaceutically-acceptable salt or hydrate thereof, wherein:

R$_1$ is halo, methyl, or CF$_3$;

R$_{21}$ is hydrogen, or

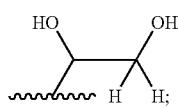

$R_{31}$ is —H or methyl; and each $R_5$ is independently:

(a) —H, halo, $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is optionally substituted with 1 or 2 hydroxy groups; or (b) $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is substituted by 1 or 2 substituents independently selected from:

(i) $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, $CH=NR_7$, $N(R_7)_2$, $NR_7OH$, $OR_7$, $C(O)R_7$, $C(O)OR_7$, $OC(O)OR_7$, $SR_7$, $S(O)R_7$, or $S(O)_2R_7$; or (ii)

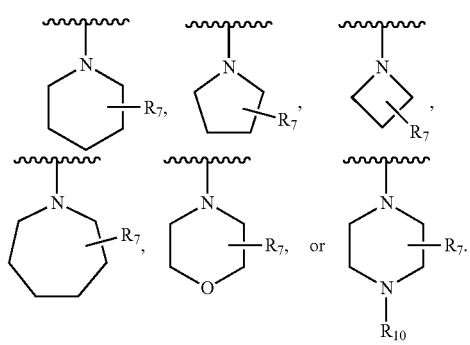

13. The compound of claim 3 having formula (VI):

(VI)

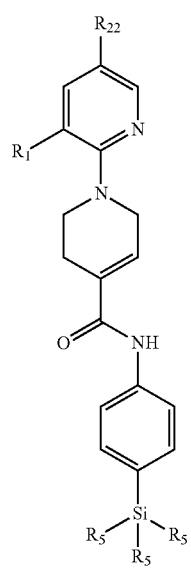

or any pharmaceutically-acceptable salt or hydrate thereof, wherein:

$R_1$ is halo, methyl, or $CF_3$;

$R_{22}$ is hydrogen, or

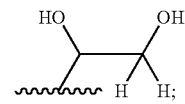

and each $R_5$ is independently:

(a) —H, halo, $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is optionally substituted with 1 or 2 hydroxy groups; or (b) $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is substituted by 1 or 2 substituents independently selected from:

(i) $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, $CH=NR_7$, $N(R_7)_2$, $NR_7OH$, $OR_7$, $C(O)R_7$, $C(O)OR_7$, $OC(O)OR_7$, $SR_7$, $S(O)R_7$, or $S(O)_2R_7$; or (ii)

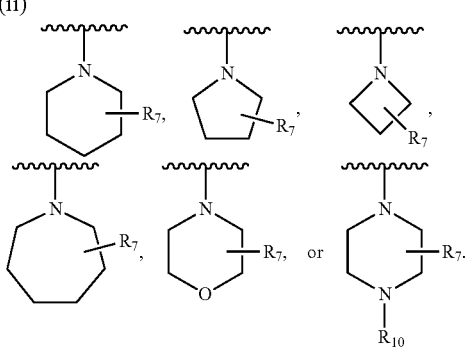

14. The compound of claim 1 having formula (VII):

(VII)

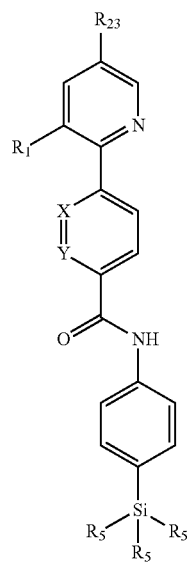

or any pharmaceutically-acceptable salt or hydrate thereof, wherein:

X is independently in each instance N or C;

Y is independently in each instance N or C;

$R_1$ is halo, methyl, or $CF_3$;

R₂₃ is —H, or

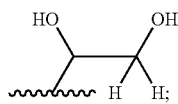

and each R₅ is independently:
(a) —H, halo, (C₁-C₆)alkyl, (C₂-C₆)alkenyl, (C₂-C₆)alkynyl, (C₃-C₈)cycloalkyl, (C₅-C₈)cycloalkenyl, or phenyl, each of which is optionally substituted with 1 or 2 hydroxy groups; or
(b) (C₁-C₆)alkyl, (C₂-C₆)alkenyl, (C₂-C₆)alkynyl, (C₃-C₈)cycloalkyl, (C₅-C₈)cycloalkenyl, or phenyl, each of which is substituted by 1 or 2 substituents independently selected from:
(i) CH₂C(halo)₃, C(halo)₃, CH(halo)₂, CH₂(halo), OC(halo)₃, OCH(halo)₂, OCH₂(halo), SC(halo)₃, SCH(halo)₂, SCH₂(halo), CN, OH, halo, N₃, NO₂, NH₂, CH=NR₇, N(R₇)₂, NR₇OH, OR₇, C(O)R₇, C(O)OR₇, OC(O)OR₇, SR₇, S(O)R₇, or S(O)₂R₇; or
(ii)

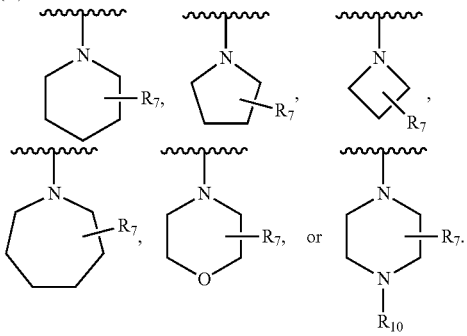

15. The compound according to claim 12, wherein R₁ is —F, —Cl or —CF₃.

16. The compound according to claim 13, wherein R₁ is —F, —Cl or —CF₃.

17. The compound according to claim 14, wherein R₁ is —F, —Cl or —CF₃.

18. The compound according to claim 12, wherein R₅ is methyl.

19. The compound according to claim 13, wherein R₅ is methyl.

20. The compound according to claim 14, wherein R₅ is methyl.

21. A method for treating pain comprising administering to a subject in need thereof an effective amount of a compound of Formula (I):

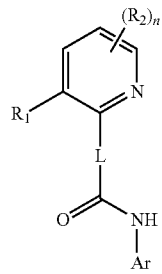

(I)

or any pharmaceutically-acceptable salt or hydrate thereof, wherein:

L is

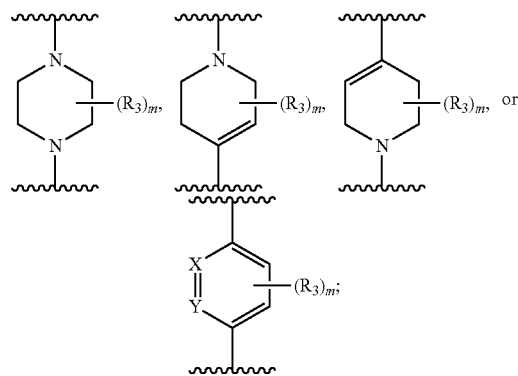

Ar is

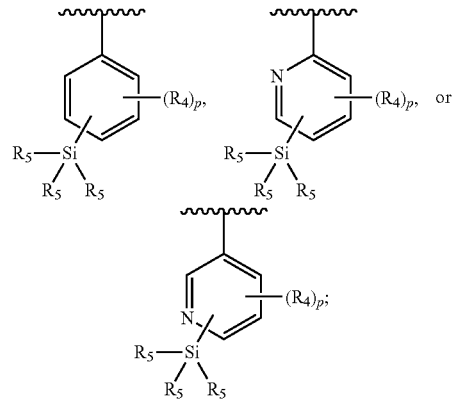

each X is independently N or C;
each Y is independently N or C;
m is 0, 1, 2, 3 or 4;
n is 0, 1, 2 or 3;
p is 0, 1, 2 or 3;
R₁ is —H, -halo, —(C₁-C₄)alkyl, —NO₂, —CN, —NH₂— C(halo)₃, —CH(halo)₂, —CH₂(halo), —OC(halo)₃, —OCH(halo)₂ or —OCH₂(halo);
each R₂ is independently:
(a) —H, -halo, OH, —O(C₁-C₄)alkyl, —CN, —NO₂, or —NH₂;
(b) —(C₁-C₁₀)alkyl, —(C₂-C₁₀)alkenyl, or —(C₂-C₁₀)alkynyl;
(c) -phenyl, each of which is unsubstituted or substituted with 1, 2 or 3 independently selected R₇ groups; or
(d) a group of Formula Q; wherein Q is:

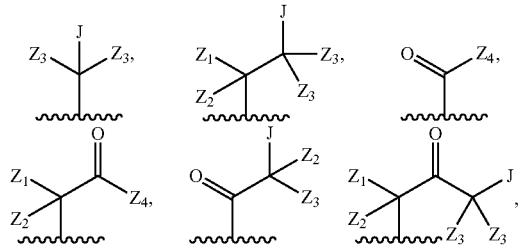

-continued

[Structures showing various chemical groups with $Z_1$, $Z_2$, $Z_3$, $R_{10}$ substituents including amide, sulfonamide variants]

of which:
  $Z_1$ is H, $OR_7$, $SR_7$, $CH_2$—$OR_7$, $CH_2$—$SR_7$, $CH_2$—N($R_{10}$)$_2$, or halo;
  $Z_2$ is H, ($C_1$-$C_6$)alkyl, ($C_2$-$C_6$)alkenyl, ($C_2$-$C_6$)alkynyl, $CH_2$—$OR_7$, phenyl, or halo;
  each $Z_3$ is independently H, ($C_1$-$C_6$)alkyl, ($C_2$-$C_6$)alkenyl, ($C_2$-$C_6$)alkynyl, or phenyl;
  $Z_4$ is H, OH, $OR_{10}$, ($C_1$-$C_6$)alkyl, or N($R_{10}$)$_2$;
  J is $OR_{10}$, $SR_{10}$, N($R_{10}$)$_2$ or CN;
each $R_3$ is independently
  (a) —H, $CH_2$—$OR_7$, ($C_1$-$C_6$)alkyl, halo, CN, OH, $NO_2$, or $NH_2$;
  (b) two $R_3$ groups together form a ($C_2$-$C_6$)bridge, which is unsubstituted or substituted with 1, 2 or 3 independently selected $R_4$ groups, and which bridge optionally contains —HC=CH— within the ($C_2$-$C_6$) bridge; or
  (c) two $R_3$ groups together form a —$CH_2$—N($R_a$)—$CH_2$— bridge, a $$-CH_2-N(C(O)R_b)-CH_2- \text{ bridge,}$$

or a $$-CH_2-N(S(O)_2R_b)-CH_2- \text{ bridge;}$$

wherein
  $R_a$ is —H, ($C_1$-$C_6$)alkyl, ($C_3$-$C_8$)cycloalkyl, —$CH_2$—C(O)—$R_c$, —$CH_2$—C(O)—$OR_c$, —$CH_2$—C(O)—N($R_c$)$_2$, —($CH_2$)$_2$—O—$R_c$, —($CH_2$)$_2$—S(O)$_2$—N($R_c$)$_2$, or —($CH_2$)$_2$—N($R_c$)S(O)$_2R_c$;
  each $R_b$ is independently:
    (a) —H, ($C_1$-$C_6$)alkyl, ($C_3$-$C_8$)cycloalkyl, —N($R_c$)$_2$, or N($R_c$)—($C_3$-$C_8$)cycloalkyl;
    (b) phenyl, pyridyl, or naphthyl, each of which is unsubstituted or substituted with 1, 2 or 3 independently selected $R_7$ groups;
  each $R_c$ is independently —H or ($C_1$-$C_4$)alkyl;

each $R_4$ is independently:
  (a) ($C_1$-$C_6$)alkyl, ($C_2$-$C_6$)alkenyl, ($C_2$-$C_6$)alkynyl, ($C_3$-$C_8$)cycloalkyl, ($C_5$-$C_8$)cycloalkenyl, or phenyl, each of which is optionally substituted with 1 or 2 hydroxy groups;
  (b) ($C_1$-$C_6$)alkyl, ($C_2$-$C_6$)alkenyl, ($C_2$-$C_6$)alkynyl, ($C_3$-$C_8$)cycloalkyl, ($C_5$-$C_8$)cycloalkenyl, or phenyl, each of which is substituted with 1 or 2 $R_d$; or
  (c) —H, $CH_2$C(halo)$_3$, C(halo)$_3$, CH(halo)$_2$, $CH_2$(halo), OC(halo)$_3$, OCH(halo)$_2$, $OCH_2$(halo), SC(halo)$_3$, SCH(halo)$_2$, $SCH_2$(halo), CN, OH, halo, $N_3$, $NO_2$, $NH_2$, CH=$NR_7$, N($R_7$)$_2$, $NR_7$OH, $OR_7$, C(O)$R_7$, C(O)$OR_7$, OC(O)$OR_7$, $SR_7$, S(O)$R_7$, S(O)$_2R_7$, or —$R_7$;
each $R_d$ is independently:
  (a) N($R_7$)$_2$, $NR_7$OH, $OR_7$, C(O)$R_7$, C(O)$OR_7$, OC(O)$OR_7$, $SR_7$, S(O)$R_7$, S(O)$_2R_7$; or
  (b)

[Structures showing N-containing heterocycles: piperidinyl, pyrrolidinyl, azetidinyl, azepanyl, morpholinyl, piperazinyl, each with $R_7$ substituent and $R_{10}$ on piperazine N]

each $R_5$ is independently:
  (a) —H, halo, ($C_1$-$C_6$)alkyl, ($C_2$-$C_6$)alkenyl, ($C_2$-$C_6$)alkynyl, ($C_3$-$C_8$)cycloalkyl, ($C_5$-$C_8$)cycloalkenyl, or phenyl, each of which is optionally substituted with 1 or 2 hydroxy groups; or
  (b) ($C_1$-$C_6$)alkyl, ($C_2$-$C_6$)alkenyl, ($C_2$-$C_6$)alkynyl, ($C_3$-$C_8$)cycloalkyl, ($C_5$-$C_8$)cycloalkenyl, or phenyl, each of which is substituted by 1 or 2 substituents independently selected from:
    (i) $CH_2$C(halo)$_3$, C(halo)$_3$, CH(halo)$_2$, $CH_2$(halo), OC(halo)$_3$, OCH(halo)$_2$, $OCH_2$(halo), SC(halo)$_3$, SCH(halo)$_2$, $SCH_2$(halo), CN, OH, halo, $N_3$, $NO_2$, $NH_2$, CH=$NR_7$, N($R_7$)$_2$, $NR_7$OH, $OR_7$, C(O)$R_7$, C(O)$OR_7$, OC(O)$OR_7$, $SR_7$, S(O)$R_7$, or S(O)$_2R_7$; or
    (ii)

[Structures showing N-containing heterocycles: piperidinyl, pyrrolidinyl, azetidinyl, azepanyl, morpholinyl, piperazinyl, each with $R_7$ substituent and $R_{10}$ on piperazine N]

$R_7$ is —H, ($C_1$-$C_6$)alkyl, ($C_2$-$C_6$)alkenyl, ($C_2$-$C_6$)alkynyl, ($C_3$-$C_8$)cycloalkyl, ($C_5$-$C_8$)cycloalkenyl, phenyl, ($C_1$-

$C_6$)haloalkyl, ($C_1$-$C_6$)hydroxyalkyl, ($C_1$-$C_6$)alkoxy($C_1$-$C_6$)alkyl, ($C_1$-$C_6$)alkyl-N($R_{10}$)$_2$, or CON($R_{10}$)$_2$; and $R_{10}$ is —H, ($C_1$-$C_4$)alkyl, ($C_1$-$C_4$)haloalkyl, ($C_1$-$C_4$)hydroxyalkyl, or ($C_1$-$C_4$)alkoxy($C_1$-$C_4$)alkyl.

22. The method for treating pain of claim 21, wherein the subject is administered an effective amount of a compound of formula (II):

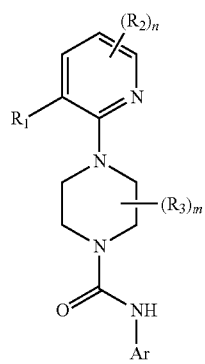

(II)

or any pharmaceutically-acceptable salt or hydrate thereof, wherein:

Ar is

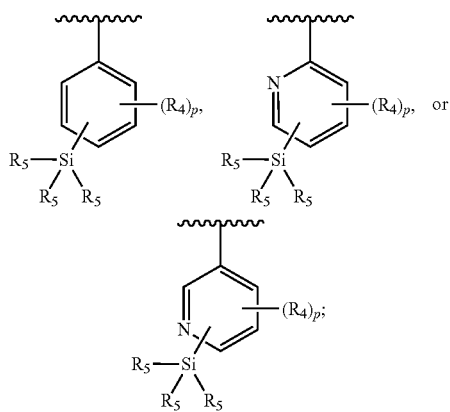

m is 0, 1, 2, 3 or 4;

n is 0, 1, 2 or 3;

p is 0, 1, 2 or 3;

$R_1$ is —H, -halo, —($C_1$-$C_4$)alkyl, —NO$_2$, —CN, —NH$_2$, —(halo)$_3$, —CH(halo)$_2$, —CH$_2$(halo), —OC(halo)$_3$, —OCH(halo)$_2$ or —OCH$_2$(halo);

each $R_2$ is independently:

(a) —H, -halo, —OH, —O($C_1$-$C_4$)alkyl, —CN, —NO$_2$, or —NH$_2$;

(b) —($C_1$-$C_{10}$)alkyl, —($C_2$-$C_{10}$)alkenyl, or —($C_2$-$C_{10}$)alkynyl;

(c) -phenyl, each of which is unsubstituted or substituted with 1, 2 or 3 independently selected $R_7$ groups; or (d) a group of Formula Q, wherein Q is:

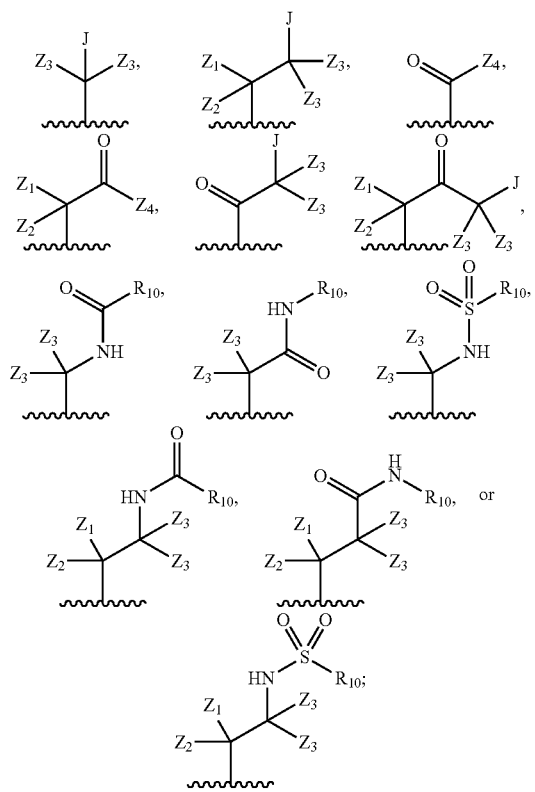

wherein:

$Z_1$ is H, OR$_7$, SR$_7$, CH$_2$—OR$_7$, CH$_2$—SR$_7$, CH$_2$—N(R$_{10}$)$_2$, or halo;

$Z_2$ is H, ($C_1$-$C_6$)alkyl, ($C_2$-$C_6$)alkenyl, ($C_2$-$C_6$)alkynyl, CH$_2$—OR$_7$, phenyl, or halo;

each $Z_3$ is independently H, ($C_1$-$C_6$)alkyl, ($C_2$-$C_6$)alkenyl, ($C_2$-$C_6$)alkynyl, or phenyl;

$Z_4$ is H, OH, OR$_{10}$, ($C_1$-$C_6$)alkyl, or N(R$_{10}$)$_2$;

J is OR$_{10}$, SR$_{10}$, N(R$_{10}$)$_2$ or CN;

each $R_3$ is independently (a) —H, CH$_2$—OR$_7$, ($C_1$-$C_6$)alkyl, halo, CN, OH, NO$_2$, or NH$_2$;

(b) two $R_3$ groups together form a ($C_2$-$C_6$)bridge, which is unsubstituted or substituted with 1, 2 or 3 independently selected $R_4$ groups, and which bridge optionally contains —HC=CH— within the ($C_2$-$C_6$)bridge; or (c) two $R_3$ groups together form a —CH$_2$—N(R$_a$)—CH$_2$— bridge, a

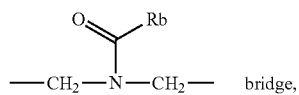

or a

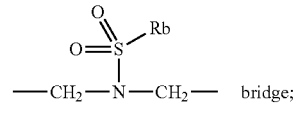

wherein

R$_a$ is —H, (C$_1$-C$_6$)alkyl, (C$_3$-C$_8$)cycloalkyl, —CH$_2$—C(O)—R$_c$, —CH$_2$—C(O)—OR$_c$, —CH$_2$—C(O)—N(R$_c$)$_2$, —(CH$_2$)$_2$—O—R$_c$, —(CH$_2$)$_2$—S(O)$_2$—N(R$_c$)$_2$, or —(CH$_2$)$_2$—N(R$_c$)S(O)$_2$—R$_c$;

each R$_b$ is independently:
(a) —H, (C$_1$-C$_6$)alkyl, (C$_3$-C$_8$)cycloalkyl, —N(R$_c$)$_2$, or N(R$_c$)—(C$_3$-C$_8$)cycloalkyl;
(b) phenyl, pyridyl, or naphthyl, each of which is unsubstituted or substituted with 1, 2 or 3 independently selected R$_7$ groups;

each R$_c$ is independently —H or (C$_1$-C$_4$)alkyl;

each R$_4$ is independently:
(a) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is optionally substituted with 1 or 2 hydroxy groups;
(b) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is substituted with 1 or 2 R$_d$; or
(c) —H, CH$_2$C(halo)$_3$, C(halo)$_3$, CH(halo)$_2$, CH$_2$(halo), OC(halo)$_3$, OCH(halo)$_2$, OCH$_2$(halo), SC(halo)$_3$, SCH(halo)$_2$, SCH$_2$(halo), CN, OH, halo, N$_3$, NO$_2$, NH$_2$, CH=NR$_7$, N(R$_7$)$_2$, NR$_7$OH, OR$_7$, C(O)R$_7$, C(O)OR$_7$, OC(O)OR$_7$, SR$_7$, S(O)R$_7$, S(O)$_2$R$_7$, or —R$_7$;

each R$_d$ is independently:
(a) N(R$_7$)$_2$, NR$_7$OH, OR$_7$, C(O)R$_7$, C(O)OR$_7$, OC(O)OR$_7$, SR$_7$, S(O)R$_7$, S(O)$_2$R$_7$; or
(b)

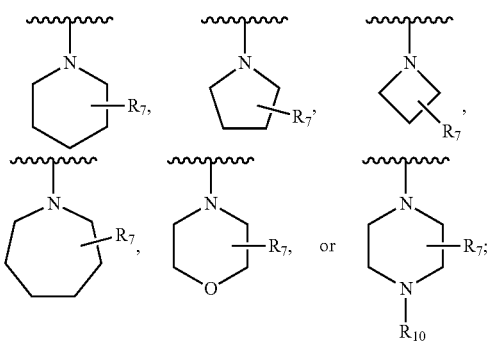

each R$_5$ is independently:
(a) —H, halo, (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is optionally substituted with 1 or 2 hydroxy groups; or
(b) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is substituted by 1 or 2 substituents independently selected from:
(i) CH$_2$C(halo)$_3$, C(halo)$_3$, CH(halo)$_2$, CH$_2$(halo), OC(halo)$_3$, OCH(halo)$_2$, OCH$_2$(halo), SC(halo)$_3$, SCH(halo)$_2$, SCH$_2$(halo), CN, OH, halo, N$_3$, NO$_2$, NH$_2$, CH=NR$_7$, N(R$_7$)$_2$, NR$_7$OH, OR$_7$, C(O)R$_7$, C(O)OR$_7$, OC(O)OR$_7$, SR$_7$, S(O)R$_7$, or S(O)$_2$R$_7$; or
(ii)

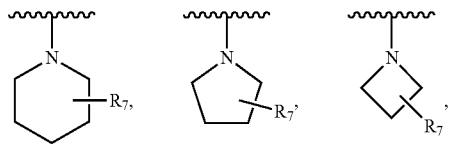

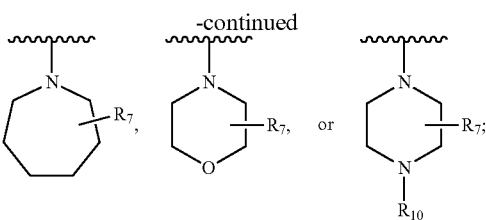

wherein:
R$_7$ is —H, (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, phenyl, (C$_1$-C$_6$)haloalkyl, (C$_1$-C$_6$)hydroxyalkyl, (C$_1$-C$_6$)alkoxy(C$_1$-C$_6$)alkyl, (C$_1$-C$_6$)alkyl-N(R$_{10}$)$_2$, or CON(R$_{10}$)$_2$; R$_{10}$ is —H, (C$_1$-C$_4$)alkyl, (C$_1$-C$_4$)haloalkyl, (C$_1$-C$_4$)hydroxyalkyl, or (C$_1$-C$_4$)alkoxy(C$_1$-C$_4$)alkyl.

23. The method for treating pain of claim 21, wherein the subject is administered an effective amount of a compound of formula (III):

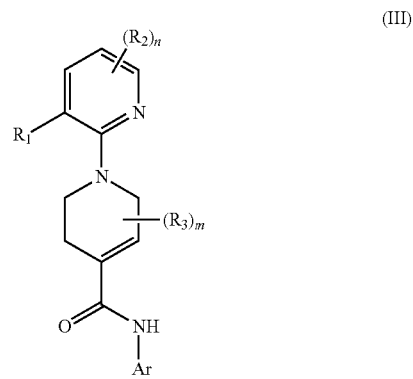

(III)

or any pharmaceutically-acceptable salt or hydrate thereof, wherein:

Ar is

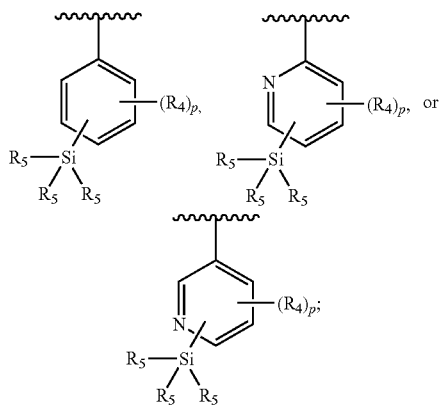

m 0, 1, 2, 3 or 4;
n is 0, 1, 2 or 3;
p is 0, 1, 2 or 3;
R$_1$ is —H, -halo, —(C$_1$-C$_4$)alkyl, —NO$_2$, —CN, —NH$_2$, —C(halo)$_3$, —CH(halo)$_2$, —CH$_2$(halo), —OC(halo)$_3$, —OCH(halo)$_2$ or —OCH$_2$(halo);
each R$_2$ is independently:
(a) —H, -halo, —OH, —O(C$_1$-C$_4$)alkyl, —CN, —NO$_2$, or —NH$_2$;

(b) —(C$_1$-C$_{10}$)alkyl, —(C$_2$-C$_{10}$)alkenyl, or —(C$_2$-C$_{10}$)alkynyl;
(c) -phenyl, each of which is unsubstituted or substituted with 1, 2 or 3 independently selected R$_7$ groups; or
(d) a group of Formula Q; wherein Q is:

[chemical structures of Formula Q options showing variants with Z$_1$, Z$_2$, Z$_3$, Z$_4$, J, R$_{10}$ substituents]

wherein:
Z$_1$ is H, OR$_7$, SR$_7$, CH$_2$—OR$_7$, CH$_2$—SR$_7$, CH$_2$—N(R$_{10}$)$_2$, or halo;
Z$_2$ is H, (C$_1$-C$_6$)alkyl, (C$_2$-C$_6$)alkenyl, (C$_2$-C$_6$)alkynyl, CH$_2$—OR$_7$, phenyl, or halo;
each Z$_3$ is independently H, (C$_1$-C$_6$)alkyl, (C$_2$-C$_6$)alkenyl, (C$_2$-C$_6$)alkynyl, or phenyl;
Z$_4$ is H, OH, OR$_{10}$, (C$_1$-C$_6$)alkyl, or N(R$_{10}$)$_2$;
J is OR$_{10}$, SR$_{10}$, N(R$_{10}$)$_2$ or CN;
each R$_3$ is independently
(a) —H, CH$_2$—OR$_7$, (C$_1$-C$_6$)alkyl, halo, CN, OH, NO$_2$, or NH$_2$;
(b) two R$_3$ groups together form a (C$_2$-C$_6$)bridge, which is unsubstituted or substituted with 1, 2 or 3 independently selected R$_4$ groups, and which bridge optionally contains —HC=CH— within the (C$_2$-C$_6$)bridge; or
(c) two R$_3$ groups together form a —CH$_2$—N(R$_a$)—CH$_2$— bridge, a

[structure: —CH$_2$—N(C(O)R$_b$)—CH$_2$— bridge]

bridge, or a

[structure: —CH$_2$—N(S(O)$_2$R$_b$)—CH$_2$— bridge]

bridge;

wherein
R$_a$ is —H, (C$_1$-C$_6$)alkyl, (C$_3$-C$_8$)cycloalkyl, —CH$_2$—C(O)—R$_c$, —CH$_2$—C(O)—OR$_c$, —CH$_2$—C(O)—N(R$_c$)$_2$, —(CH$_2$)$_2$—O—R$_c$, —(CH$_2$)$_2$—S(O)$_2$—N(R$_c$)$_2$, or —(CH$_2$)$_2$—N(R$_c$)S(O)$_2$—R$_c$;
each R$_b$ is independently:
(a) —H, (C$_1$-C$_6$)alkyl, (C$_3$-C$_8$)cycloalkyl, —N(R$_c$)$_2$, or N(R$_c$)—(C$_3$-C$_8$)cycloalkyl;
(b) phenyl, pyridyl, or naphthyl, each of which is unsubstituted or substituted with 1, 2 or 3 independently selected R$_7$ groups;
each R$_c$ is independently —H or (C$_1$-C$_4$)alkyl;
each R$_4$ is independently:
(a) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is optionally substituted with 1 or 2 hydroxy groups;
(b) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is substituted with 1 or 2 R$_d$; or
(c) —H, CH$_2$C(halo)$_3$, C(halo)$_3$, CH(halo)$_2$, CH$_2$(halo), OC(halo)$_3$, OCH(halo)$_2$, OCH$_2$(halo), SC(halo)$_3$, SCH(halo)$_2$, SCH$_2$(halo), CN, OH, halo, N$_3$, NO$_2$, NH$_2$, CH=NR$_7$, N(R$_7$)$_2$, NR$_7$OH, OR$_7$, C(O)R$_7$, C(O)OR$_7$, OC(O)OR$_7$, SR$_7$, S(O)R$_7$, S(O)$_2$R$_7$, or —R$_7$;
each R$_d$ is independently:
(a) N(R$_7$)$_2$, NR$_7$OH, OR$_7$, C(O)R$_7$, C(O)OR$_7$, OC(O)OR$_7$, SR$_7$, S(O)R$_7$, S(O)$_2$R$_7$; or
(b)

[ring structures: piperidinyl, pyrrolidinyl, azetidinyl, azepanyl, morpholinyl, piperazinyl with R$_7$ or R$_{10}$ substituents]

each R$_5$ is independently:
(a) —H, halo, (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is optionally substituted with 1 or 2 hydroxy groups; or
(b) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is substituted by 1 or 2 substituents independently selected from:
(i) CH$_2$C(halo)$_3$, C(halo)$_3$, CH(halo)$_2$, CH$_2$(halo), OC(halo)$_3$, OCH(halo)$_2$, OCH$_2$(halo), SC(halo)$_3$, SCH(halo)$_2$, SCH$_2$(halo), CN, OH, halo, N$_3$, NO$_2$, NH$_2$, CH=NR$_7$, N(R$_7$)$_2$, NR$_7$OH, OR$_7$, C(O)R$_7$, C(O)OR$_7$, OC(O)OR$_7$, SR$_7$, S(O)R$_7$, or S(O)$_2$R$_7$; or (ii)

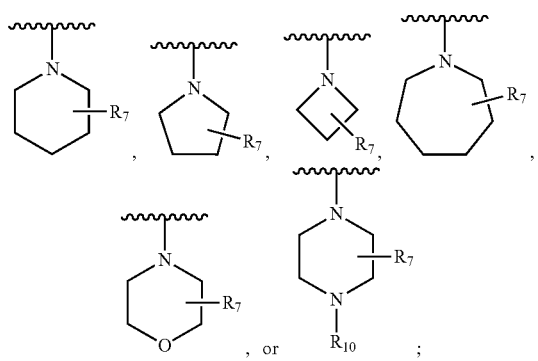

wherein:
R$_7$ is —H, (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, phenyl, (C$_1$-C$_6$)haloalkyl, (C$_1$-C$_6$)hydroxyalkyl, (C$_1$-C$_6$)alkoxy(C$_1$-C$_6$)alkyl, (C$_1$-C$_6$)alkyl-N(R$_{10}$)$_2$, or CON(R$_{10}$)$_2$; and
R$_{10}$ is —H, (C$_1$-C$_4$)alkyl, (C$_1$-C$_4$)haloalkyl, (C$_1$-C$_4$)hydroxyalkyl, or (C$_1$-C$_4$)alkoxy(C$_1$-C$_4$)alkyl.

24. The method for treating pain of claim 21, wherein the subject is administered an effective amount of a compound of formula (V):

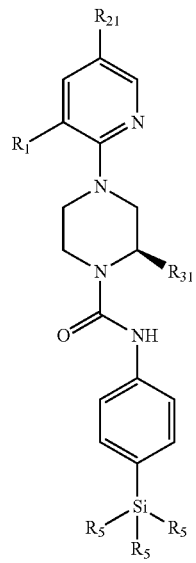

(V)

or any pharmaceutically-acceptable salt or hydrate thereof, wherein:
R$_1$ is halo, methyl, or CF$_3$;
R$_{21}$ is hydrogen, or

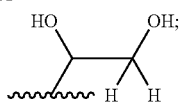 [SMILES: *C(O)CO]

R$_{31}$ is —H or methyl; and
each R$_5$ is independently:
(a) —H, halo, (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is optionally substituted with 1 or 2 hydroxy groups; or (b) (C$_1$-C$_6$)alkyl, (C$_2$-C$_6$)alkenyl, (C$_2$-C$_6$)alkynyl, (C$_3$-C$_8$)cycloalkyl, (C$_5$-C$_8$)cycloalkenyl, or phenyl, each of which is substituted by 1 or 2 substituents independently selected from:
(i) CH$_2$C(halo)$_3$, C(halo)$_3$, CH(halo)$_2$, CH$_2$(halo), OC(halo)$_3$, OCH(halo)$_2$, OCH$_2$(halo), SC(halo)$_3$, SCH(halo)$_2$, SCH$_2$(halo), CN, OH, halo, N$_3$, NO$_2$, NH$_2$, CH=NR$_7$, N(R$_7$)$_2$, NR$_7$OH, OR$_7$, C(O)R$_7$, C(O)OR$_7$, OC(O)OR$_7$, SR$_7$, S(O)R$_7$, or S(O)$_2$R$_7$; or
(i)

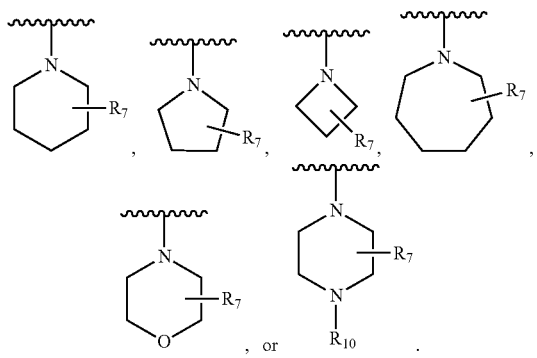

25. The method for treating pain of claim 21, wherein the subject is administered a therapeutically effective amount of a compound of formula (VI):

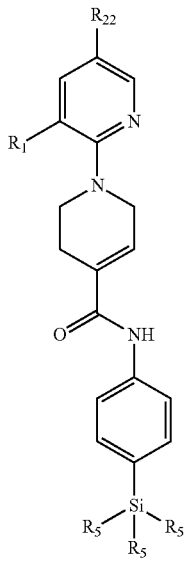

(VI)

or any pharmaceutically-acceptable salt or hydrate thereof, wherein:
R$_1$ is halo, methyl, or CF$_3$;
R$_{22}$ is hydrogen, or

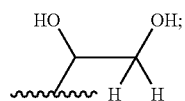

and each $R_5$ is independently:
- (a) —H, halo, $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is optionally substituted with 1 or 2 hydroxy groups; or
- (b) $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is substituted by 1 or 2 substituents independently selected from:
  - (i) $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, $CH=NR_7$, $N(R_7)_2$, $NR_7OH$, $OR_7$, $C(O)R_7$, $C(O)OR_7$, $OC(O)OR_7$, $SR_7$, $S(O)R_7$, or $S(O)_2R_7$; or
  - (ii)

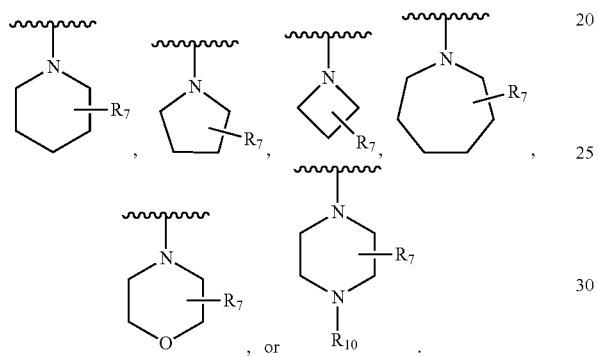

26. The method for treating pain of claim 21, wherein the subject is administered an effective amount of a compound of formula (VII):

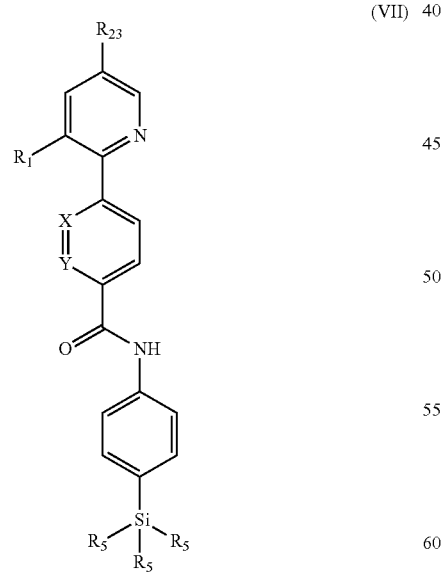

(VII)

or any pharmaceutically-acceptable salt or hydrate thereof, wherein:

X is independently in each instance N or C;

Y is independently in each instance N or C;

$R_1$ is halo, methyl, or $CF_3$;

$R_{23}$ is —H, or

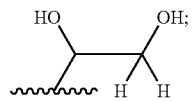

and each $R_5$ is independently:
- (a) —H, halo, $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is optionally substituted with 1 or 2 hydroxy groups; or
- (b) $(C_1-C_6)$alkyl, $(C_2-C_6)$alkenyl, $(C_2-C_6)$alkynyl, $(C_3-C_8)$cycloalkyl, $(C_5-C_8)$cycloalkenyl, or phenyl, each of which is substituted by 1 or 2 substituents independently selected from:
  - (i) $CH_2C(halo)_3$, $C(halo)_3$, $CH(halo)_2$, $CH_2(halo)$, $OC(halo)_3$, $OCH(halo)_2$, $OCH_2(halo)$, $SC(halo)_3$, $SCH(halo)_2$, $SCH_2(halo)$, CN, OH, halo, $N_3$, $NO_2$, $NH_2$, $CH=NR_7$, $N(R_7)_2$, $NR_7OH$, $OR_7$, $C(O)R_7$, $C(O)OR_7$, $OC(O)OR_7$, $SR_7$, $S(O)R_7$, or $S(O)_2R_7$; or
  - (ii)

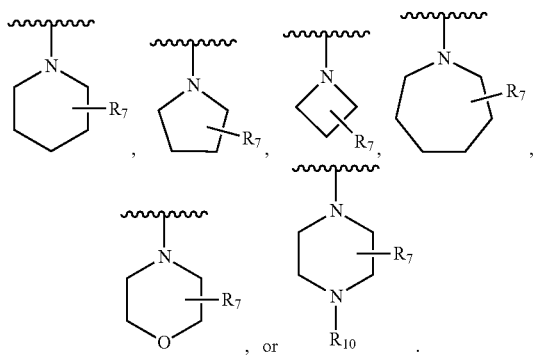

27. The compound of claim 1, wherein the compound is selected from the group consisting of:

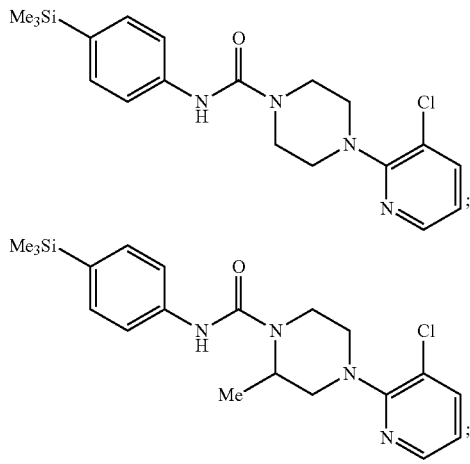

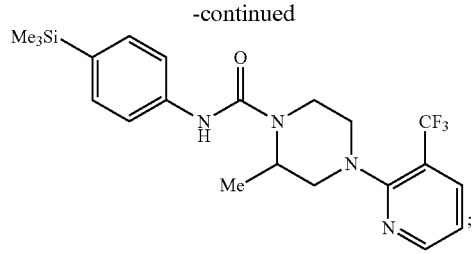
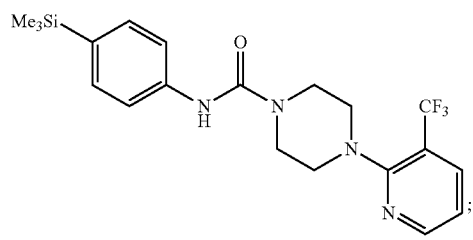
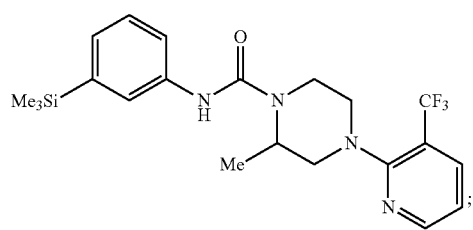
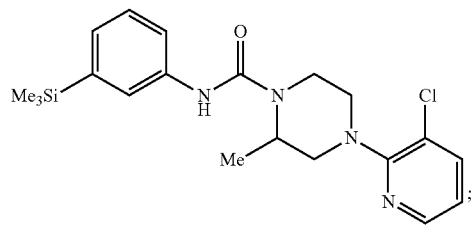
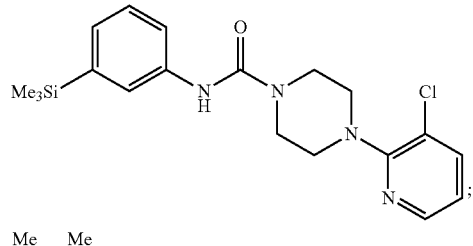
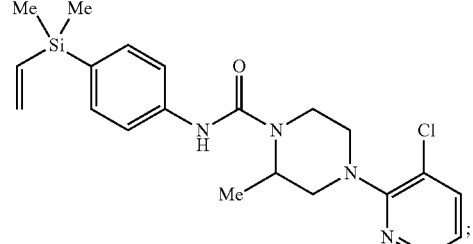
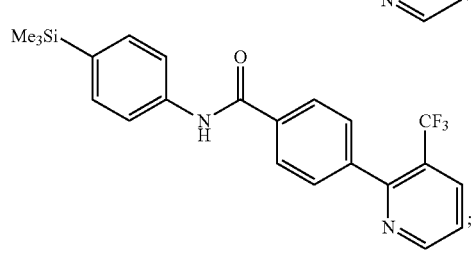
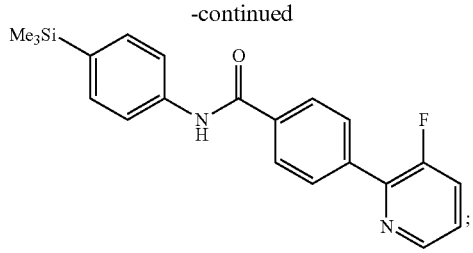
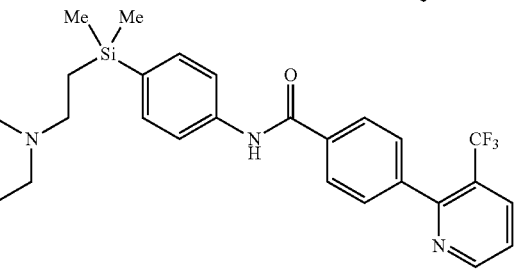
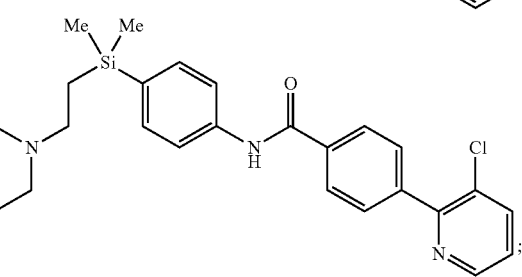
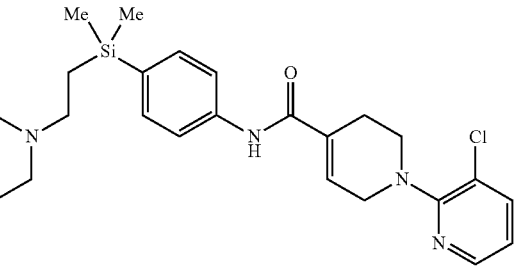
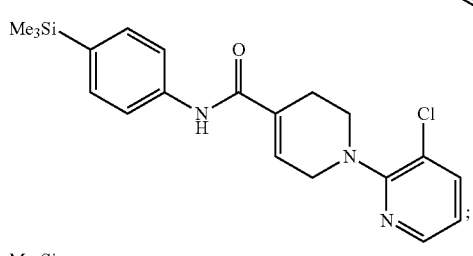
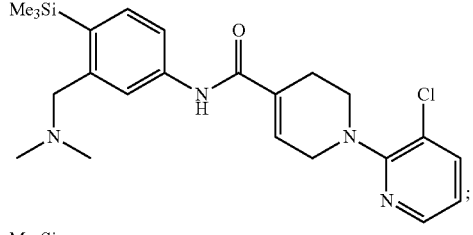
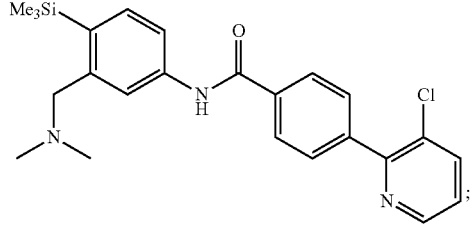

-continued
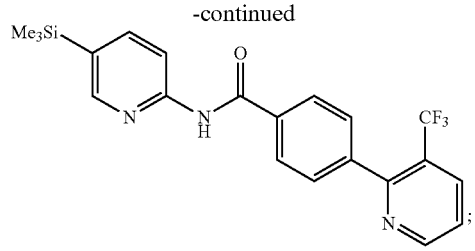
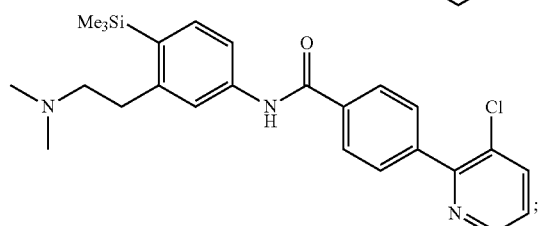
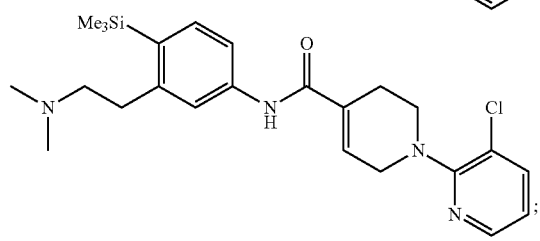
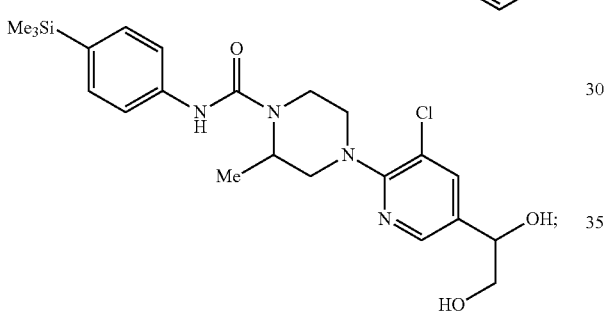
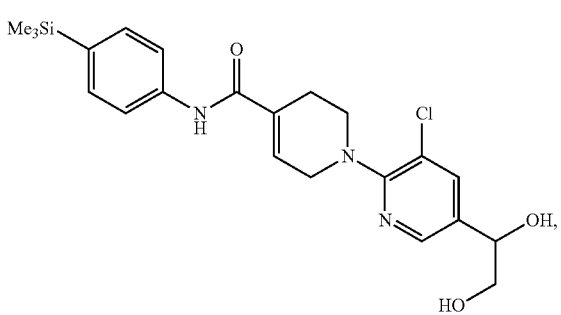
or a pharmaceutically acceptable salt thereof.
28. The compound of claim 1, wherein the compound is selected from the group consisting of:
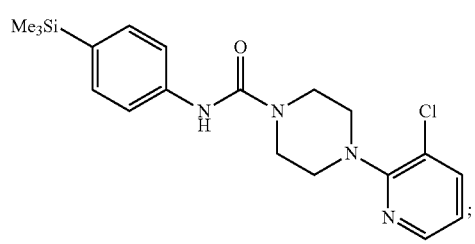
-continued
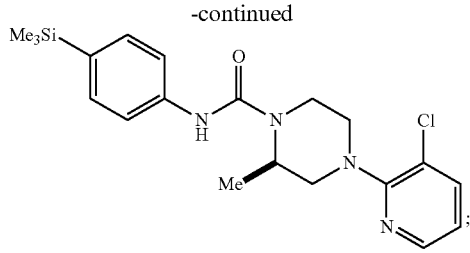
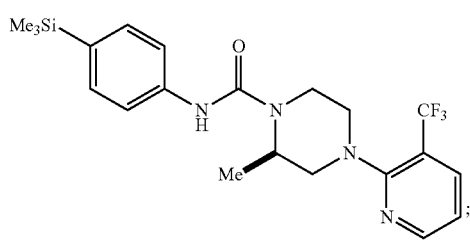
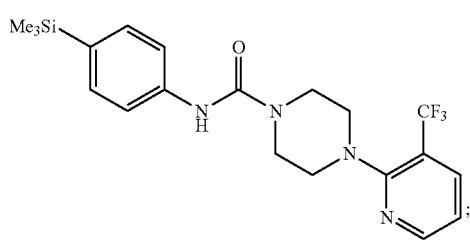
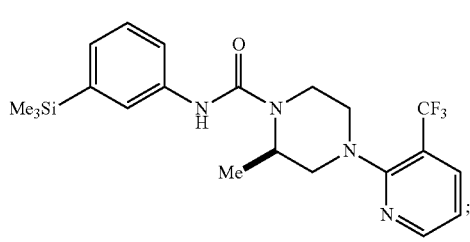
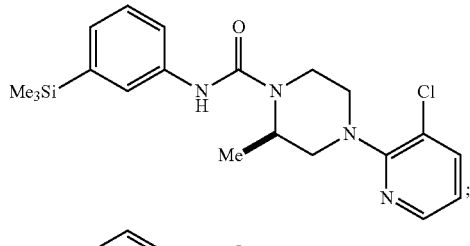
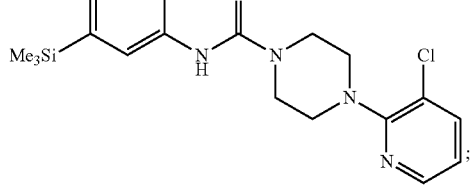
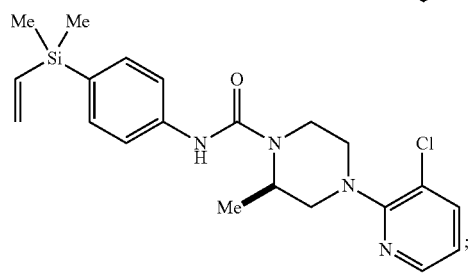

111
-continued
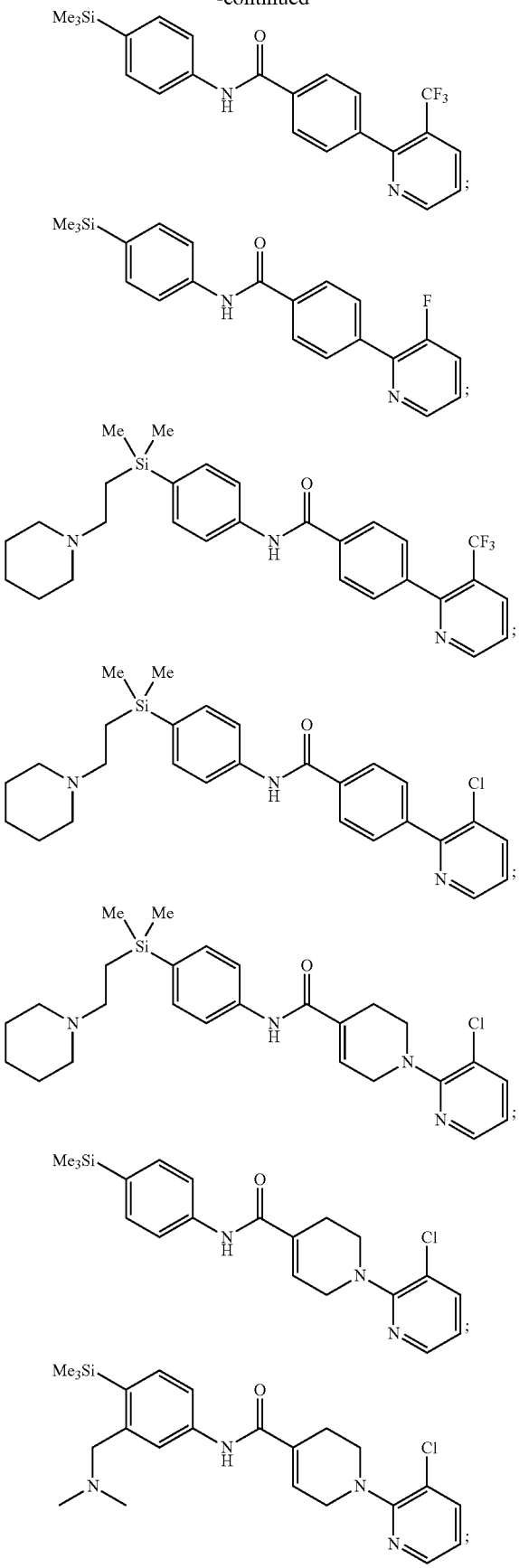
112
-continued
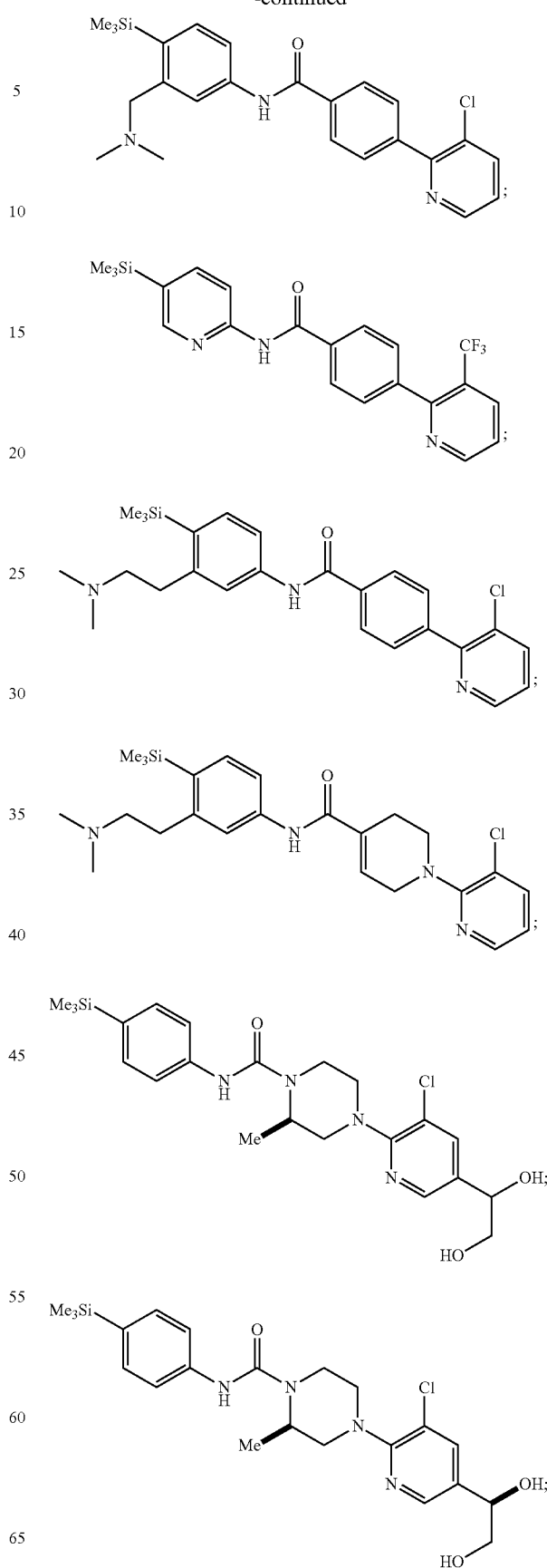

-continued
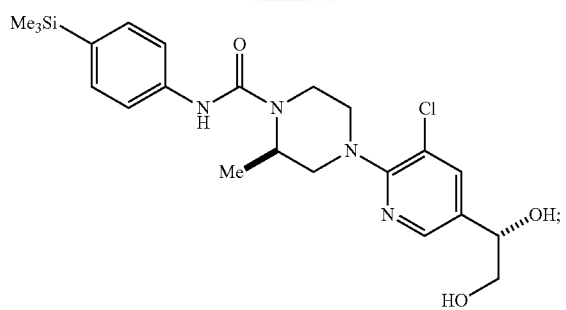
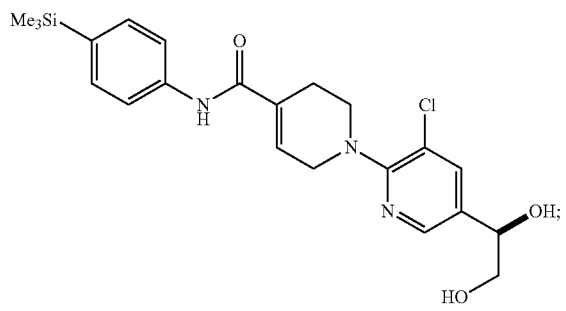
and
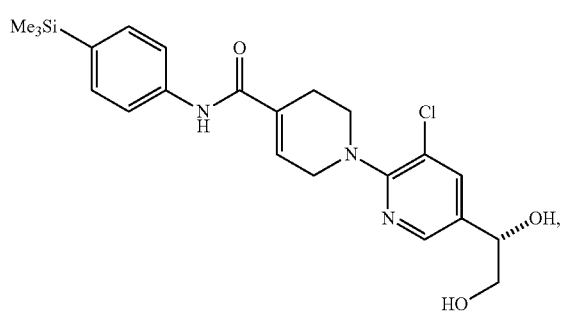
or a pharmaceutically acceptable salt thereof.
29. The compound of claim 27, wherein the compound is selected from the group consisting of:
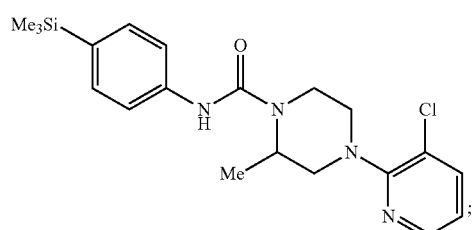
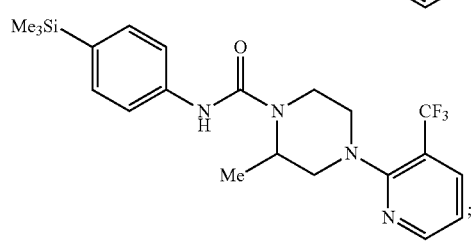
-continued
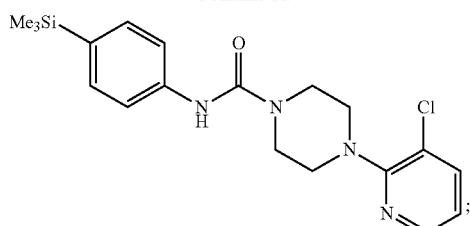
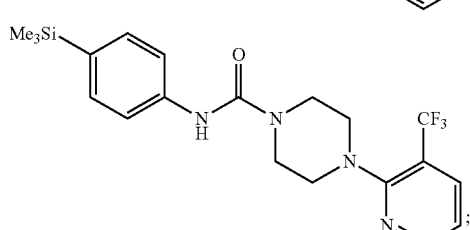
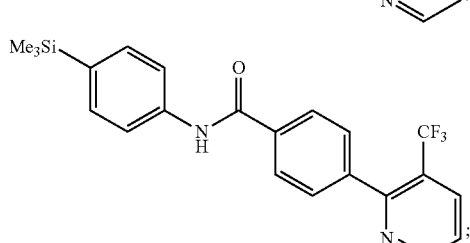
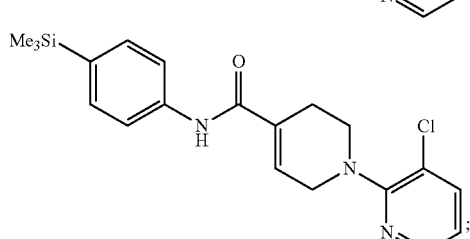
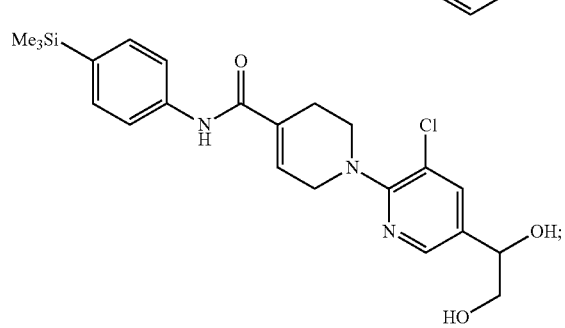
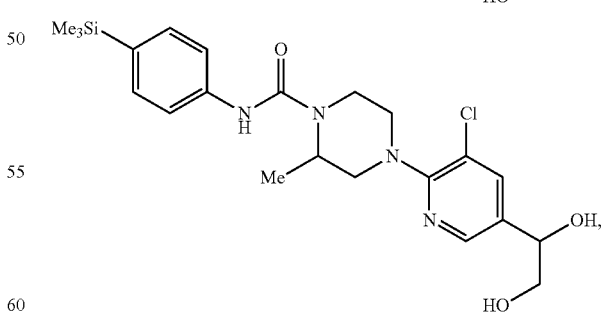
or
a pharmaceutically acceptable salt thereof.
30. The compound of claim 28, wherein the compound is selected from the group consisting of:

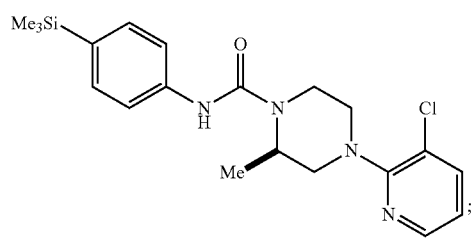
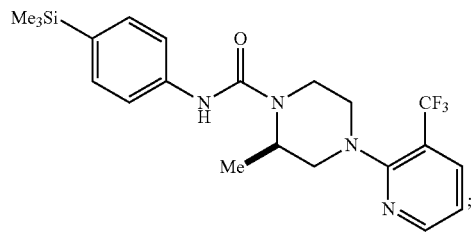
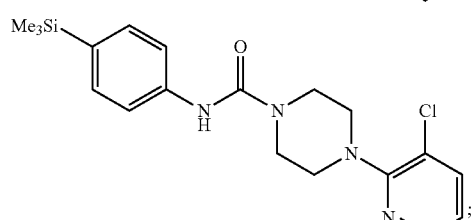
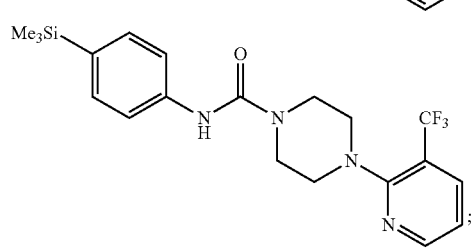
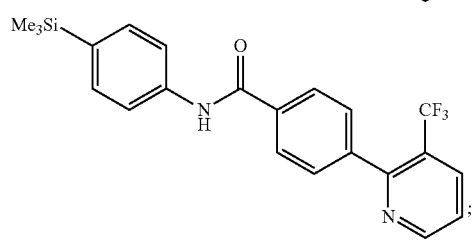
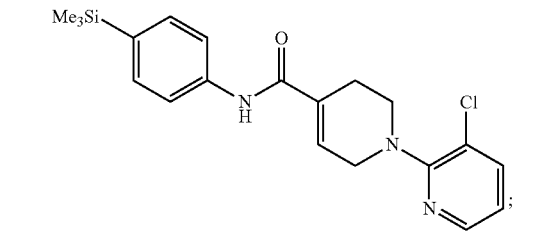
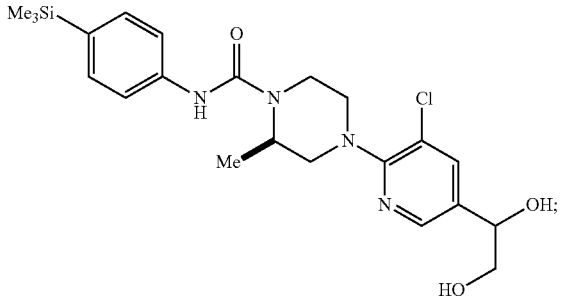
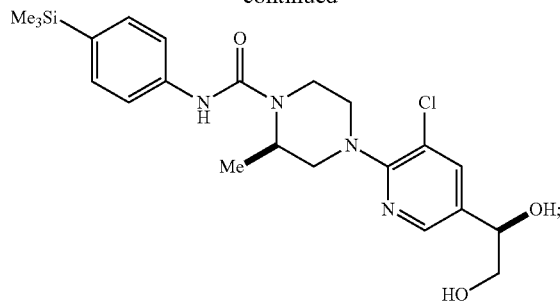
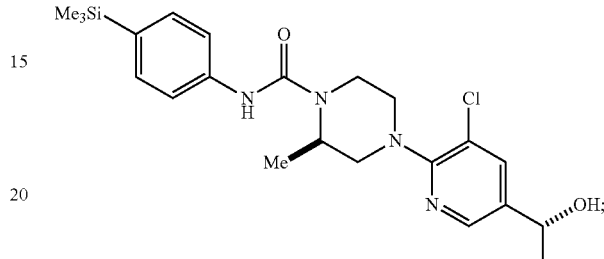
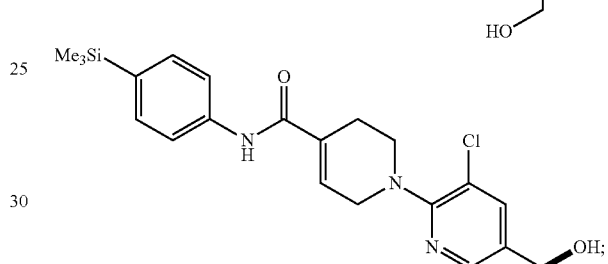
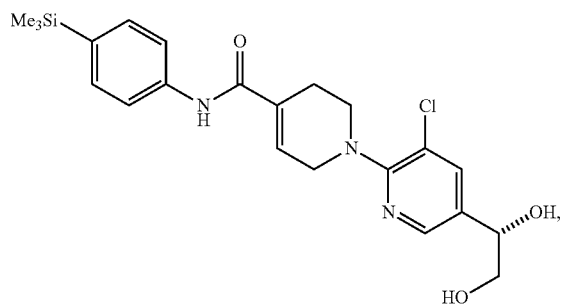
and
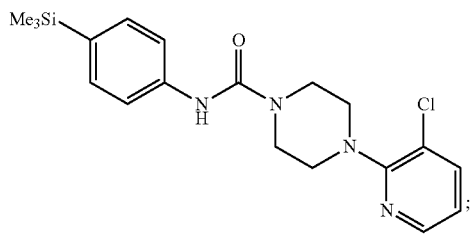
or a pharmaceutically acceptable salt thereof.
31. The method of claim 21, wherein the compound is selected from the group consisting of:

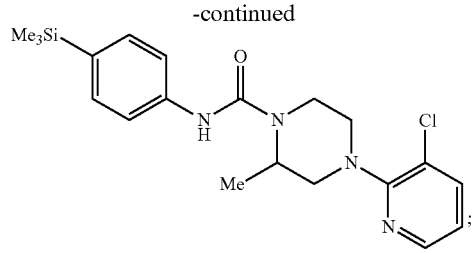
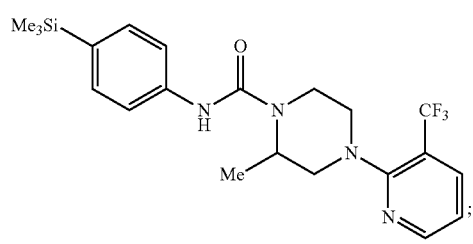
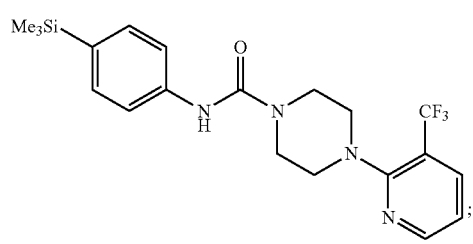
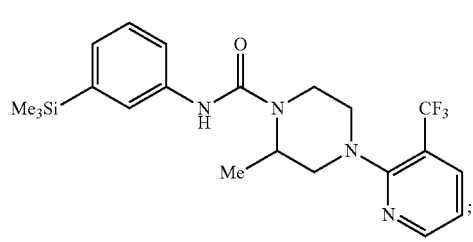
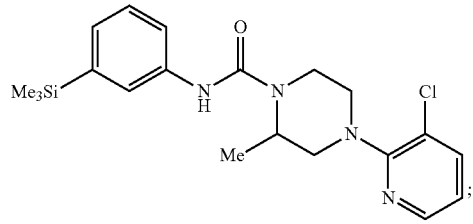
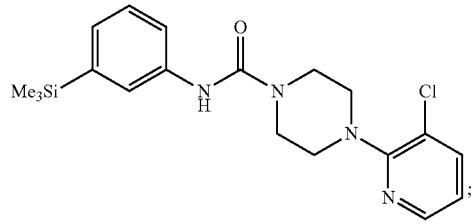
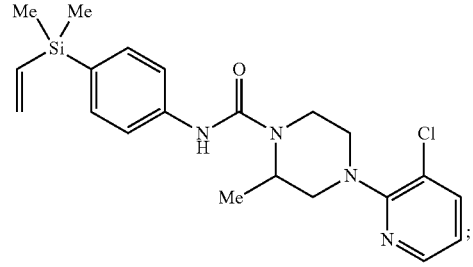
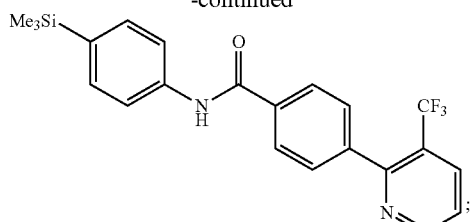
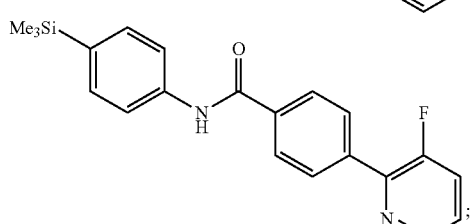
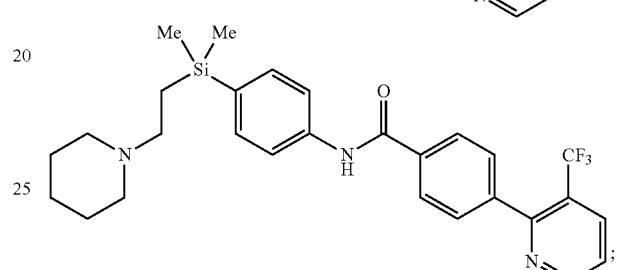
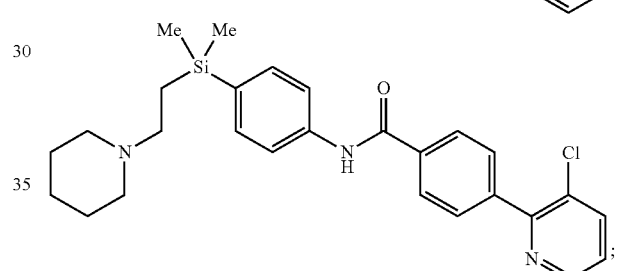
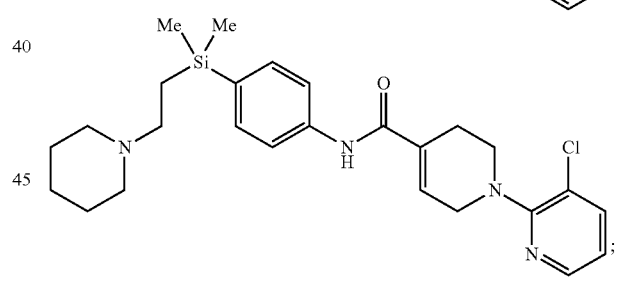
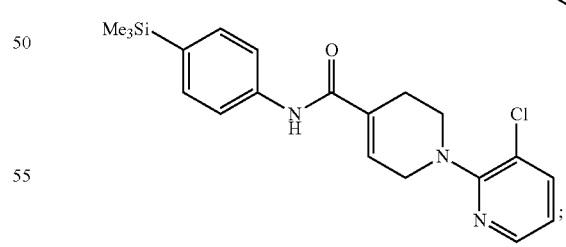
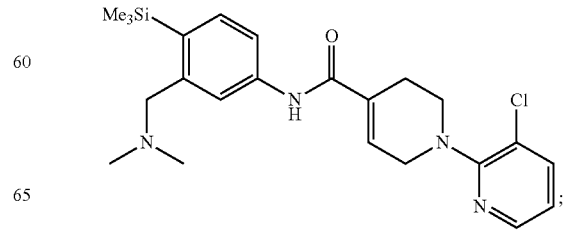

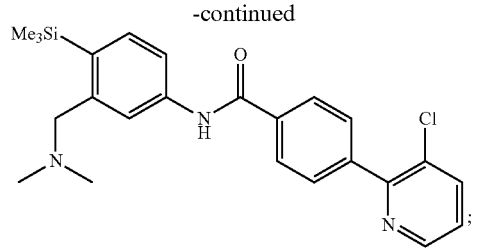
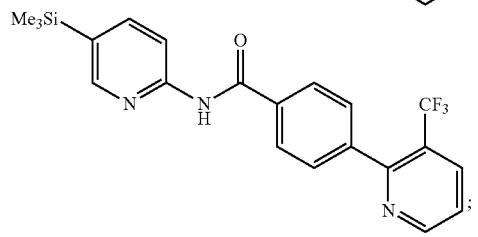
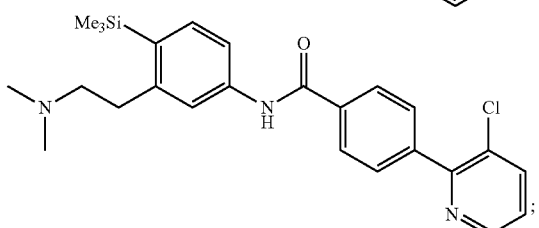
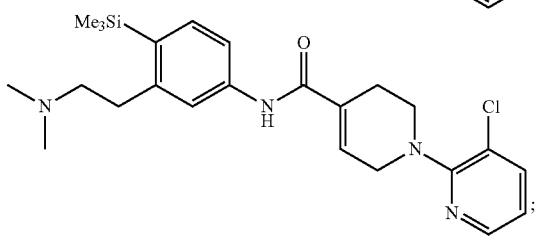
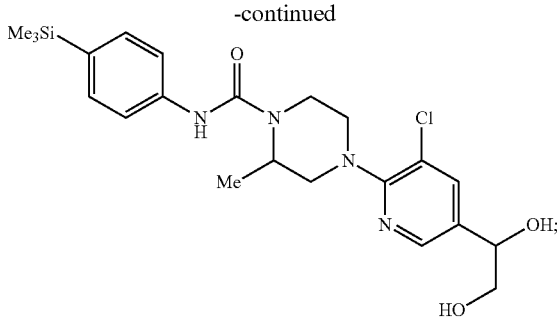
and
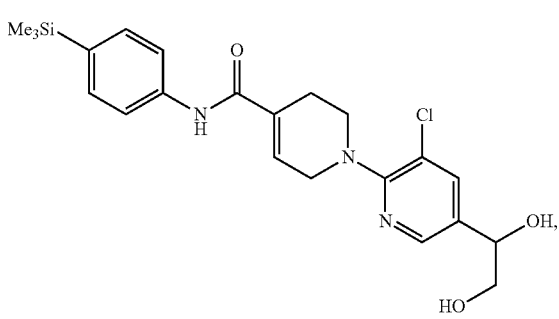
or a pharmaceutically acceptable salt thereof.
* * * * *